US007230139B2

(12) United States Patent
Lavallee et al.

(10) Patent No.: US 7,230,139 B2
(45) Date of Patent: *Jun. 12, 2007

(54) DITERPENOID COMPOUNDS, COMPOSITIONS THEREOF AND THEIR USE AS ANTI-CANCER OR ANTI-FUNGAL AGENTS

(75) Inventors: Jean-Francois Lavallee, Milles-Iles (CA); Terrence W. Doyle, Killingworth, CT (US); Elise Rioux, Montreal (CA); Laurent Belec, Montreal (CA); Daniel Rabouin, Laval (CA); Xavier Billot, Montreal (CA); Samuel Fortin, Ste-Luce (CA)

(73) Assignee: Gemin X Biotechnologies, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/865,262

(22) Filed: Jun. 10, 2004

(65) Prior Publication Data

US 2005/0032802 A1 Feb. 10, 2005

(51) Int. Cl.
| | |
|---|---|
| *C07C 43/162* | (2006.01) |
| *C07C 43/164* | (2006.01) |
| *C07C 43/166* | (2006.01) |
| *C07C 49/225* | (2006.01) |
| *C07D 237/36* | (2006.01) |
| *C07D 239/70* | (2006.01) |
| *A61K 31/085* | (2006.01) |
| *A61K 31/121* | (2006.01) |
| *A61K 31/502* | (2006.01) |
| *A61K 31/517* | (2006.01) |
| *A61P 35/00* | (2006.01) |

(52) U.S. Cl. .................. 568/326; 544/179; 544/180; 544/234; 544/249; 544/344; 514/680; 514/248; 514/250; 514/267

(58) Field of Classification Search ............... 568/326; 514/680
See application file for complete search history.

(56) References Cited

U.S. PATENT DOCUMENTS 5,480,906 A 1/1996 Creemer et al.

FOREIGN PATENT DOCUMENTS

| GB | 2302021 | 10/1996 |
|---|---|---|
| WO | WO/9851702 | 11/1998 |
| WO | WO 99/45919 | 9/1999 |
| WO | WO 2003/024183 | 3/2003 |
| WO | WO 2004/024093 | 3/2004 |

OTHER PUBLICATIONS

Cecil Textbook of Medicine, edited by Bennet, J.C., and Plum F., 20th edition, vol. 1, 1004-1010, 1996.*
Slamenova et al., Basic Clin. Pharmacol. Toxicol. 94(6): 282-290,2004.*
Turner et al., Current Pharmaceutical Design. 2, 209-224, 1996.*
Sugar et al., Diagn. Microbiol. Infect. Dis. 21: 129-133, 1995.*
Cambie et al., 1998, "A Synthesis of Triptoquinones D, E, and F from Podocarpic Acid," Aust. J. Chem. 51(10):931-940.
Cambie et al., 1971, Aust. J. Chem. 24:2611.
Carreiras, 1990, "Rearranged abietane diterpenoids from the root of *teucrium polium* subsp. *vincentinum*," Tetrahedron 46(3):847.
Ceruti et al., 1998, "29-Methylidene-2,3-oxidosqualene derivatives as stereospecific mechanism-based inhibitors of liver and yeast oxidosqualene cyclase," J. Med. Chem. 41(4):540-554.
Corey et al., 1997, "A Simple Enantioselective Synthesis of the Biologically Active Tetracyclic Marine Sesterterpene Scalarenedial," J. Am. Chem. Soc. 119:9927-9928.
Crispino et al., 1993, Synthesis 777-779.
Cuadrado et al., 1992, "Rearranged abietane diterpenoids from the root of two *Teucrium* species," Phytochemistry 31(5):1697-1701.
Danishefsky et al., 1979, "Derivatives of 1-methoxy-3-trimethylsilyloxy-1,3-butadiene for Diels-Alder reactions," J. Am. Chem. Soc. 101:7001-7008.
Fishner et al., 2002, "D-ring modified steroids as potent oestrone sulphatase inhibitors," Eur. J. Cancer 38(7):S125 Abstract 408.
Fuchino et al., 1998, "Two New Abietanes from *Lycopodium deuterodensum*," Aust. J. Chem. 1998, 51(2):175.
Greico et al., 1998, "Synthetic Studies on Quassinoids: Total Synthesis and Biological Evaluation of (+)-Des-D-chaparrinone," J. Org. Chem. 63:5929-5936.
Ito et al., 1978, "Synthesis of .alpha.,.beta.-unsaturated carbonyl compounds by palladium(II)-catalyzed dehydrosilylation of silyl enol ethers," J. Org. Chem. 43:1011-1013.
Kuehne, 1961, "A Stereospecific Route to the Dehydroabietic Acid Configuration," J. Amer. Chem. Soc. 83:1492-1498.
Ley et al., 1994, "Tetrapropylammonium Perruthenate, Pr4N+RuO4-, TPAP : Catalytic Oxidant For Organic Synthesis," Synthesis 639-666.
Lin et al., 2001, "Chemical Constituents from *Drypetes littoralis*," J. Nat. Prod. 64:707-709.
Maercker, 1965, "The Wittig Reaction," Organic Reactions 14:270-335.
Maryanoff et al., 1985, "Stereochemistry of the Wittig reaction. Effect of nucleophilic groups in the phosphonium ylide," J. Am. Chem. Soc. 107:217-226.
Murphy et al., 1960, "Structures Related to Morphine. XIV.[1] 2'-Hydroxy-5-methyl-2-phenethyl-6,7-benzomorphan, the 9-Demethyl Analog of NIH 7519 (Phenazocine) from 3,4-Dihydro-7-methoxy-2(1H)naphthalenone," J. Org. Chem. 25:1386-1388.

(Continued)

*Primary Examiner*—Venkataraman Balasubramanian
(74) *Attorney, Agent, or Firm*—Jones Day

(57) ABSTRACT

The present invention relates to Diterpenoid Compounds, compositions comprising an effective amount of a Diterpenoid Compound, and methods useful for treating or preventing cancer or a neoplastic disorder comprising administering an effective amount of a Diterpenoid Compound. The compounds, compositions, and methods of the invention are also useful for inhibiting the growth of a cancer cell or neoplastic cell, or for inducing apoptosis in a cancer or neoplastic cell. The compounds, compositions, and methods of the invention are further useful for treating or preventing a fungal infection. The compounds, compositions, and methods of the invention are also useful for inhibiting the growth of a fungus.

25 Claims, 10 Drawing Sheets

OTHER PUBLICATIONS

Nicolaou et al., 2001, Agnew Chem. Int. Ed. 40:207.

Nicolaou et al., 2001, "Selective Oxidation at Carbon Adjacent to Aromatic Systems with IBX," J. Am. Chem. Soc. 123:3183-3185.

Poigny et al., 1998, "Efficient Total Synthesis of (−)-Ilimaquinone," J. Org. Chem. 63:5890-5894.

Rosales et al., 2002, "Regioselective Palladium-Catalyzed Alkylation of Allylic Halides with Benzylic Grignard Reagents. Two-Step Synthesis of Abietane Terpenes and Tetracyclic Polyprenoid Compounds," J. Org. Chem. 67:1167-1170.

Shishido et al., 1994, "Synthetic studies on diterpenoid quinones with interleukin-1 inhibitory activity. Total synthesis of (.+.)- and (+)-triptoquinone A," J. Org. Chem. 59:406-414.

Snider et al., 1985, "Manganese(III)-based oxidative free-radical cyclization. Synthesis of (.+.)-podocarpic acid," J. Org. Chem. 50:3659-3661.

Takahashi et al., 1999, Syn. Lett. 5:6444-6446.

Taylor, 1977, "Thallium in organic synthesis. 47. Regioselective ring expansion of cyclic aralkyl ketones via wittig-derived olefins with thallium(III) nitrate(TTN)," Tetrahedron Lett. 18(21):1827-1830.

Thompson et al., 1976, "Stereochemical control of reductions. 5. Effects of electron density and solvent on group haptophilicity," J. Org. Chem. 41:2903-2906.

Tius et al., 1992, "A novel approach to the synthesis of morphine alkaloids: the synthesis of (d,l)-thebainone-A," J. Am. Chem. Soc. 114:5959-5966.

Welch et al., 1979, "A stereoselective total synthesis of (.+.)-gymnomitrol," J. Am. Chem. Soc. 101:6768-6769.

Woo et al., 2002, "A-ring analogues of oestrone 3-O-sulphamate as potent steroid sulphatase inhibitors and potential anti-cancer agents," Eur. J. Cancer 38(7):S125 Abstract 415.

Alder et al., 1953, "tert.-Butylbutadien and Acrylsaure (Ein Beitrag zur Kenntnis der Dien-Synthese mit unsymmetrischen Addenden*)," Chem. Ber. 86:1364-1371.

Barros, M.C.P. et al., 2003, "1H and 13C NMR assignments of abietane diterpenes from *Aegiphila lhotzkyana*," Mag. Res. in Chem. 41(9): 731-734.

Broka C.A. & Ruhland, B., 1992, "Synthetic studies on wortmannin and 11-desacetoxywortmannin," J. of Org. Chem. 57(18): 4888-4894.

Creemer, L.C. et al., 1996, "Synthesis and in Vitro Evaluation of New Wortmannin Esters: Potent Inhibitors of Phosphatidylinositol 3-Kinase," J. of Med. Chem. 39(25): 5021-5024.

Haefliger, W. et al., 1975, "Selective functionalization of wortmannin using furan ring masking," Helvetica Chimica Acta 1975; 58(6): 1620-1628.

Haefliger, W. & Hauser, D., 1975, "Induction of the corticoid side chain into wortmannin," Helvetica Chimica Acta 58(6): 1629-1633.

Kreiser, W. & Ulrich W., 1972, "B-ring-diosphenols derived from lanosterol. I," Justus Liebigs Annalen der Chemie. 761: 121-129.

Kreiser, W. & Ulrich, W., 1976, "B-ring diosphenols derived from lanosterol, IV. α-Oximino ketones," Justus Liebigs Annalen der Chemie. 7-8: 1214-1221.

MacMillan J. et al., 1972, "Absolute Stereochemistry of the fungal product, wortmannin," J. of the Chem. Soc., Chem. Comm.. 19:1063.

MacMillan J. et al., 1972, "Fungal Products. III. Structure of wortmannin and hydrolysis products," J. of Chemical Society, Perkins Transactions 1: Organic and Bio-Organic Chemistry (1972-1999). 22:2898-2903.

Mitzutani, T. et al., 2002 "Total synthesis of (±)-Wortmannin," Angewandte Chemie, Int. Ed. 41(24): 2680-2682.

Norman B.H. et al., 1996 "Studies on the Mechanism of Phosphatidylinositol 2-Kinase Inhibition by Wortmannin and Related Analogs," J. of Med. Chem.. 39(5): 1106-1111.

Pinto, A.C. et al., 1984, "Diterpenes with pimarane and cleistanthane skeletons from *Vellozia piresiana*," Phytochemistry (Elvesier) 123(6), 1293-1296.

Rodriguez, B., 2002, "Complete assignments of the 1H and 13C NMR spectra of five rearranged abietane diterpenoids," Mag. Res. in Chem. 40(11): 752-754.

Sexmero C. et al., 1992, "Rearranged abietane diterpenoids from the root of two Teucrium species," Phytochemistry 31(5): 1697-1701.

Silva G.C. et al., 2001, "Cleistanthane diterpenoids from Vellozia app. caruncullares Martius ex Seubert (velloziaceae)," Quim. Nova. 24(5): 619-625.

Wang A. H., et al., 1973, "Structure and absolute stereochemistry of the diterpenoid barbatusin" J. of Amer. Chem. Soc. 95(2): 598-600.

Yano, H. et al., 1993, "Inhibition of histamine secretion by Wortmannin through the blockade of phosphatidylinositol 3-kinase in RBL-2H3 cells," J. of Biol. Chem. 268(34): 25846-25856.

Zelnik, R. et al., 1997, "Barbatusin and cyclobutatusin, two novel diterpenoids from *Coleus barbatus* Bentham," Tetrahedron. 33(12): 1457-1467.

* cited by examiner

DITERPENOID COMPOUNDS, COMPOSITIONS THEREOF AND THEIR USE AS ANTI-CANCER OR ANTI-FUNGAL AGENTS

RELATED APPLICATIONS

This application claims the benefit of U.S. application Ser. No. 10/725,629, filed Dec. 1, 2003, which claims the benefit of U.S. provisional application Ser. No. 60/431,096, filed Dec. 5, 2002, the entire disclosures of which are incorporated by reference herein in their entireties.

1. FIELD OF THE INVENTION

The present invention relates to Diterpenoid Compounds, compositions comprising an effective amount of a Diterpenoid Compound, and methods useful for treating or preventing cancer or a neoplastic disorder comprising administering an effective amount of a Diterpenoid Compound. The compounds, compositions, and methods of the invention are also useful for inhibiting the growth of a cancer cell or neoplastic cell, or for inducing apoptosis in a cancer or neoplastic cell. The compounds, compositions, and methods of the invention are further useful for treating or preventing a fungal infection. The compounds, compositions, and methods of the invention are also useful for inhibiting the growth of a fungus.

2. BACKGROUND OF THE INVENTION

2.1 Cancer and Neoplastic Disease

Cancer affects approximately 20 million adults and children worldwide, and this year, more than 9 million new cases will be diagnosed (International Agency for Research on Cancer; www.irac.fr). According to the American Cancer Society, about 563,100 Americas are expected to die of cancer this year, more than 1500 people a day. Since 1990, in the United States alone, nearly five million lives have been lost to cancer, and approximately 12 million new cases have been diagnosed.

Currently, cancer therapy involves surgery, chemotherapy and/or radiation treatment or eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, can be contraindicated due to the health of the patient or can be unacceptable to the patient. Additionally, surgery might not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, traditional chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy can cause significant, and often dangerous, side effects, including severe nausea, bone marrow depression, immunosuppression, etc. Additionally, many tumor cells are resistant or develop resistance to chemotherapeutic agents through multi-drug resistance.

Therefore, there is a significant in the art for novel compounds and compositions, and methods that are useful for treating cancer or neoplastic disease with reduced or without the aforementioned side effects. Further, there is a need for cancer treatments that provide cancer-cell-specific therapies with increase specificity and decreased toxicity.

2.2 Fungal Infection and Related Health Issues

Fungi are eukaryotic microorganisms and can occur as yeast, molds, or as a combination of both forms. Some fungi are capable of causeing superficial, cutaneous, subcutaneous, systemic or allergic dieases. Yeast are microscopic fungi consisting of solitary cells that reproduce by budding. Molds, in contrast, occur in long filaments known as hyphae, which grow by apical extension.

Known fungal and mycotic pathogens include, but are not limited to, *Absidia* spp., *Actinomadura madurae*, *Actinomyces* spp., *Allescheria boydii*, *Alternaria* spp., *Anthopsis deltoidea*, *Apophysomyces elegans*, *Arnium leoporinum*, *Aspergillus* spp., *Aureobasidium pullulans*, *Basidiobolus ranarum*, *Bipolaris* spp., *Blastomyces dermatitidis*, *Candida* spp., *Cephalosporium* spp., *Chaetoconidium* spp., *Chaetomium* spp., *Cladosporium* spp., *Coccidioides immitis*, *Conidiobolus* spp., *Corynebacterium tenuis*, *Cryptococcus* spp., *Cunninghamella bertholletiae*, *Curvularia* spp., *Dactylaria* spp., *Epidermophyton* spp., *Epidermophyton floccosum*, *Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur*, *Microsporum* spp., *Mucor* spp., *Mycocentrospora acerina Nocardia* spp., *Paracoccidioides brasiliensis*, *Penicillium* spp., *Phaeosclera dematioides*, *Phaeoannellomyces* spp., *Phialemonium obovatum*, *Phialophora* spp., *Phoma* spp., *Piedraia hortai*, *Pneumocystis carinii*, *Pythium insidiosum*, *Rhinocladiella aquaspersa*, *Rhizomucor pusillus*, *Rhizopus* spp., *Saksenaea vasiformis*, *Sarcinomyces phaeomuriformis*, *Sporothrix schenckii*, *Syncephalastrum racemosum*, *Taeniolella boppii*, *Torulopsosis* spp., *Trichophyton* spp., *Trichosporon* spp., *Ulocladium chartarum*, *Wangiella dermatitidis*, and *Xylohypha* spp. Other fungi that might have pathogenic potential include, but are not limited to, *Thermomucor indicae-seudaticae*, *Radiomyces* spp., and other species of known pathogenic genera. There are also reports implicating *saccharomyces* as a human pathogen (e.g., Fungemia with saccharomycetacea, H. Nielson, J. Stenderup, & B. Bruun, Scand. J. Infect. Dis. 22:581–584, 1990). In recent years, there has been a marked increase in the number of serious mycoses as a result of the growing number of immunosuppressed and immunocompromised individuals, such as transplant recipients, patients receiving chemotherapy, and HIV-infected individuals, and thus greater attention has been devoted to the need to develop safer and more effective antifungal agents.

Fungal infection is also a significant problem in veterinary medicine and in agriculture. Products that are susceptible to fungal infestation include wood products, textiles, plastics, paper, rubber, adhesives, emulsion polymers, leather, cosmetics, household disinfectants, deodorants, and paint (C. C. Yeager, Fungicides in Industry, in *Antifungal Compounds*, M. Siegel and H. Sisler, eds., Marcel Dekker Inc., NY, 1977).

2.2.1 Current Therapies

The mechanism of action of four main classes of antifungal agents is summarized below:

Polyene Antifungal Drugs

Amphotericin, nystatin, and pimaricin interact with sterols in the cell membrane (ergosterol in fungi, cholesterol in humans) to form channels through which small molecules leak from the inside of the fungal cell to the outside.

Azole Antifungal Drugs

Fluconazole, itraconazole, and ketoconazole inhibit cytochrome P450-dependent enzymes (particularly C14-demethylase) involved in the biosynthesis of ergosterol, which is required for fungal cell membrane structure and function.

Allylamine and Morpholine Antifungal Drugs

Allylamines (naftifine, terbinafine) inhibit ergosterol biosynthesis at the level of squalene epoxidase. The morpholine drug amorolfine inhibits the same pathway at a later step.

Antimetabolite Antifungal Drugs

5-Fluorocytosine acts as an inhibitor of both DNA and RNA synthesis via the conversion of 5-fluorocytosine to 5-fluorouracil.

Many of the drugs currently available for treatment of mycoses have significant side effects or lack effectiveness against some important pathogens. For example, amphotericin B, an antifungal polyene macrolide antibiotic, has both short-term and long-term adverse effects, ranging from nausea and vomiting to kidney damage. Some evidence exists for the development of resistance to these drugs. There is therefore an ongoing need for novel antifungal drugs with few, if any, side effects and with effectiveness against pathogens for which current drugs are inadequate.

Citation of any reference in Section 2 of this application is not an admission that the reference is prior art to the application.

3. SUMMARY OF THE INVENTION

The present invention encompasses compounds having the Formula (Ia):

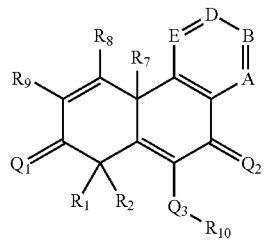

(Ia)

and pharmaceutically acceptable salts thereof, wherein:

$Q_1$ and $Q_2$ are independently =O, =S, =NOR, =NR, =N—NHR, or =N—N(R)$_2$ where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, —OH, -halogen, —CN, —NH$_2$, —NO$_2$, —COOH, —C(O)NH$_2$, —SH, —S(O)NH$_2$, —S(O)$_2$NH$_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein R$_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)NH$_2$, —C(O)NHR$_{12}$, —C(O)N(R$_{12}$)$_2$, P(O)(OR$_{13}$)$_2$, or -aryl, wherein R$_{10}$ is not P(O)(OR$_{13}$)$_2$ if Q$_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

each halogen is independently —F, —Cl, —Br or —I; and $R_{13}$ is H, $C_1$–$C_{10}$ alkyl, aryl, or benzyl.

In one embodiment, the compound of Formula (Ia) is not:

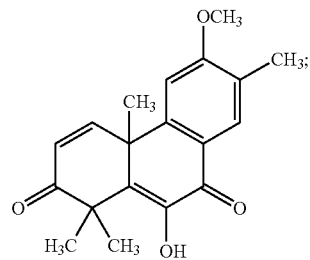
48

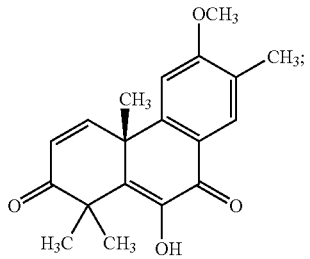
48a

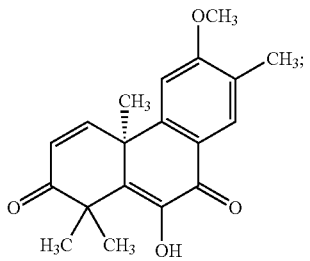
48b

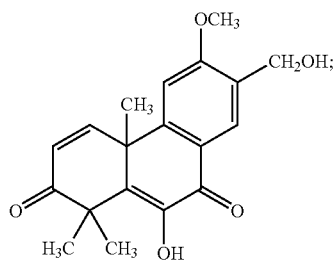
49

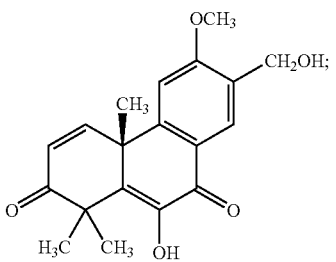
49a

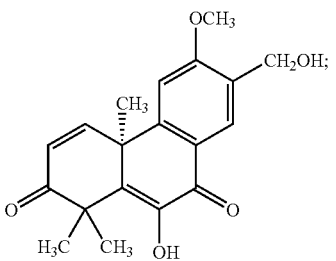
49b or a pharmaceutically acceptable salt thereof.

In certain, more specific embodiments, the invention provides compounds having the Formula (Ia), wherein if D is C—OH then $R_4$ is not —$CH_3$.

In certain, even more specific embodiments, the invention provides compounds having the Formula (Ia), wherein if (i) D is C—OH; (ii) $Q_1$ is =O; (iii) $Q_2$ is =O; (iv) A is CH; and (v) E is $CR_7$ then $R_4$ is not —$CH_3$.

The present invention further encompasses compounds having the Formula (Ib):

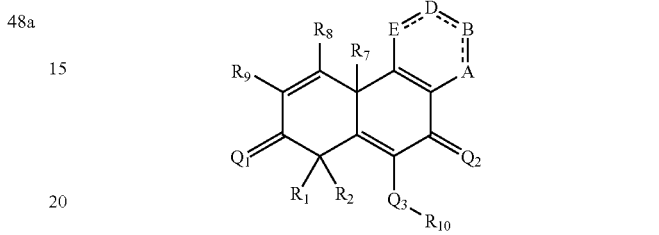
(Ib)

and pharmaceutically acceptable salts thereof, wherein:

a dashed line indicates that the bond between the atoms that are connected by the dashed line can be a single bond or a double bond;

the ring with positions A, B, D, and E is not aromatic;

$Q_1$ and $Q_2$ are independently =O, =S, =NOR, =NR, =N—NHR, or =N—N(R)$_2$ where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, =O, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, $C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —S(O)$_2NHR_{11}$, —$SOR_{11}$, —S(O)$_2R_{11}$, —NHC(O)$R_{11}$, —$NHSOR_{11}$, NHS(O)$_2R_{11}$, —OPO($OR_{15}$)$_2$, —O-arylPO($OR_{15}$)$_2$, or —O-alkylarylPO($OR_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —$OC(O)R_{11}$, —$C(O)R_{11}$, —$OC(O)OR_{11}$, —$OC(O)NR_{11}$, —$C(O)OR_{11}$, —$C(O)NR_{11}$, —$OP(O)(OR_{11})_2$, —$SR_{11}$, —$SOR_{11}$, —$S(O)_2R_{11}$, —$S(O)_2NHR_{11}$, —$NHSR_{11}$, —$NHSOR_{11}$, or —$NHS(O)_2R_{11}$;

$R_8$ is also —$S(CH_2)_n$amino acid, —$S(CH_2)_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —$C(O)C_1$–$C_{10}$ alkyl, —$C_1$–$C_{10}$ (oxy)alkyl, —$C(O)NH_2$, —$C(O)NHR_{12}$, —$C(O)N(R_{12})_2$, $P(O)(OR_{13})_2$, or -aryl, wherein $R_{10}$ is not $P(O)(OR_{13})_2$ if $Q_3$ is —N(H)— or —S—;

$R_{11}$, is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl; and each halogen is independently —F, —Cl, —Br or —I.

$R_{13}$ is H, $C_1$–$C_{10}$ alkyl, aryl, or benzyl.

Examplary positions of the doublebond in the ring with positions A, B, D and E are shown below:

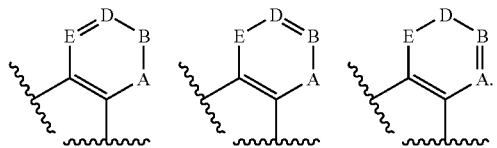

The present invention further encompasses compounds having the Formula (Ic):

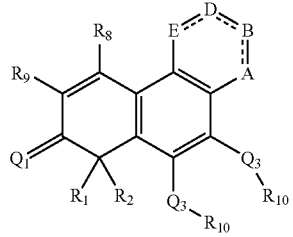

(Ic)

and pharmaceutically acceptable salts thereof, wherein:

a dashed line indicates that the bond between the atoms that are connected by the dashed line can be a single bond or a double bond (see Formula (Ib) above for exemplary positions of the doublebond);

$Q_1$ is =O, =S, =NOR, =NR, =N—NHR, or =N—N(R)$_2$ where R is —H, —$C_1$–$C_{10}$ alkyl, or -aryl;

$Q_3$ is at each occurance independently —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, =O, —OH, - halogen, —CN, —$NH_2$, —$NO_2$, —COOH, —$C(O)NH_2$, —SH, —$S(O)NH_2$, —$S(O)_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, - aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —$OC(O)R_{11}$, —$C(O)R_{11}$, —$OC(O)OR_{11}$, —$OC(O)NR_{11}$, —$C(O)OR_{11}$, —$C(O)NR_{11}$, —$OP(O)(OR_{11})_2$, —$SR_{11}$, —$S(O)_2NHR_{11}$, —$SOR_{11}$, —$S(O)_2R_{11}$, —$NHC(O)R_{11}$, —$NHSOR_{11}$, $NHS(O)_2R_{11}$, —$OPO(OR_{15})_2$, —O-arylPO(OR$_{15}$)$_2$, or —O-alkylarylPO(OR$_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —$C(O)NH_2$, —SH, —$S(O)NH_2$, —$S(O)_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —$OC(O)R_{11}$, —$C(O)R_{11}$, —$OC(O)OR_{11}$, —$OC(O)NR_{11}$, —$C(O)OR_{11}$, —$C(O)NR_{11}$, —$OP(O)(OR_{11})_2$, —$SR_{11}$, —$SOR_{11}$, —$S(O)_2R_{11}$, —$S(O)_2NHR_{11}$, —$NHSR_{11}$, —$NHSOR_{11}$, or —$NHS(O)_2R_{11}$;

$R_8$ is also —$S(CH_2)_n$amino acid, —$S(CH_2)_n$peptide, wherein n=0 to 4, wherein the amino acid is connected to the compound through its alpha carbon atom, and wherein the peptide is connected to the compound through the alpha carbon atom of one of its amino acids;

$R_{10}$ is at each occurance independently —H, —$C_1$–$C_{10}$ alkyl, —$C_3$–$C_7$ cycloalkyl, —$C(O)C_1$–$C_{10}$ alkyl, —$C_1$–$C_{10}$ (oxy)alkyl, —$C(O)NH_2$, —$C(O)NHR_{12}$, —$C(O)N(R_{12})_2$, $P(O)(OR_{13})_2$, or -aryl, wherein $R_{10}$ is not $P(O)(OR_{13})_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl; and each halogen is independently —F, —Cl, —Br or —I.

$R_{13}$ is H, $C_1$–$C_{10}$ alkyl, aryl, or benzyl.

In certain embodiments, the compound or a pharmaceutically acceptable salt of the compound of Formula (Ia), (Ib) or (Ic) is in isolated and purified form. It is recognized that the compound or a pharmaceutically acceptable salt of the compound of Formula (Ia), (Ib) or (Ic) in a composition, such as a pharmaceutical composition, is preferably in isolated and purified form. In a preferred embodiment, the compound or a pharmaceutically acceptable salt of the compound of Formula (Ia), (Ib) or (Ic) is in solid form.

The present invention still further provides compounds having the Formula (IIa):

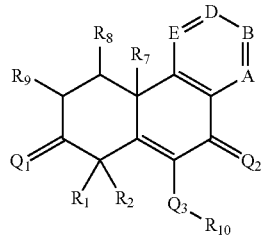

(IIa)

and pharmaceutically acceptable salts thereof, wherein:

$Q_1$ and $Q_2$ are independently =O, =S, =NOR, =NR, =N—NHR, or =N—N(R)$_2$, where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —S(O)$_2NHR_{11}$, —$SOR_{11}$, —S(O)$_2R_{11}$, —NHC(O)$R_{11}$, —$NHSOR_{11}$, $NHS(O)_2R_{11}$, —OPO($OR_{15}$)$_2$, —O-arylPO($OR_{15}$)$_2$, or —O-alkylarylPO($OR_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —$SOR_{11}$, —S(O)$_2R_{11}$, —S(O)$_2NHR_{11}$, —$NHSR_{11}$, —$NHSOR_{11}$, or —$NHS(O)_2R_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)$NH_2$, —C(O)$NHR_{12}$, —C(O)$N(R_{12})_2$, P(O)($OR_{13}$)$_2$, or -aryl, wherein $R_{10}$ is not P(O)($OR_{13}$)$_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

each halogen is independently —F, —Cl, —Br or —I; and $R_{13}$ is H, $C_1$–$C_{10}$ alkyl, aryl, or benzyl.

In certain, more specific embodiments, the invention provides compounds having the Formula (IIa), wherein if D is C—OH then $R_4$ is not —CH$_3$ and if E is C—OH then A is not C—OH.

In certain, even more specific embodiments, the invention provides compounds having the Formula (IIa), wherein (a) if (i) D is C—OH, (ii) $Q_1$ is =O, (iii) $Q_2$ is =O, (iv) A is CH$_2$, and (v) E is $CR_7$ then $R_4$ is not —CH$_3$; and (b) if (i) E is C—OH, (ii) $Q_1$ is =O, (iii) $Q_2$ is =O, (iv) $R_{10}$ is H, (v) B is $CR_4$, (vi) D is $CR_5$, (vii) $R_7$ is CH$_3$, and (viii) $Q_3$ is —O— then A is not C—OH.

The present invention still further provides compounds having the Formula (IIb):

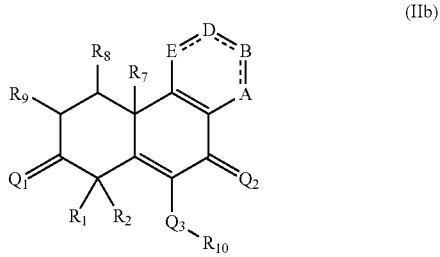

(IIb)

and pharmaceutically acceptable salts thereof, wherein:

a dashed line indicates that the bond between the atoms that are connected by the dashed line can be a single bond or a double bond (see Formula (Ib) above for exemplary positions of the doublebond);

the ring with positions A, B, D, and E is not aromatic;

$Q_1$ and $Q_2$ are independently =O, =S, =NOR, =NR, =N—NHR, or =N—N(R)$_2$, where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, =O, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —S(O)$_2NHR_{11}$, —$SOR_{11}$, —S(O)$_2R_{11}$, —NHC(O)$R_{11}$, —$NHSOR_{11}$, $NHS(O)_2R_{11}$, —OPO($OR_{15}$)$_2$, —O-arylPO($OR_{15}$)$_2$, or —O-alkylarylPO($OR_{15}$)$_2$ wherein $R_{15}$ is H, —$C_1$–$C_{10}$ alkyl, $C_7$–$C_{12}$arylalkyl, $C_1$–$C_{10}$ aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —$SOR_{11}$, —S(O)$_2R_{11}$, —S(O)$_2NHR_{11}$, —$NHSR_{11}$, —$NHSOR_{11}$, or —$NHS(O)_2R_{11}$;

$R_8$ is also —S($CH_2$)$_n$amino acid, —S($CH_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)$NH_2$, —C(O)$NHR_{12}$, —C(O)N($R_{12}$)$_2$, P(O)($OR_{13}$)$_2$, or -aryl, wherein $R_{10}$ is not P(O)($OR_{13}$)$_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

each halogen is independently —F, —Cl, —Br or —I; and $R_{13}$ is H, $C_1$–$C_{10}$ alkyl, aryl, or benzyl.

The present invention still further provides compounds having the Formula (IIc):

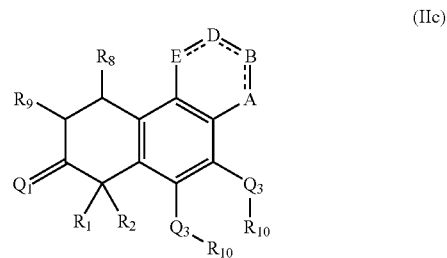

(IIc)

and pharmaceutically acceptable salts thereof, wherein:

a dashed line indicates that the bond between the atoms that are connected by the dashed line can be a single bond or a double bond (see Formula (Ib) above for exemplary positions of the doublebond);

$Q_1$ is =O, =S, =NOR, =NR, =N—NHR, or =N—N(R)$_2$, where R is —H, —$C_1$–$C_{10}$ alkyl, or -aryl;

$Q_3$ is at each occurance independently —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, =O, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —S(O)$_2NHR_{11}$, —$SOR_{11}$, —S(O)$_2R_{11}$, —NHC(O)$R_{11}$, —$NHSOR_{11}$, $NHS(O)_2R_{11}$, —OPO($OR_{15}$)$_2$, —O-arylPO($OR_{15}$)$_2$, or —O-alkylarylPO($OR_{15}$)$_2$ wherein $R_{15}$ is H, —$C_1$–$C_{10}$ alkyl, $C_7$–$C_{12}$arylalkyl, $C_1$–$C_{10}$ aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{10}$ is at each occurance independently —H, —C$_1$–C$_{10}$ alkyl, —C$_3$–C$_7$ cycloalkyl, —C(O)C$_1$–C$_{10}$ alkyl, —C$_1$–C$_{10}$ (oxy)alkyl, —C(O)NH$_2$, —C(O)NHR$_{12}$, —C(O)N(R$_{12}$)$_2$, P(O)(OR$_{13}$)$_2$, or -aryl, wherein R$_{10}$ is not P(O)(OR$_{13}$)$_2$ if Q$_3$ is —N(H)— or —S—;

R$_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

R$_{12}$ is C$_1$–C$_{10}$ alkyl;

each halogen is independently —F, —Cl, —Br or —I; and

R$_{13}$ is H, C$_1$–C$_{10}$ alkyl, aryl, or benzyl.

In certain embodiments, the compound or a pharmaceutically acceptable salt of the compound of Formula (IIa), (IIb) or (IIc) is in isolated and purified form. It is recognized that the compound or a pharmaceutically acceptable salt of the compound of Formula (IIa), (IIb) or (IIc) in a composition, such as a pharmaceutical composition, is preferably in isolated and purified form. In a preferred embodiment, the compound or a pharmaceutically acceptable salt of the compound of Formula (IIa), (IIb) or (IIc) is in solid form.

The present invention still further provides compounds having the Formula (IIIa):

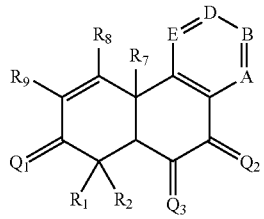

(IIIa)

and pharmaceutically acceptable salts thereof, wherein:

Q$_1$, Q$_2$ and Q$_3$ are independently =O, =S, =NOR, =NR, =N—NHR, or =N—N(R)$_2$, where R is —H, —C$_1$–C$_{10}$ alkyl, or -aryl;

R$_1$ and R$_2$ are independently —H, -halogen, -amino, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or R$_1$, R$_2$ and the carbon atom to which they are both attached are taken together to form a (C$_3$–C$_7$) cycloalkyl group or a three- to seven-membered non-aromatic heterocycle;

A is N or CR$_3$; B is N or CR$_4$; D is N or CR$_5$; E is N or CR$_6$, at least one of A, B, D and E being CR$_3$, CR$_4$, CR$_5$ or CR$_6$, respectively;

each R$_3$, R$_4$, R$_5$ and R$_6$ is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

R$_7$ is —H, —C$_1$–C$_{10}$ alkyl, or —C$_1$–C$_{10}$ alkoxy;

R$_8$ and R$_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{11}$, is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

R$_{12}$ is C$_1$–C$_{10}$ alkyl; and each halogen is independently —F, —Cl, —Br or —I.

The present invention still further provides compounds having the Formula (IIIb):

(IIIb)

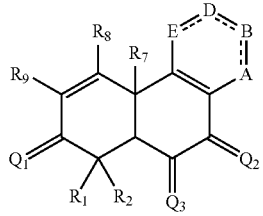

and pharmaceutically acceptable salts thereof, wherein:

a dashed line indicates that the bond between the atoms that are connected by the dashed line can be a single bond or a double bond (see Formula (Ib) above for exemplary positions of the doublebond);

the ring with positions A, B, D, and E is not aromatic;

$Q_1$, $Q_2$ and $Q_3$ are independently =O, =S, =NOR, =NR, =N—NHR, or =N—N(R)$_2$, where R is —H, —$C_1$–$C_{10}$ alkyl, or -aryl;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, —OH, =O, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)O$R_{11}$, —OC(O)N$R_{11}$, —C(O)O$R_{11}$, —C(O)N$R_{11}$, —OP(O)(O$R_{11}$)$_2$, —S$R_{11}$, —S(O)$_2$NH$R_{11}$, —SO$R_{11}$, —S(O)$_2R_{11}$, —NHC(O)$R_{11}$, —NHSO$R_{11}$, NHS(O)$_2R_{11}$, —OPO(O$R_{15}$)$_2$, —O-arylPO(O$R_{15}$)$_2$, or —O-alkylarylPO(O$R_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —OCR$_{11}$, —OC(O)$R_{11}$, —C(O)$R_{11}$, —OC(O)O$R_{11}$, —OC(O)NR$_{11}$, —C(O)O$R_{11}$, —C(O)NR$_{11}$, —OP(O)(O$R_{11}$)$_2$, —S$R_{11}$, —SO$R_{11}$, —S(O)$_2R_{11}$, —S(O)$_2$NH$R_{11}$, —NHS$R_{11}$, —NHSO$R_{11}$, or —NHS(O)$_2R_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl; and each halogen is independently —F, —Cl, —Br or —I.

In certain embodiments, the compound or a pharmaceutically acceptable salt of the compound of Formula (IIIa) or (IIIb) is in isolated and purified form. It is recognized that the compound or a pharmaceutically acceptable salt of the compound of Formula (IIIa) or (IIIb) in a composition, such as a pharmaceutical composition, is preferably in isolated and purified form. In a preferred embodiment, the compound or a pharmaceutically acceptable salt of the compound of Formula (IIIa) or (IIIb) is in solid form.

The present invention encompasses compounds having the Formula (IVa):

(IVa)

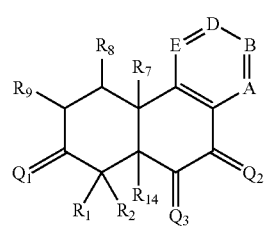

and pharmaceutically acceptable salts thereof, wherein:

$Q_1$, $Q_2$ and $Q_3$ are independently =O, =S, =NOR, =NR, =N—NHR, or =N—N(R)$_2$, where R is —H, —$C_1$–$C_{10}$ alkyl, or -aryl;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)O$R_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

R$_7$ is —H, —C$_1$–C$_{10}$ alkyl, or —C$_1$–C$_{10}$ alkoxy;

R$_8$ and R$_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

R$_{12}$ is C$_1$–C$_{10}$ alkyl;

R$_{14}$ is —H, —OH, or halogen, and each halogen is independently —F, —Cl, —Br or —I.

In certain, more specific embodiments, the invention provides a compound of Formula (IVa), wherein R$_{14}$ is —H.

The present invention encompasses compounds having the Formula (IVb):

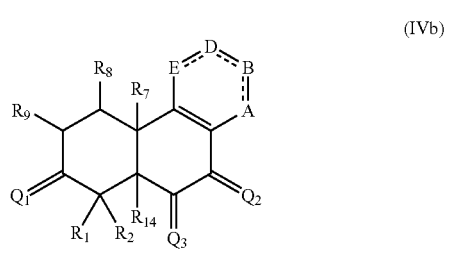

(IVb)

and pharmaceutically acceptable salts thereof, wherein:

a dashed line indicates that the bond between the atoms that are connected by the dashed line can be a single bond or a double bond (see Formula (Ib) above for exemplary positions of the doublebond);

the ring with positions A, B, D, and E is not aromatic;

Q$_1$, Q$_2$ and Q$_3$ are independently =O, =S, =NOR, =NR, =N—NHR, or =N—N(R)$_2$, where R is —H, —C$_1$–C$_{10}$ alkyl, or -aryl;

R$_1$ and R$_2$ are independently —H, -halogen, -amino, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or R$_1$, R$_2$ and the carbon atom to which they are both attached are taken together to form a (C$_3$–C$_7$) cycloalkyl group or a three- to seven-membered non-aromatic heterocycle;

A is N or CR$_3$; B is N or CR$_4$; D is N or CR$_5$; E is N or CR$_6$, at least one of A, B, D and E being CR$_3$, CR$_4$, CR$_5$ or CR$_6$, respectively;

each R$_3$, R$_4$, R$_5$ and R$_6$ is independently —H, —OH, =O, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR, , —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

R$_7$ is —H, —C$_1$–C$_{10}$ alkyl, or —C$_1$–C$_{10}$ alkoxy;

R$_8$ and R$_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

R$_{12}$ is C$_1$–C$_{10}$ alkyl;

R$_{14}$ is —H, —OH, or halogen, and each halogen is independently —F, —Cl, —Br or —I.

In certain, more specific embodiments, the invention provides a compound of Formula (IVb), wherein R$_{14}$ is —H.

In certain embodiments, the compound or a pharmaceutically acceptable salt of the compound of Formula (IVa) or (IVb) is in isolated and purified form. It is recognized that the compound or a pharmaceutically acceptable salt of the compound of Formula (IVa) or (IVb) in a composition, such as a pharmaceutical composition, is preferably in isolated and purified form. In a preferred embodiment, the compound or a pharmaceutically acceptable salt of the compound of Formula (IVa) or (IVb) is in solid form.

The present invention still further provides compounds having the Formula (Va):

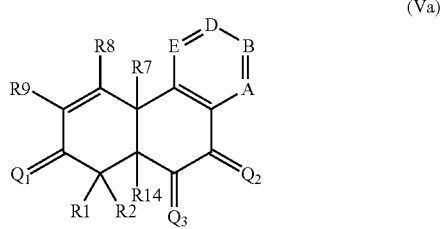

(Va)

and pharmaceutically acceptable salts thereof, wherein:

$Q_1$, $Q_2$ and $Q_3$ are independently =O, =S, =NR, =NOR, =N—NHR, or =N—N(R)$_2$ where R is —H, —C$_1$–C$_{10}$ alkyl, or -aryl;

$R_1$ and $R_2$ are independently —H, -halogen, -amino, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is N or CR$_3$; B is N or CR$_4$; D is N or CR$_5$; E is N or CR$_6$, at least one of A, B, D and E being CR$_3$, CR$_4$, CR$_5$ or CR$_6$, respectively;

each $R_3$, $R_4$, $R_5$ and $R_6$ is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

R$_7$ is —H, —C$_1$–C$_{10}$ alkyl, or —C$_1$–C$_{10}$ alkoxy;

R$_8$ and R$_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_1$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

R$_{12}$ is C$_1$–C$_{10}$ alkyl;

R$_{14}$ is —H, —OH, or halogen; and each halogen is independently —F, —Cl, —Br or —I.

The present invention still further provides compounds having the Formula (Vb):

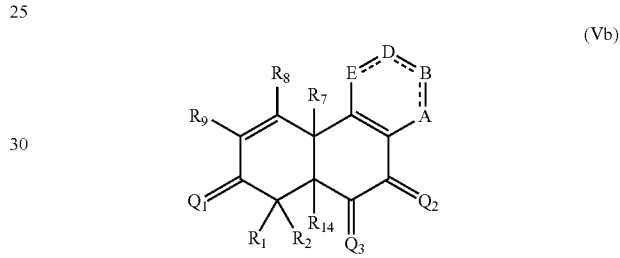

(Vb)

and pharmaceutically acceptable salts thereof, wherein:

a dashed line indicates that the bond between the atoms that are connected by the dashed line can be a single bond or a double bond (see Formula (Ib) above for exemplary positions of the doublebond);

the ring with positions A, B, D, and E is not aromatic;

$Q_1$, $Q_2$ and $Q_3$ are independently =O, =S, =NR, =NOR, =N—NHR, or =N—N(R)$_2$ where R is —H, —C$_1$–C$_{10}$ alkyl, or -aryl;

$R_1$ and $R_2$ are independently —H, -halogen, -amino, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is N or CR$_3$; B is N or CR$_4$; D is N or CR$_5$; E is N or CR$_6$, at least one of A, B, D and E being CR$_3$, CR$_4$, CR$_5$ or CR$_6$, respectively;

each $R_3$, $R_4$, $R_5$ and $R_6$ is independently —H, —OH, =O, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO (OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

R$_7$ is —H, —C$_1$–C$_{10}$ alkyl, or —C$_1$–C$_{10}$ alkoxy;

R$_8$ and R$_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

R$_{12}$ is C$_1$–C$_{10}$ alkyl;

R$_{14}$ is —H, —OH, or halogen; and each halogen is independently —F, —Cl, —Br or —I.

In certain embodiments, the compound or a pharmaceutically acceptable salt of the compound of Formula (Va) or (Vb) is in isolated and purified form. It is recognized that the compound or a pharmaceutically acceptable salt of the compound of Formula (Va) or (Vb) in a composition, such as a pharmaceutical composition, is preferably in isolated and purified form. In a preferred embodiment, the compound or a pharmaceutically acceptable salt of the compound of Formula (Va) or (Vb) is in solid form.

The present invention still further provides compounds having the Formula (VIa):

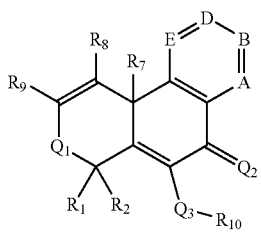
(VIa)

and pharmaceutically acceptable salts thereof, wherein:

Q$_1$ is CHOH, CH2, CHOR, where R is C$_1$–C$_{10}$ alkyl, aryl, —CH$_2$OR$_{11}$, —C(O)R$_{11}$, —C(O)OR$_{11}$, —C(O)OR$_{11}$, —C(O)NR$_{11}$, —P(O)(OR$_{11}$)$_2$ Q$_2$ is =O, =S, =NR, =NOR, =N—NHR, or =N—N (R)$_2$ where R is —H, —C$_1$–C$_{10}$ alkyl, or -aryl;

Q$_3$ is —O—, —S—, or —N(H)—;

R$_1$ and R$_2$ are independently —H, -halogen, -amino, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or R$_1$, R$_2$ and the carbon atom to which they are both attached are taken together to form a (C$_3$–C$_7$) cycloalkyl group or a three- to seven-membered non-aromatic heterocycle;

A is N or CR$_3$; B is N or CR$_4$; D is N or CR$_5$; E is N or CR$_6$, at least one of A, B, D and E being CR$_3$, CR$_4$, CR$_5$ or CR$_6$, respectively;

each R$_3$, R$_4$, R$_5$ and R$_6$ is independently —H, —OH, -halogen, —CN, —NH$_2$, —NO$_2$, —COOH, —C(O) NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO (OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

R$_7$ is —H, —C$_1$–C$_{10}$ alkyl, or —C$_1$–C$_{10}$ alkoxy;

R$_8$ and R$_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O) OR$_{11}$, —OC(O)NR$_{11}$, —C(O)OR$_{11}$, —C(O)NR$_{11}$, —OP(O) (OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{10}$ is —H, —C$_1$–C$_{10}$ alkyl, —C$_3$–C$_7$ cycloalkyl, —C(O) C$_1$–C$_{10}$ alkyl, —C$_1$–C$_{10}$ (oxy)alkyl, —C(O)NH$_2$, —C(O) NHR$_{12}$, —C(O)N(R$_{12}$)$_2$, P(O)(OR$_{13}$)$_2$, or -aryl, wherein R$_{10}$ is not P(O)(OR$_{13}$)$_2$ if Q$_3$ is —N(H)— or —S—;

R$_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

$R_{13}$ is H, $C_1$–$C_{10}$ alkyl, aryl, or benzyl; and each halogen is independently —F, —Cl, —Br or —I.

The present invention still further provides compounds having the Formula (VIb):

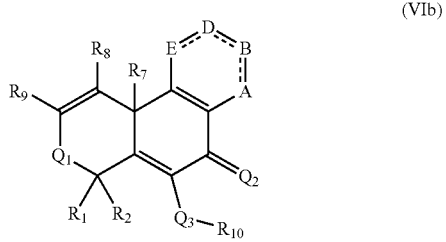

(VIb)

and pharmaceutically acceptable salts thereof, wherein:

a dashed line indicates that the bond between the atoms that are connected by the dashed line can be a single bond or a double bond (see Formula (Ib) above for exemplary positions of the doublebond);

the ring with positions A, B, D, and E is not aromatic;

$Q_1$ is CHOH, CH2, CHOR, where R is $C_1$–$C_{10}$ alkyl, aryl, —$CH_2OR_{11}$, —$C(O)R_{11}$, —$C(O)OR_{11}$, —$C(O)OR_{11}$, —$C(O)NR_{11}$, —$P(O)(OR_{11})_2$ $Q_2$ is =O, =S, =NR, =NOR, =N—NHR, or =N—N(R)$_2$ where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, —OH, =O, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —$OC(O)R_{11}$, —$C(O)R_{11}$, —$OC(O)OR_{11}$, —$OC(O)NR_{11}$, —$C(O)OR_{11}$, —$C(O)NR_{11}$, —$OP(O)(OR_{11})_2$, —$SR_{11}$, —$S(O)_2NHR_{11}$, —$SOR_{11}$, —$S(O)_2R_{11}$, —$NHC(O)R_{11}$, —$NHSOR_{11}$, $NHS(O)_2R_{11}$, —$OPO(OR_{15})_2$, —O-arylPO$(OR_{15})_2$, or —O-alkylarylPO$(OR_{15})_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —$OC(O)R_{11}$, —$C(O)R_{11}$, —$OC(O)OR_{11}$, —$OC(O)NR_{11}$, —$C(O)OR_{11}$, —$C(O)NR_{11}$, —$OP(O)(OR_{11})_2$, —$SR_{11}$, —$SOR_{11}$, —$S(O)_2R_{11}$, —$S(O)_2NHR_{11}$, —$NHSR_{11}$, —$NHSOR_{11}$, or —$NHS(O)_2R_{11}$;

$R_8$ is also —$S(CH_2)_n$amino acid, —$S(CH_2)_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)$NH_2$, —C(O)$NHR_{12}$, —C(O)$N(R_{12})_2$, $P(O)(OR_{13})_2$, or -aryl, wherein $R_{10}$ is not $P(O)(OR_{13})_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

$R_{13}$ is H, $C_1$–$C_{10}$ alkyl, aryl, or benzyl; and each halogen is independently —F, —Cl, —Br or —I.

In certain embodiments, the compound or a pharmaceutically acceptable salt of the compound of Formula (VIa) or (VIb) is in isolated and purified form. It is recognized that the compound or a pharmaceutically acceptable salt of the compound of Formula (VIa) or (VIb) in a composition, such as a pharmaceutical composition, is preferably in isolated and purified form. In a preferred embodiment, the compound or a pharmaceutically acceptable salt of the compound of Formula (VIa) or (VIb) is in solid form.

The present invention still further provides compounds having the Formula (VIIa):

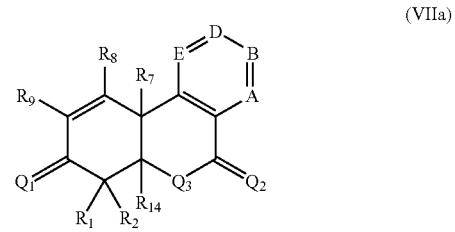

(VIIa)

$Q_1$ and $Q_2$ are independently =O, =S, =NR, =NOR, =N—NHR, or =N—N(R)$_2$ where R is —H, —$C_1$–$C_{10}$ alkyl, or -aryl;

$Q_3$ is CHOH, CH2, CHOR where R is $C_1$–$C_{10}$ alkyl, aryl, —$CH_2OR_{11}$, —$C(O)R_{11}$, —$C(O)OR_{11}$, —$C(O)NR_{11}$, or —$P(O)(OR_{11})_2$ $R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$)

cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —S(O)$_2NHR_{11}$, —$SOR_{11}$, —S(O)$_2R_{11}$, —NHC(O)$R_{11}$, —$NHSOR_{11}$, $NHS(O)_2R_{11}$, —OPO($OR_{15}$)$_2$, —O-arylPO($OR_{15}$)$_2$, or —O-alkylarylPO($OR_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —$SOR_{11}$, —S(O)$_2R_{11}$, —S(O)$_2NHR_{11}$, —$NHSR_{11}$, —$NHSOR_{11}$, or —NHS(O)$_2R_{11}$;

$R_8$ is also —S($CH_2$)$_n$amino acid, —S($CH_2$)$_n$peptide, wherein n=0 to 4, wherein the amino acid is connected to the compound through its alpha carbon atom, and wherein the peptide is connected to the compound through the alpha carbon atom of one of its amino acids;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

$R_{14}$ is —H, —OH, or halogen, and each halogen is independently —F, —Cl, —Br or —I.

In certain, more specific embodiments, the invention provides a compound of Formula (VIIa), wherein $R_{14}$ is —H.

In certain, more specific embodiments, the invention provides compounds having the Formula (VIIa), wherein if D is C—OH then $R_4$ is not —$CH_3$ and if B is C—$CH_3$ then $R_3$ is not ethyl. In certain, even more specific embodiments, the invention provides compounds having the Formula (VIIa), wherein (a) if (i) D is C—OH, (ii) $Q_1$ is =O, (iii) $Q_2$ is =O, (iv) A is CH, and (v) E is $CR_7$ then $R_4$ is not —$CH_3$; and (b) if (i) B is C—$CH_3$, (ii) $Q_1$ is =O, (iii) $Q_2$ is =O, (iv) $R_1$ is $CH_3$, (v) $R_2$ is $CH_3$, (vi) $R_7$ is methyl, (vii) D is CH, and (viii) E is CH then $R_3$ is not ethyl.

The present invention still further provides compounds having the Formula (VIIb):

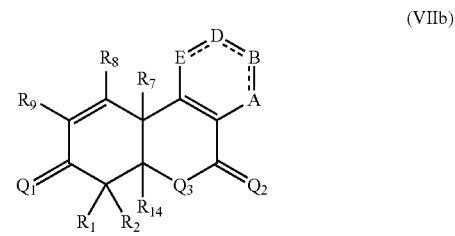

(VIIb)

or pharmaceutically acceptable salts thereof, wehrein, a dashed line indicates that the bond between the atoms that are connected by the dashed line can be a single bond or a double bond (see Formula (Ib) above for exemplary positions of the doublebond);

the ring with positions A, B, D, and E is not aromatic;

$Q_1$ and $Q_2$ are independently =O, =S, =NR, =NOR, =N—NHR, or =N—N(R)$_2$ where R is —H, —$C_1$–$C_{10}$ alkyl, or -aryl;

$Q_3$ is CHOH, CH2, CHOR where R is $C_1$–$C_{10}$ alkyl, aryl, —$CH_2OR_{11}$, —C(O)R, —C(O)$OR_{11}$, —C(O)$OR_{11}$, —C(O)$NR_{11}$ or —P(O)($OR_{11}$)$_2$ $R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is N or $CR_3$; B is N or $CR_4$; D is N or $CR_5$; E is N or $CR_6$, at least one of A, B, D and E being $CR_3$, $CR_4$, $CR_5$ or $CR_6$, respectively;

each $R_3$, $R_4$, $R_5$ and $R_6$ is independently —H, —OH, =O, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, $C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)($OR_{11}$)$_2$, —$SR_{11}$, —S(O)$_2NHR_{11}$, —$SOR_{11}$, —S(O)$_2R_{11}$, —NHC(O)$R_{11}$, —$NHSOR_{11}$, $NHS(O)_2R_{11}$, —OPO($OR_{15}$)$_2$, —O-arylPO($OR_{15}$)$_2$, or —O-alkylarylPO($OR_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

R$_{12}$ is C$_1$–C$_{10}$ alkyl;

R$_{14}$ is —H, —OH, or halogen, and each halogen is independently —F, —Cl, —Br or —I.

In certain, more specific embodiments, the invention provides a compound of Formula (VIIb), wherein R$_{14}$ is —H.

In certain embodiments, the compound or a pharmaceutically acceptable salt of the compound of Formula (VIIa) or (VIIb) is in isolated and purified form. It is recognized that the compound or a pharmaceutically acceptable salt of the compound of Formula (VIIa) or (VIIb) in a composition, such as a pharmaceutical composition, is preferably in isolated and purified form. In a preferred embodiment, the compound or a pharmaceutically acceptable salt of the compound of Formula (VIIa) or (VIIb) is in solid form.

A compound of Formula (Ia), (Ib), (Ic), Formula (IIa), (IIb), (IIc), Formula (IIIa), (IIIb), Formula (IVa), (IVb), Formula (Va), (Vb), Formula (VIa), (VIb), Formula (VIIa), (VIIb) or a pharmaceutically acceptable salt thereof (a "Diterpenoid Compound") is useful for treating or preventing cancer, a neoplastic disease or a fungal infection in a patient in need of such treatment or prevention. A Diterpenoid Compound is also useful for inhibiting the growth of a cancer cell, neoplastic cell or fungus. A Diterpenoid Compound is also useful for inducing cytotoxicity, e.g., through apoptosis, in a cancer cell or a neoplastic cell.

The present invention provides compositions comprising a pharmaceutically acceptable carrier and an effective amount of a Diterpenoid Compound. The compositions are useful for treating or preventing cancer, neoplastic disease or a fungal infection in a patient in need of such treatment or prevention. These compositions are also useful for inhibiting the growth of a cancer cell, neoplastic cell or fungus. These compositions are further useful for inducing cytotoxicity, e.g., through apoptosis, in a cancer cell or a neoplastic cell.

The invention further provides methods for treating or preventing cancer or a neoplastic disease, comprising administering to a patient in need of such treatment or prevention an effective amount of a Diterpenoid Compound.

The invention further provides methods for inhibiting the growth of a cancer cell or neoplastic cell, comprising contacting the cancer cell or neoplastic cell with an effective amount of a Diterpenoid Compound.

The invention further provides methods for inducing cytotoxicity, e.g., through apoptosis, in a cancer cell or neoplastic cell comprising contacting a cancer cell or neoplastic cell with an effective amount of a Diterpenoid Compound.

The invention further provides methods for inducing apoptosis in a cancer cell or neoplastic cell, comprising contacting a cancer cell or neoplastic cell capable of undergoing apoptosis with an effective amount of a Diterpenoid Compound.

In one embodiment, the Diterpenoid Compound is in isolated and purified form.

The invention further provides methods for treating or preventing a fungal infection, comprising administering to a patient in need of such treatment or prevention an effective amount of a Diterpenoid Compound.

The invention further provides methods for inhibiting the growth of a fungus, comprising contacting the fungus with an effective amount of a Diterpenoid Compound.

4. BRIEF DESCRIPTION OF THE DRAWINGS

Figure 1A:
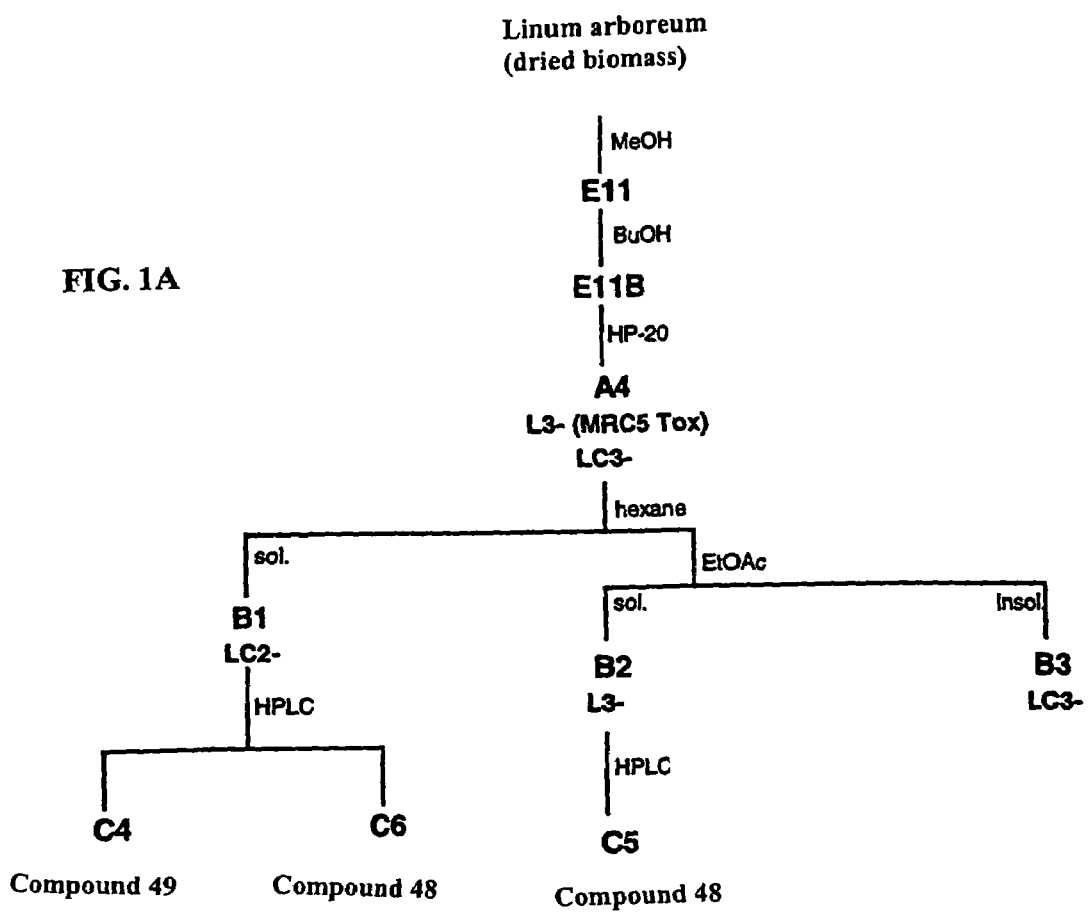
FIG. 1A is an isolation scheme for the isolation of Compounds 48 and 49 from dried biomass of *Linum arboreum*.

5. DETAILED DESCRIPTION OF THE INVENTION 5.1 Definitions and Abbreviations

As used herein, the term "C$_1$–C$_{10}$ alkyl" means a saturated straight chain or branched non-cyclic hydrocarbon having from 1 to 10 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, -2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

As used herein, the term "$C_1$–$C_{10}$ alkoxy" means —O— ($C_1$–$C_{10}$ alkyl), wherein $C_1$–$C_{10}$ alkyl is defined above.

As used herein, the term "$C_1$–$C_{10}$ (hydroxy)alkyl" means $C_1$–$C_{10}$ alkyl, wherein $C_1$–$C_{10}$ alkyl is defined above, substituted with one or more —OH groups. Examples of $C_1$–$C_{10}$ (hydroxy)alkyl include, but are not limited to, hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl and the like.

As used herein, the term "amino acid" means any naturally occurring amino acids and non-naturally occurring amino acids such as D-amino acids. For structures of amino acids, see, e.g., L. Stryer, Biochemistry, W.H. Freeman and Company, New York. An amino acid can be substituted with a protecting group. Suitable protecting groups for amino and amido groups include acetyl, tert-butoxy-C(O)—, benzyloxy-C(O)—, and the like. Suitable protecting groups for hydroxy include benzyl and the like. Suitable protecting groups for carboxy moieties include benzyl, tert-butyl, and the like. Other suitable protecting groups are well known to those of ordinary skill in the art and include those found in T. W. Greene, Protecting Groups in Organic Synthesis, John Wiley & Sons, Inc. 1981.

As used herein, the term "$C_1$–$C_{10}$ (amino)alkyl" means $C_1$–$C_{10}$ alkyl, wherein $C_1$–$C_{10}$ alkyl is defined above, substituted with one or more —$NH_2$ groups. Examples of $C_1$–$C_{10}$ (amino)alkyl include, but are not limited to, —$CH_2$—$NH_2$, —$(CH_2)_2$—$NH_2$, —$(CH_2)_3$—$NH_2$, —$(CH_2)_4$—$NH_2$, —$(CH_2)_5$—$NH_2$ and the like.

As used herein, the term "$C_1$–$C_{10}$ (halo)alkyl" means $C_1$–$C_{10}$ alkyl, wherein $C_1$–$C_{10}$ alkyl is defined above, substituted with one or more —F, —Cl, Br or —I groups. Examples of $C_1$–$C_{10}$ (halo)alkyl include, but are not limited to, trichloromethyl, trifluoromethyl, dichloromethyl, difluoromethyl, 1-fluoroethyl, 2-chloroethyl, 1-bromopropyl, 2-iodopropyl, 3-chloropropyl, 4-fluorobutyl, 5-chloropentyl and the like.

As used herein, the term "$C_2$–$C_{10}$ alkenyl" means a straight chain or branched non-cyclic hydrocarbon having from 2 to 10 carbon atoms and including at least one carbon-carbon double bond. Representative straight chain and branched $C_2$–$C_{10}$ alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. In one embodiment, $C_2$–$C_6$ alkenyl is a subclass of $C_2$–$C_{10}$ alkenyl. The double bond of a $C_2$–$C_{10}$ alkenyl can be unconjugated or conjugated to another unsaturated group. A —$C_2$–$C_{10}$ alkenyl can be unsubstituted or substituted with, e.g., -amino, —$C_1$–$C_{10}$ (oxy)alkyl, -halogen, —COOH, —C(O)$C_1$–$C_9$ alkyl, —SH, =S, —OH, and —$C_1$–$C_{10}$ alkoxy.

As used herein, unless otherwise specified the term "$C_2$–$C_{10}$ alkynyl" means a straight chain or branched non-cyclic hydrocarbon having from 2–10 carbon atoms and including at lease one carbon-carbon triple bond. Representative straight chain and branched $C_2$–$C_{10}$ alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. In one embodiment, $C_2$–$C_6$ alkynyl is a subclass of $C_2$–$C_{10}$ alkynyl. The triple bond of a $C_2$–$C_{10}$ alkynyl can be unconjugated or conjugated to another unsaturated group. A $C_2$–$C_{10}$ alkynyl can be unsubstituted or substituted with, e.g., -amino, —COOH, -halogen, $C_1$–$C_{10}$(oxy)alkyl, —C(O)$C_1$–$C_9$ alkyl, —SH, =S, —OH, $C_1$–$C_{10}$ alkoxy, and $C_1$–$C_{10}$ alkyl.

As used herein, the term "($C_3$–$C_7$) cycloalkyl" means a monocyclic or bicyclic saturated ring consisting of carbon and hydrogen atoms and having 3–7 carbon atoms. A ($C_3$–$C_7$) cycloalkyl can be unsubstituted or substituted with, e.g., -amino, —COOH, -halogen, $C_1$–$C_{10}$ (oxy)alkyl, —C(O)$C_1$–$C_9$ alkyl, —SH, =S, —OH, $C_1$–$C_{10}$ alkoxy, and $C_1$–$C_{10}$ alkyl. Examples of ($C_3$–$C_7$) cycloalkyl include, but are not limited to, cyclopropyl, cyclobutyl, cyclopentyl, cyclohexyl, and cycloheptyl, and saturated cyclic and bicyclic terpenes.

As used herein, the term "($C_3$–$C_7$) cycloalkenyl" means a monocyclic or bicyclic unsaturated ring consisting of carbon and hydrogen atoms and having 3–7 carbon atoms. A ($C_3$–$C_7$) cycloalkenyl can be unsubstituted or substituted with, e.g., -amino, —COOH, -halogen, $C_1$–$C_{10}$ (oxy)alkyl, —C(O)$C_1$–$C_9$ alkyl, —SH, =S, —OH, $C_1$–$C_{10}$ alkoxy, and $C_1$–$C_{10}$ alkyl. Examples of ($C_3$–$C_7$) cycloalkyl include, but are not limited to, cyclopropenyl, cyclobutenyl, cyclopentenyl, cyclohexenyl, and cycloheptenyl, and unsaturated cyclic and bicyclic terpenes.

As used herein, the term "aryl" means a carbocyclic aromatic group. All of the ring atoms of an aryl group are carbon atoms. Aryl groups include compounds having one or more ring structures such as mono-, bi-, or tricyclic compounds as well as benzo-fused carbocyclic moieties such as 5,6,7,8-tetrahydronaphthyl and the like. In one embodiment, the aryl group is a monocyclic ring or bicyclic ring. Representative aryl groups include phenyl, tolyl, anthryl, fluorenyl, indenyl, azulenyl, phenanthryl and naphthyl. A carbocyclic aryl group can be unsubstituted or substituted with, e.g., -amino, —COOH, -halogen, $C_1$–$C_{10}$ (oxy)alkyl, —C(O)$C_1$–$C_9$ alkyl, —SH, =S, —OH, $C_1$–$C_{10}$ alkoxy, and $C_1$–$C_{10}$ alkyl.

As used herein, the term "$C_1$–$C_{10}$ (aryl)alkyl" means $C_1$–$C_{10}$ alkyl, wherein $C_1$–$C_{10}$ alkyl is defined above, substituted with one or more aryl groups, wherein aryl is defined above. Examples of $C_1$–$C_{10}$ (aryl)alkyl include, but not limited to —($CH_2$)phenyl, —$(CH_2)_2$phenyl, —$(CH_2)_3$phenyl, —CH(phenyl)$_2$, —CH(phenyl)$_3$, —($CH_2$)tolyl, —($CH_2$)anthracenyl, —($CH_2$)fluorenyl, —($CH_2$)indenyl, —($CH_2$)azulenyl, —($CH_2$)naphthyl, and the like.

As used herein, the term "$C_2$–$C_{10}$ (aryl)alkenyl" means $C_2$–$C_{10}$ alkenyl, wherein $C_2$–$C_{10}$ alkenyl is defined above, substituted with one or more aryl groups, wherein aryl is defined above.

As used herein, the term "$C_2$–$C_{10}$ (aryl)alkynyl" means $C_2$–$C_{10}$ alkynyl, wherein $C_2$–$C_{10}$ alkynyl is defined above, substituted with one or more aryl groups, wherein aryl is defined above.

As used herein, the term "three- to seven-membered aromatic heterocycle" means a heterocyclic ring that contains 3 to 7 ring atoms and that is aromatic. A three-membered heterocycle can contain up to 3 heteroatoms, and a 4- to 7-membered heterocycle can contain up to 4 heteroatoms, wherein the remaining atoms are carbon atoms. Each heteroatom is independently selected from nitrogen, which can be quaternized; oxygen; phosphorus and sulfur, including sulfoxide and sulfone. The heterocycle can be attached via any heteroatom or carbon atom. Representative three- to seven-membered aromatic heterocycles include, but are not limited to, pyridyl, furyl, thiophenyl, pyrrolyl, oxazolyl, imidazolyl, thiazolyl, isoxazolyl, pyrazolyl, isothiazolyl, pyridazinyl, pyrimidinyl, pyrazinyl, and triazinyl.

As used herein, the term "three- to seven-membered non-aromatic heterocycle" means a heterocyclic ring that contains 3 to 7 ring atoms and that is non-aromatic. A three-membered heterocycle can contain up to 3 heteroatoms, and a 4- to 7-membered heterocycle can contain up to 4 heteroatoms, wherein the remaining atoms are carbon atoms. Each heteroatom is independently selected from nitrogen, which can be quaternized; oxygen; phosphorus; and sulfur, including sulfoxide and sulfone. The heterocycle can be attached via any heteroatom or carbon atom. Representative three- to seven-membered non-aromatic heterocycles include, but are not limited to, morpholinyl, pyrrolidinonyl, pyrrolidinyl, piperidinyl, piperazinyl, hydantoinyl, valerolactamyl, oxiranyl, oxetanyl, pyranyl, tetrahydrofuranyl, tetrahydropyranyl, tetrahydropyridinyl, tetrahydropyrimidinyl, tetrahydrothiophenyl, and tetrahydrothiopyranyl.

As used herein, the term "five- to seven-membered aromatic heterocycle" means a heterocyclic ring that contains 5 to 7 ring atoms and that is aromatic. A five- to seven-membered heterocycle can contain up to 4 heteroatoms, wherein the remaining atoms are carbon atoms. Each heteroatom is independently selected from nitrogen, which can be quaternized; oxygen; phosphorus; and sulfur, including sulfoxide and sulfone. The heterocycle can be attached via any heteroatom or carbon atom. Representative five- to seven-membered aromatic heterocycles include, but are not limited to, pyridyl, furyl, thiophenyl, pyrrolyl, furazanyl, oxazolyl, imidazolyl, thiazolyl, thiadiazolyl, isoxazolyl, pyrazolyl, isothiazolyl, pyridazinyl, pyrimidinyl, pyrazinyl, and triazinyl.

As used herein, the term "five- to seven-membered non-aromatic heterocycle" means a heterocyclic ring that contains 5 to 7 ring atoms and that is non-aromatic. A five- to seven-membered heterocycle can contain up to 4 heteroatoms, wherein the remaining atoms are carbon atoms. Each heteroatom is independently selected from nitrogen, which can be quaternized; oxygen; phosphorus; and sulfur, including sulfoxide and sulfone. The heterocycle can be attached via any heteroatom or carbon atom. Representative five- to seven-membered non-aromatic heterocycles include, but are not limited to, morpholinyl, pyranyl, pyrrolidinonyl, pyrrolidinyl, piperidinyl, piperazinyl, hydantoinyl, valerolactamyl, tetrahydrofuranyl, tetrahydropyranyl, tetrahydropyridinyl, tetrahydropyrimidinyl, tetrahydrothiophenyl, and tetrahydrothiopyranyl.

As used herein, the term "non-oxygen-containing five-membered non-aromatic heterocycle" means a heterocyclic ring that contains 5 ring atoms and that is non-aromatic. A five-membered heterocycle can contain up to 4 heteroatoms, wherein the remaining atoms are carbon atoms. Each heteroatom is independently selected from nitrogen, which can be quaternized; phosphorus; and sulfur, including sulfoxide and sulfone. The heterocycle can be attached via any heteroatom or carbon atom.

As used herein, the term "non-oxygen-containing five-membered aromatic heterocycle" means a heterocyclic ring that contains 5 ring atoms and that is aromatic. A five-membered heterocycle can contain up to 4 heteroatoms, wherein the remaining atoms are carbon atoms. Each heteroatom is independently selected from nitrogen, which can be quaternized; phosphorus; and sulfur, including sulfoxide and sulfone. The heterocycle can be attached via any heteroatom or carbon atom.

Examples of "halogen" are fluorine, chlorine, bromine, and iodine.

As used herein, the term "$C_1$–$C_{10}$ (oxy)alkyl" means $C_1$–$C_{10}$ alkyl, wherein $C_1$–$C_{10}$ alkyl is defined above, and wherein one of its carbon atoms is a C=O group. Examples of $C_1$–$C_{10}$ (oxy)alkyl include, but are not limited to, —C(O)CH$_3$, —CH$_2$CHO, —C(O)(CH$_2$)$_2$CH$_3$, —CH$_2$C(O)CH$_3$, —(CH$_2$)$_2$CHO, —(CH$_2$)$_3$CHO, —(CH$_2$)$_4$CHO an the like.

As used herein, an "effective amount" when used in connection with a Diterpenoid Compound refers to that amount of the Diterpenoid Compound useful for treating or preventing cancer, a neoplastic disease or a fungal infection; for inhibiting the growth of a cancer cell, neoplastic cell or fungus; or for inducing cytotoxicity, e.g., through apoptosis, in a cancer cell or a neoplastic cell, alone or in combination with another active-agent. As used herein, an "effective amount" when used in connection with another active agent refers to that amount of the other active agent that is useful for treating or preventing a particular disease or condition, alone or in combination with a Diterpenoid Compound.

As used herein, the term "treating cancer or a neoplastic disease" includes reducing the size of a tumor, ameliorating one or more symptoms associated with a cancer or a neoplastic disease, or inducing cytotoxicity, e.g., through apoptosis, selectively in cells of a cancer or neoplastic disease relative to a non-cancerous or non-neoplastic cell. The term "treating a cancer or a neoplastic disease" further includes arresting or retarding the progression of a cancer or a neoplastic disease.

As used herein, the term "peptide" is a sequence of two to six amino acids. In certain embodiments, a peptide is two, three, four, five, or six amino acids long.

As used herein, the term "pharmaceutically acceptable salt" refers to a salt prepared from an acid or a base including inorganic acids and bases and organic acids and bases. Suitable pharmaceutically acceptable salts of a Diterpenoid Compound having a —COOH group include, but are not limited to, metallic salts of aluminum, calcium, lithium, magnesium, potassium, sodium and zinc, or organic salts of lysine, N,N'-dibenzylethylenediamine, chloroprocaine, choline, diethanolamine, ethylenediamine, meglumine (N-methylglucamine) and procaine. Acids useful for forming suitable salts with a Diterpenoid Compound having a nitrogen or sulfur atom include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Other examples of salts are well known in the art, see, e.g., *Remington's Pharmaceutical Sciences*, 18th ed., Mack Publishing, Easton Pa. (1990).

As used herein, the term "isolated" means separated from other components of a naturally occurring source (such as a plant or animal cell, including a hepatocyte; cell culture; tissue; in vivo fluid including intracellular and extracellular fluid, including blood and plasma; and ex vivo fluid including sputum, urine, sweat, semen, menstrual fluid, and milk) or from a synthetic organic chemical reaction mixture.

As used herein the term "purified" means that the compound is free of other components such that the compound is pure. In certain embodiments, a compound of the invention is at least about 90% pure. In certain embodiments, a compound of the invention is at least about 95% pure. In one embodiment, the compound of the invention is at least about 98% pure. In another embodiment, the compound of the invention is at least about 99% pure.

When a first group is substituted with "one or more" second group(s), a hydrogen of the first group is replaced with the second group. In one embodiment, a first group is substituted with one, two or three second groups. In another embodiment, a first group is substituted with one or two second groups. In even another embodiment, a first group is substituted with one second group.

As used herein, the term "patient" refers preferably to an animal, including, but not limited, to a vertebrate such a chimpanzee, baboon, cow, horse, sheep, pig, chicken, turkey, quail, cat, dog, mouse, rat, rabbit, and guinea pig, and in one embodiment a mammal, and in a more specific embodiment a human.

A Diterpenoid Compound can have one or more chiral centers and, accordingly, can exist in the form of a diastereomer, a (+)- or (−)-enantiomer, a racemate, or a mixture thereof. It is recognized that Diterpenoid Compounds of the invention can have one or more chiral centers and/or double bonds and, therefore, exist as stereoisomers, such as double-bond isomers (i.e., geometric isomers), enantiomers, or diastereomers. According to the invention, if a chemical structure depicted herein does not indicate the stereochemistry at a chiral center, the compound encompasses all of the corresponding enantiomers and stereoisomers, that is, both the stereomerically pure form (e.g., geometrically pure, enantiomerically pure, or diastereomerically pure) and enantiomeric and stereoisomeric mixtures, e.g., racemates.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diasteroemers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

Enantiomeric and stereoisomeric mixtures of compounds of the invention can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

| Abbreviations | |
|---|---|
| IBX | iodoxybenzoate |
| TBAF | tetra-n-butylammonium fluoride |
| BRDU | bromodeoxyuridine |
| i.v. | intravenous |
| Rpm | revolutions per minute |
| ATCC | American Type Culture Collection |
| LC/MS | Liquid Chromatography/Mass Spectrometry |

The Diterpenoid Compounds can exist in the form of a pharmaceutically acceptable salt, free base, solvate, hydrate, stereoisomer, clathrate, polymorph or prodrug thereof.

The invention can be understood more fully by reference to the following description, figures and illustrative examples, which are intended to exemplify non-limiting embodiments of the invention.

5.2 Formula I

As stated above, the present invention encompasses compounds having the Formula (Ia), (Ib) or (Ic):

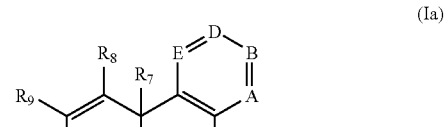
(Ia)

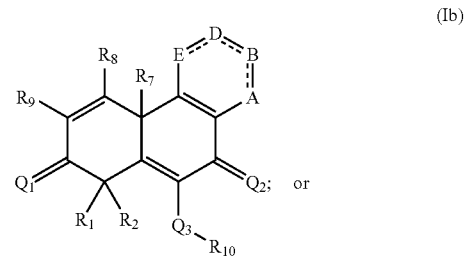
(Ib)

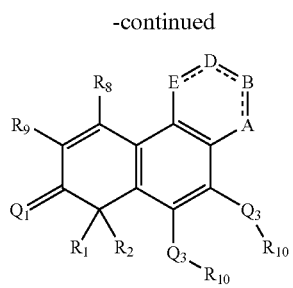

(Ic)

and pharmaceutically acceptable salts thereof, wherein $Q_1$–$Q_3$, $R_1$–$R_{13}$, A–E and halogen are defined above for Formula (Ia), (Ib) and (Ic), respectively.

A Diterpenoid Compound of Formula (Ia), (Ib) or (Ic) is useful for treating or preventing cancer or neoplastic disease in a patient in need of such treatment or prevention. A Diterpenoid Compound of Formula (Ia), (Ib) or (Ic) is also useful for inhibiting the growth of a cancer cell or neoplastic cell. A Diterpenoid Compound of Formula (Ia), (Ib) or (Ic) is also useful for inducing cytotoxicity, e.g., through apoptosis, in a cancer cell or neoplastic cell. A Diterpenoid Compound of Formula (Ia), (Ib) or (Ic) is further useful for treating or preventing a fungal infection. A Diterpenoid Compound of Formula (Ia), (Ib) or (Ic) is also useful for inhibiting the growth of a fungus.

In one embodiment, the Diterpenoid Compounds of Formula (Ia), (Ib) or (Ic) are those wherein $Q_1$ and $Q_2$ are =O and $Q_3$ is —O—.

In another embodiment, the Diterpenoid Compounds of Formula (Ia), (Ib) or (Ic) are those wherein A, B, D and E are $CR_3$, $CR_4$, $CR_5$ and $CR_6$, respectively.

In another embodiment, the Diterpenoid Compounds of Formula (Ia), (Ib) or (Ic) are those wherein A is $CR_3$, E is $CR_6$, and $R_3$ and $R_6$ are hydrogen.

In another embodiment, the Diterpenoid Compounds of Formula (Ia), (Ib) or (Ic) are those wherein D is $CR_5$ and $R_5$ is $C_1$–$C_6$ alkoxy, in another embodiment, —$OCH_3$.

In another embodiment, the Diterpenoid Compounds of Formula (Ia), (Ib) or (Ic) are those wherein B is $CR_4$ and $R_4$ is hydrogen.

In another embodiment, the Diterpenoid Compounds of Formula (Ia), (Ib) or (Ic) are those wherein B is $CR_4$, $R_4$ is hydrogen, D is $CR_5$ and $R_5$ is $C_1$–$C_6$ alkoxy.

In another embodiment, the Diterpenoid Compounds of Formula (Ia), (Ib) or (Ic) are those wherein B is $CR_4$, $R_4$ is hydrogen, D is $CR_5$ and $R_5$ is —$OCH_3$.

In another embodiment, the Diterpenoid Compounds of Formula (Ia), (Ib) or (Ic) are those wherein B is $CR_4$ and $R_4$ is $C_1$–$C_{10}$ alkyl, in another embodiment, —$CH_3$.

In another embodiment, the Diterpenoid Compounds of Formula (Ia), (Ib) or (Ic) are those wherein B is $CR_4$ and $R_4$ is $C_1$–$C_{10}$ (hydroxy)alkyl, in another embodiment, hydroxymethyl.

In another embodiment, $R_8$ and $R_9$ are hydrogen.

In another embodiment, $R_1$ and $R_2$ are independently $C_1$–$C_{10}$ alkyl, in another embodiment, —$CH_3$.

In another embodiment, $R_{10}$ is hydrogen.

In another embodiment, -$Q_3$-$R_{10}$ is —OH.

In another embodiment, $R_7$ is $C_1$–$C_{10}$ alkyl, in another embodiment —$CH_3$.

In one embodiment, $Q_1$ and $Q_2$ and $Q_3$ are oxygen. In another embodiment, $R_1$ and $R_2$ are $C_1$–$C_{10}$ alkyl. In another embodiment, $R_8$ and $R_9$ are H. In another embodiment, $R_7$ is $C_1$–$C_{10}$ alkyl. In another embodiment, $R_3$ and $R_6$ are H. In another embodiment, $R_4$ and $R_5$ are independently $C_1$–$C_{10}$ alkyl, $C_1$–$C_{10}$ alkoxy, or $C_1$–$C_{10}$ (hydroxy)alkyl.

In one embodiment, the Diterpenoid Compounds of Formula (Ia), (Ib) and (Ic) are in isolated and purified form.

Illustrative Diterpenoid Compound of Formula (Ia) are:

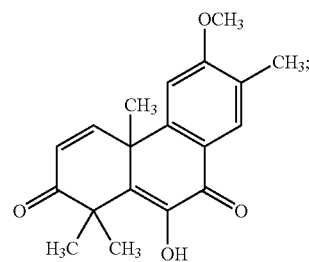

48

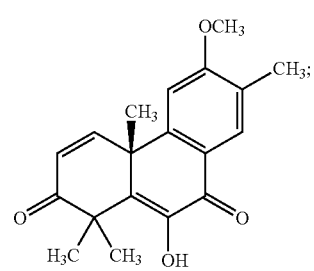

48a

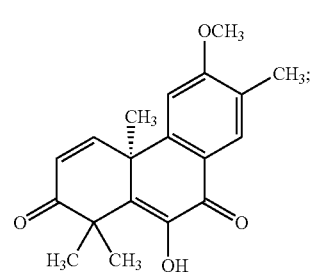

48b

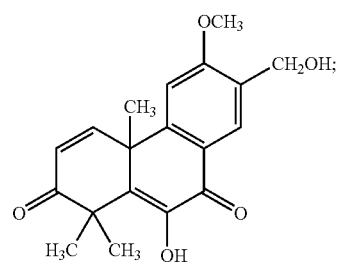

49

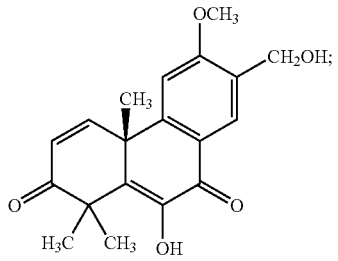

49a

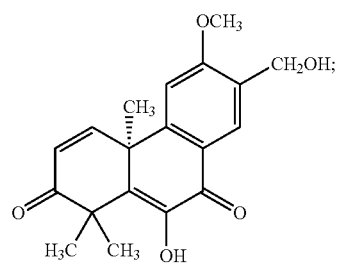
49b
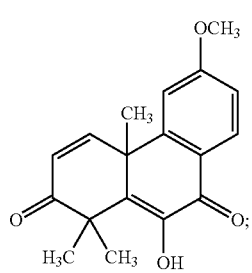
50
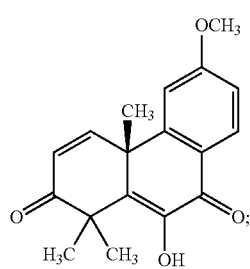
50a
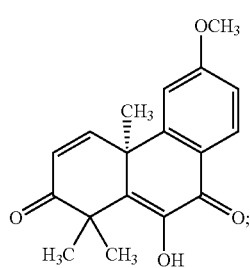
50b
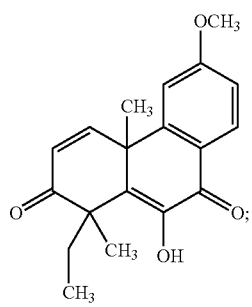
66
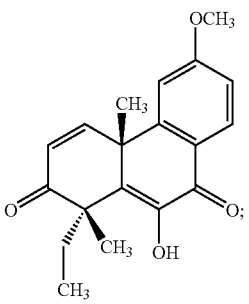
66a
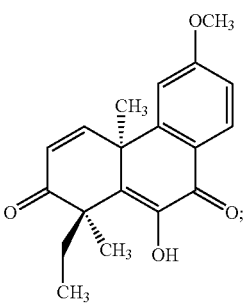
66b
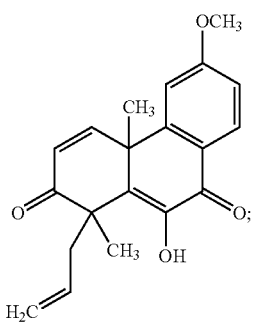
67
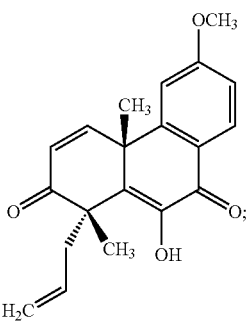
67a
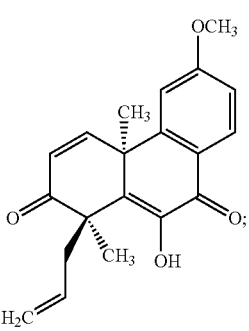
67b

68

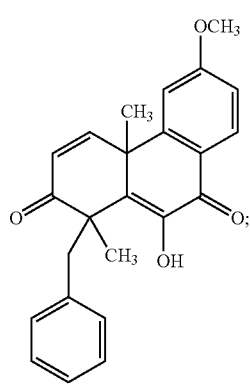

68a

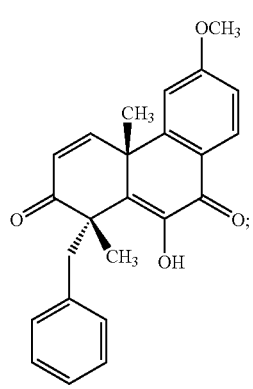

68b

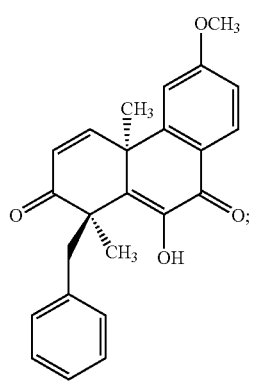

69

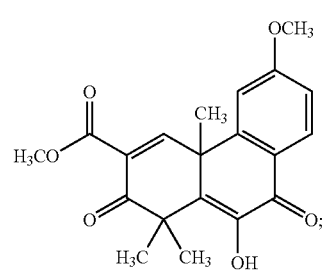

69a

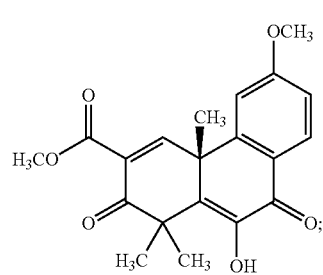

69b

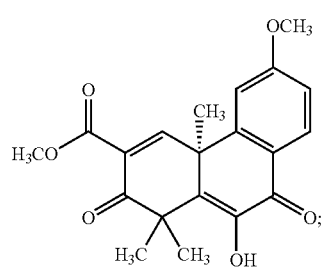

76

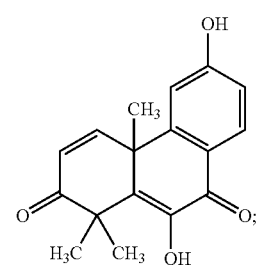

and pharmaceutically acceptable salts thereof.

It is to be understood that Compound 50 is the racemate of its corresponding enantiomers Compound 50a and 50b; Compound 66 is the racemate of its corresponding enantiomers Compound 66a and 66b; Compound 67 is the racemate of its corresponding enantiomers Compound 67a and 67b; Compound 68 is the racemate of its corresponding enantiomers Compound 68a and 68b; and that Compound 69 is the racemate of its corresponding enantiomers Compound 69a and 69b.

Tautomeric Reaction

It is believed that compounds of Formula (Ia) can be converted into their tautomers of Formula (Ic).

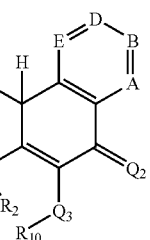

(Ia)

-continued

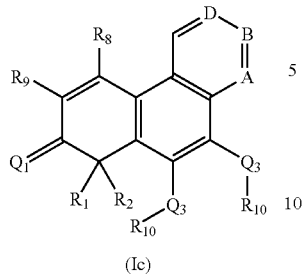

(Ic)

5.3 Formula II

As stated above, the present invention encompasses compounds having the Formula (IIa), (IIb) or (IIc):

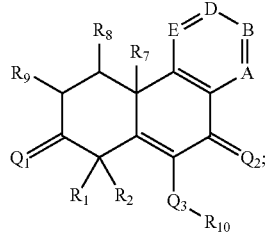

(IIa)

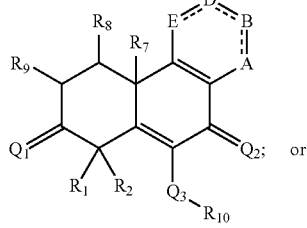

(IIb)

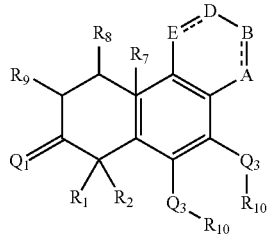

(IIc)

and pharmaceutically acceptable salts thereof, wherein $Q_1$–$Q_3$, $R_1$–$R_{13}$, A–E and halogen are defined above for Formula (IIa), (IIb) or (IIc), respectively.

A Diterpenoid Compound of Formula (IIa), (IIb) or (IIc) is useful for treating or preventing cancer or neoplastic disease in a patient in need of such treatment or prevention. A Diterpenoid Compound of Formula (IIa), (IIb) or (IIc) is also useful for inhibiting the growth of a cancer cell or neoplastic cell. A Diterpenoid Compound of Formula (IIa), (IIb) or (IIc) is also useful for inducing cytotoxicity, e.g., through apoptosis, in a cancer cell or neoplastic cell. A Diterpenoid Compound of Formula (IIa), (IIb) or (IIc) is further useful for treating or preventing a fungal infection. A Diterpenoid Compound of Formula (IIa), (IIb) or (IIc) is also useful for inhibiting the growth of a fungus.

In one embodiment, the Diterpenoid Compounds of Formula (IIa), (IIb) or (IIc) are those wherein $Q_1$ and $Q_2$ are =O and $Q_3$ is —O—.

In another embodiment, the Diterpenoid Compounds of Formula (IIa), (IIb) or (IIc) are those wherein A, B, D and E are $CR_3$, $CR_4$, $CR_5$ and $CR_6$, respectively.

In another embodiment, the Diterpenoid Compounds of Formula (IIa), (IIb) or (IIc) are those wherein A is $CR_3$, E is $CR_6$, and $R_3$ and $R_6$ are hydrogen.

In another embodiment, the Diterpenoid Compounds of Formula (IIa), (IIb) or (IIc) are those wherein D is $CR_5$ and $R_5$ is $C_1$–$C_6$ alkoxy, in another embodiment, —$OCH_3$.

In another embodiment, the Diterpenoid Compounds of Formula (IIa), (IIb) or (IIc) are those wherein B is $CR_4$ and $R_4$ is hydrogen.

In another embodiment, the Diterpenoid Compounds of Formula (IIa), (IIb) or (IIc) are those wherein B is $CR_4$, $R_4$ is hydrogen, D is $CR_5$ and $R_5$ is $C_1$–$C_6$ alkoxy.

In another embodiment, the Diterpenoid Compounds of Formula (IIa), (IIb) or (IIc) are those wherein B is $CR_4$, $R_4$ is hydrogen, D is $CR_5$ and $R_5$ is —$OCH_3$.

In another embodiment, the Diterpenoid Compounds of Formula (IIa), (IIb) or (IIc) are those wherein B is $CR_4$ and $R_4$ is $C_1$–$C_{10}$ alkyl, in another embodiment, —$CH_3$.

In another embodiment, the Diterpenoid Compounds of Formula (IIa), (IIb) or (IIc) are those wherein B is $CR_4$ and $R_4$ is $C_1$–$C_{10}$ (hydroxy)alkyl, in another embodiment, hydroxymethyl.

In another embodiment, $R_8$ and $R_9$ are hydrogen.

In another embodiment, $R_1$ and $R_2$ are independently $C_1$–$C_{10}$ alkyl, in another embodiment, —$CH_3$.

In another embodiment, $R_{10}$ is hydrogen.

In another embodiment, -$Q_3$-$R_{10}$ is —OH.

In another embodiment, $R_7$ is $C_1$–$C_{10}$ alkyl, in another embodiment —$CH_3$.

In another embodiment, the Diterpenoid Compounds of Formula (II) are in isolated and purified form.

Illustrative compounds of Formula (IIa) are:

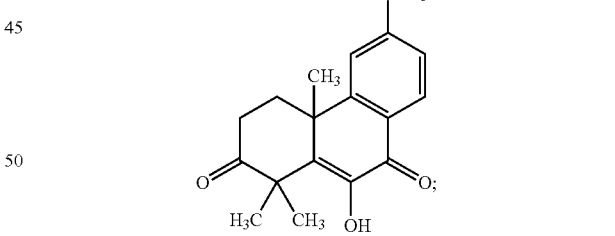

78

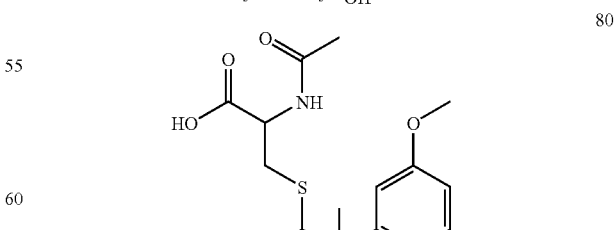

80

-continued

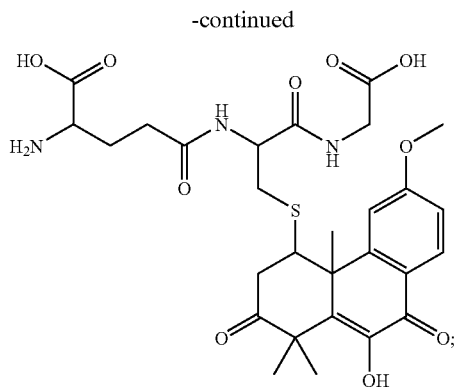

81 and pharmaceutically acceptable salts thereof.

Tautomeric Reaction

It is believed that compounds of Formula (IIa) can be converted into their tautomers of Formula (IIc).

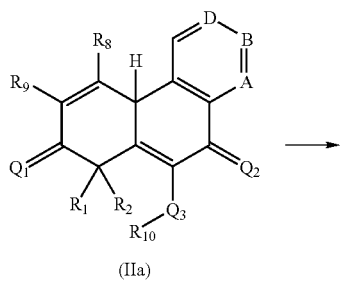

(IIa)

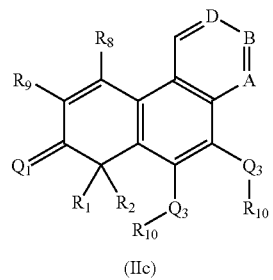

(IIc)

5.4 Formula III

As stated above, the present invention encompasses novel compounds having the Formula (IIIa) or (IIIb):

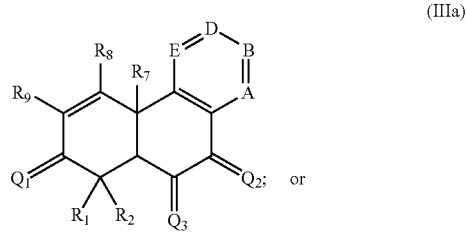

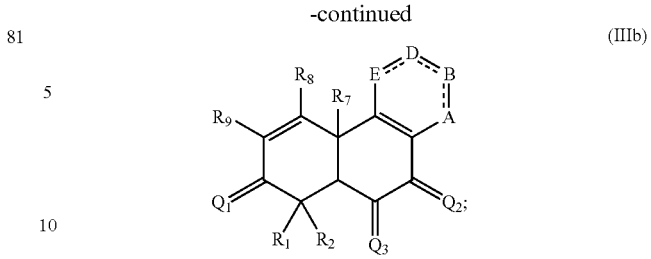

and pharmaceutically acceptable salts thereof, wherein $Q_1-Q_3$, $R_1-R_9$, $R_{11}-R_{12}$, A–E and halogen are defined above for Formula (IIIa) and (IIIb), respectively.

A Diterpenoid Compound of Formula (IIIa) or (IIIb) is useful for treating or preventing cancer or neoplastic disease in a patient in need of such treatment or prevention. A Diterpenoid Compound of Formula (IIIa) or (IIIb) is also useful for inhibiting the growth of a cancer cell or neoplastic cell. A Diterpenoid Compounds of Formula (IIIa) or (IIIb) is also useful for inducing cytotoxicity, e.g., through apoptosis, in a cancer cell or neoplastic cell. A Diterpenoid Compound of Formula (IIIa) or (IIIb) is further useful for treating or preventing a fungal infection. A Diterpenoid Compound of Formula (IIIa) or (IIIb) is also useful for inhibiting the growth of a fungus.

In one embodiment, the Diterpenoid Compounds of Formula (IIIa) or (IIIb) are those wherein $Q_1$, $Q_2$ and $Q_3$ are =O.

In another embodiment, the Diterpenoid Compounds of Formula (IIIa) or (IIIb) are those wherein A, B, D and E are $CR_3$, $CR_4$, $CR_5$ and $CR_6$, respectively.

In another embodiment, the Diterpenoid Compounds of Formula (IIIa) or (IIIb) are those wherein A is $CR_3$, E is $CR_6$, and $R_3$ and $R_6$ are hydrogen.

In another embodiment, the Diterpenoid Compounds of Formula (IIIa) or (IIb) are those wherein D is $CR_5$ and $R_5$ is $C_1-C_6$ alkoxy, in another embodiment, —$OCH_3$.

In another embodiment, the Diterpenoid Compounds of Formula (IIIa) or (IIIb) are those wherein B is $CR_4$ and $R_4$ is hydrogen.

In another embodiment, the Diterpenoid Compounds of Formula (IIIa) or (IIIb) are those wherein B is $CR_4$, $R_4$ is hydrogen, D is $CR_5$ and $R_5$ is $C_1-C_6$ alkoxy.

In another embodiment, the Diterpenoid Compounds of Formula (IIIa) or (IIIb) are those wherein B is $CR_4$, $R_4$ is hydrogen, D is $CR_5$ and $R_5$ is —$OCH_3$.

In another embodiment, the Diterpenoid Compounds of Formula (IIIa) or (IIIb) are those wherein B is $CR_4$ and $R_4$ is $C_1-C_{10}$ alkyl, in another embodiment, —$CH_3$.

In another embodiment, the Diterpenoid Compounds of Formula (IIIa) or (IIIb) are those wherein B is $CR_4$ and $R_4$ is $C_1-C_{10}$ (hydroxy)alkyl, in another embodiment, hydroxymethyl.

In another embodiment, $R_8$ and $R_9$ are hydrogen.

In another embodiment, $R_1$ and $R_2$ are independently $C_1-C_{10}$ alkyl, in another embodiment, —$CH_3$.

In another embodiment, $R_7$ is $C_1-C_{10}$ alkyl, in another embodiment —$CH_3$.

In another embodiment, the Diterpenoid Compounds of Formula (IIIa) or (IIIb) are in isolated and purified form.

An illustrative Diterpenoid Compound of Formula (IIIa) is:

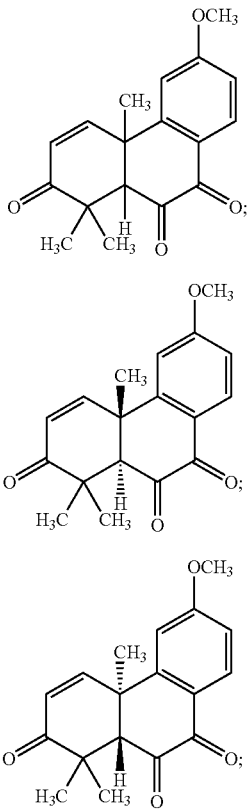

and pharmaceutically acceptable salts thereof.

It is to be understood that Compound 70 is the racemate of its corresponding enantiomers Compound 70a and 70b.

5.5 Formula IV

As stated above, the present invention encompasses novel compounds having the Formula (IVa) or (IVb):

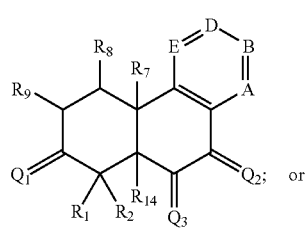

(IVa)

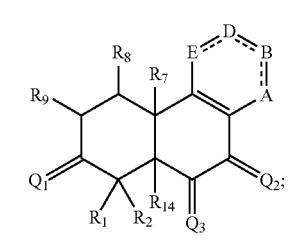

(IVb)

and pharmaceutically acceptable salts thereof, wherein $Q_1$–$Q_3$, $R_1$–$R_9$, $R_{11}$–$R_{12}$, A–E and halogen are defined above for Formula (IVa) and (IVb), respectively.

A Diterpenoid Compounds of Formula (IVa) or (IVb) is useful for treating or preventing cancer or neoplastic disease in a patient in need of such treatment or prevention. A Diterpenoid Compounds of Formula (IVa) or (IVb) is also useful for inhibiting the growth of a cancer cell or neoplastic cell. A Diterpenoid Compounds of Formula (IVa) or (IVb) is also useful for inducing cytotoxicity, e.g., through apoptosis, in a cancer cell or neoplastic cell. A Diterpenoid Compounds of Formula (IVa) or (IVb) is further useful for treating or preventing a fungal infection. A Diterpenoid Compounds of Formula (IVa) or (IVb) is also useful for inhibiting the growth of a fungus.

In one embodiment, the Diterpenoid Compounds of Formula (IVa) or (IVb) are those wherein $Q_1$, $Q_2$ and $Q_3$ are ═ O.

In another embodiment, the Diterpenoid Compounds of Formula (IVa) or (IVb) are those wherein A, B, D and E are $CR_3$, $CR_4$, $CR_5$ and $CR_6$, respectively.

In another embodiment, the Diterpenoid Compounds of Formula (IVa) or (IVb) are those wherein A is $CR_3$, E is $CR_6$, and $R_3$ and $R_6$ are hydrogen.

In another embodiment, the Diterpenoid Compounds of Formula (IVa) or (IVb) are those wherein D is $CR_5$ and $R_5$ is $C_1$–$C_6$ alkoxy, in another embodiment, —$OCH_3$.

In another embodiment, the Diterpenoid Compounds of Formula (IVa) or (IVb) are those wherein B is $CR_4$ and $R_4$ is hydrogen.

In another embodiment, the Diterpenoid Compounds of Formula (IVa) or (IVb) are those wherein B is $CR_4$, $R_4$ is hydrogen, D is $CR_5$ and $R_5$ is $C_1$–$C_6$ alkoxy.

In another embodiment, the Diterpenoid Compounds of Formula (IVa) or (IVb) are those wherein B is $CR_4$, $R_4$ is hydrogen, D is $CR_5$ and $R_5$ is —$OCH_3$.

In another embodiment, the Diterpenoid Compounds of Formula (IVa) or (IVb) are those wherein B is $CR_4$ and $R_4$ is $C_1$–$C_{10}$ alkyl, in another embodiment, —$CH_3$.

In another embodiment, the Diterpenoid Compounds of Formula (IVa) or (IVb) are those wherein B is $CR_4$ and $R_4$ is $C_1$–$C_{10}$ (hydroxy)alkyl, in another embodiment, hydroxymethyl.

In another embodiment, $R_8$ and $R_9$ are hydrogen.

In another embodiment, $R_1$ and $R_2$ are independently $C_1$–$C_{10}$ alkyl, in another embodiment, —$CH_3$.

In another embodiment, $R_7$ is $C_1$–$C_{10}$ alkyl, in another embodiment —$CH_3$.

In another embodiment, the Diterpenoid Compounds of Formula (IVa) or (IVb) are in isolated and purified form.

5.6 Formula V

As stated above, the present invention encompasses novel compounds having the Formula (Va) or (Vb):

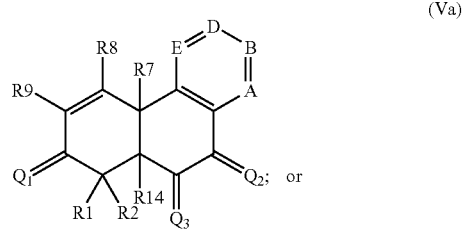

(Va)

-continued

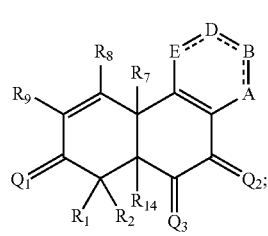

(Vb)

and pharmaceutically acceptable salts thereof, wherein $Q_1$–$Q_3$, $R_1$–$R_9$, $R_{11}$, $R_{12}$, $R_{14}$, A–E and halogen are defined above for Formula (Va) and (Vb), respectively.

A Diterpenoid Compounds of Formula (Va) or (Vb) is useful for treating or preventing cancer or neoplastic disease in a patient in need of such treatment or prevention. A Diterpenoid Compounds of Formula (Va) or (Vb) is also useful for inhibiting the growth of a cancer cell or neoplastic cell. A Diterpenoid Compounds of Formula (Va) or (Vb) is also useful for inducing cytotoxicity, e.g., through apoptosis, in a cancer cell or neoplastic cell. A Diterpenoid Compounds of Formula (Va) or (Vb) is further useful for treating or preventing a fungal infection. A Diterpenoid Compounds of Formula (Va) or (Vb) is also useful for inhibiting the growth of a fungus.

In one embodiment, the Diterpenoid Compounds of Formula (Va) or (Vb) are those wherein $Q_1$, $Q_2$ and $Q_3$ are =O.

In another embodiment, the Diterpenoid Compounds of Formula (Va) or (Vb) are those wherein A, B, D and E are $CR_3$, $CR_4$, $CR_5$ and $CR_6$, respectively.

In another embodiment, the Diterpenoid Compounds of Formula (Va) or (Vb) are those wherein A is $CR_3$, E is $CR_6$, and $R_3$ and $R_6$ are hydrogen.

In another embodiment, the Diterpenoid Compounds of Formula (Va) or (Vb) are those wherein D is $CR_5$ and $R_5$ is $C_1$–$C_6$ alkoxy, in another embodiment, —$OCH_3$.

In another embodiment, the Diterpenoid Compounds of Formula (Va) or (Vb) are those wherein B is $CR_4$ and $R_4$ is hydrogen.

In another embodiment, the Diterpenoid Compounds of Formula (Va) or (Vb) are those wherein B is $CR_4$, $R_4$ is hydrogen, D is $CR_5$ and $R_5$ is $C_1$–$C_6$ alkoxy.

In another embodiment, the Diterpenoid Compounds of Formula (Va) or (Vb) are those wherein B is $CR_4$, $R_4$ is hydrogen, D is $CR_5$ and $R_5$ is —$OCH_3$.

In another embodiment, the Diterpenoid Compounds of Formula (Va) or (Vb) are those wherein B is $CR_4$ and $R_4$ is $C_1$–$C_{10}$ alkyl, in another embodiment, —$CH_3$.

In another embodiment, the Diterpenoid Compounds of Formula (Va) or (Vb) are those wherein B is $CR_4$ and $R_4$ is $C_1$–$C_{10}$ (hydroxy)alkyl, in another embodiment, hydroxymethyl.

In another embodiment, $R_8$ and $R_9$ are hydrogen.

In another embodiment, $R_1$ and $R_2$ are independently $C_1$–$C_{10}$ alkyl, in another embodiment, —$CH_3$.

In another embodiment, $R_7$ is $C_1$–$C_{10}$ alkyl, in another embodiment —$CH_3$.

In another embodiment, the Diterpenoid Compounds of Formula (Va) or (Vb) are in isolated and purified form.

Illustrative compounds of Formula (Va) are

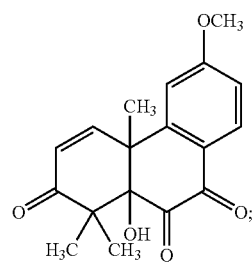

77

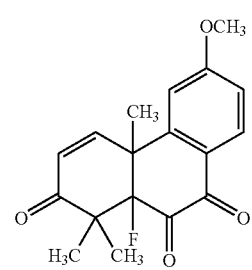

79 or pharmaceutically acceptable salts thereof. In certain embodiments, $R_7$ and $R_{14}$ in a compound of Formula (Va) are in trans to each other. In more specific embodiments, $R_7$ and $R_{14}$ in Compound 79 are in trans to each other.

5.7 Formula VI

As stated above, the present invention encompasses novel compounds having the Formula (VIa) or (VIb):

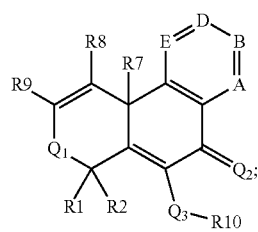

(VIa)

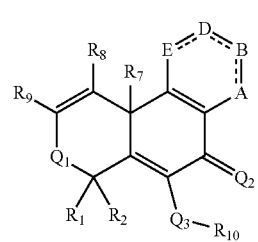

(VIb)

and pharmaceutically acceptable salts thereof, wherein $Q_1$–$Q_3$, $R_1$–$R_{13}$, A–E and halogen are defined above for Formula (VIa) and (VIb), respectively.

A Diterpenoid Compounds of Formula (VIa) or (VIb) is useful for treating or preventing cancer or neoplastic disease in a patient in need of such treatment or prevention. A Diterpenoid Compounds of Formula (VIa) or (VIb) is also useful for inhibiting the growth of a cancer cell or neoplastic cell. A Diterpenoid Compounds of Formula (VIa) or (VIb) is also useful for inducing cytotoxicity, e.g., through apoptosis, in a cancer cell or neoplastic cell. A Diterpenoid Compounds of Formula (VIa) or (VIb) is further useful for treating or preventing a fungal infection. A Diterpenoid Compounds of Formula (VIa) or (VIb) is also useful for inhibiting the growth of a fungus.

In one embodiment, the Diterpenoid Compounds of Formula (VIa) or (VIb) are those wherein $Q_1$ is CHOH, $Q_2$ is =O, and $Q_3$ is —O—.

In another embodiment, the Diterpenoid Compounds of Formula (VIa) or (VIb) are those wherein A, B, D and E are $CR_3$, $CR_4$, $CR_5$ and $CR_6$, respectively.

In another embodiment, the Diterpenoid Compounds of Formula (VIa) or (VIb) are those wherein A is $CR_3$, E is $CR_6$, and $R_3$ and $R_6$ are hydrogen.

In another embodiment, the Diterpenoid Compounds of Formula (VIa) or (VIb) are those wherein D is $CR_5$ and $R_5$ is $C_1$–$C_6$ alkoxy, in another embodiment, —$OCH_3$.

In another embodiment, the Diterpenoid Compounds of Formula (VIa) or (VIb) are those wherein B is $CR_4$ and $R_4$ is hydrogen.

In another embodiment, the Diterpenoid Compounds of Formula (VIa) or (VIb) are those wherein B is $CR_4$, $R_4$ is hydrogen, D is $CR_5$ and $R_5$ is $C_1$–$C_6$ alkoxy.

In another embodiment, the Diterpenoid Compounds of Formula (VIa) or (VIb) are those wherein B is $CR_4$, $R_4$ is hydrogen, D is $CR_5$ and $R_5$ is —$OCH_3$.

In another embodiment, the Diterpenoid Compounds of Formula (VIa) or (VIb) are those wherein B is $CR_4$ and $R_4$ is $C_1$–$C_{10}$ alkyl, in another embodiment, —$CH_3$.

In another embodiment, the Diterpenoid Compounds of Formula (VIa) or (VIb) are those wherein B is $CR_4$ and $R_4$ is $C_1$–$C_{10}$ (hydroxy)alkyl, in another embodiment, hydroxymethyl.

In another embodiment, $R_8$ and $R_9$ are hydrogen.

In another embodiment, $R_1$ and $R_2$ are independently $C_1$–$C_{10}$ alkyl, in another embodiment, —$CH_3$.

In another embodiment, $R_7$ is $C_1$–$C_{10}$ alkyl, in another embodiment —$CH_3$.

In another embodiment, the Diterpenoid Compounds of Formula (VIa) or (VIb) are in isolated and purified form.

An illustrative compound of Formula (VIa) is

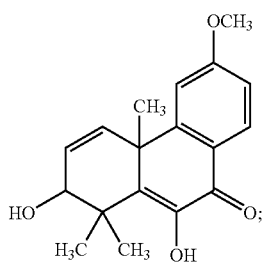

or pharmaceutically acceptable salts thereof.

5.8 Formula VII

As stated above, the present invention encompasses novel compounds having the Formula (VIIa) or (VIIb):

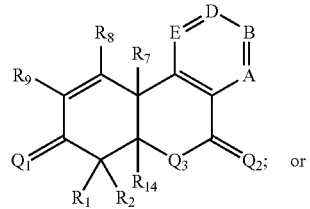

(VIIa)

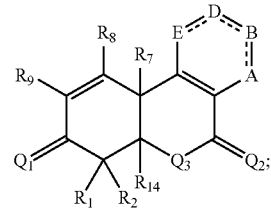

(VIIb)

and pharmaceutically acceptable salts thereof, wherein $Q_1$–$Q_3$, $R_1$–$R_9$, $R_{11}$–$R_{12}$, A–E and halogen are defined above for Formula (VIIa) and (VIIb), respectively.

A Diterpenoid Compounds of Formula (VIIa) or (VIIB) is useful for treating or preventing cancer or neoplastic disease in a patient in need of such treatment or prevention. A Diterpenoid Compounds of Formula (VIIa) or (VIIb) is also useful for inhibiting the growth of a cancer cell or neoplastic cell. A Diterpenoid Compounds of Formula (VIIa) or (VIIb) is also useful for inducing cytotoxicity, e.g., through apoptosis, in a cancer cell or neoplastic cell. A Diterpenoid Compounds of Formula (VIIa) or (VIIb) is further useful for treating or preventing a fungal infection. A Diterpenoid Compounds of Formula (VIIa) or (VIIb) is also useful for inhibiting the growth of a fungus.

In one embodiment, the Diterpenoid Compounds of Formula (VIIa) or (VIIb) are those wherein $Q_1$ and $Q_2$ are =O, and $Q_3$ is $CH_2$.

In another embodiment, the Diterpenoid Compounds of Formula (VIa) or (VIIb) are those wherein A, B, D and E are $CR_3$, $CR_4$, $CR_5$ and $CR_6$, respectively.

In another embodiment, the Diterpenoid Compounds of Formula (VIIa) or (VIIb) are those wherein A is $CR_3$, E is $CR_6$, and $R_3$ and $R_6$ are hydrogen.

In another embodiment, the Diterpenoid Compounds of Formula (VIIa) or (VIIb) are those wherein D is $CR_5$ and $R_5$ is $C_1$–$C_6$ alkoxy, in another embodiment, —$OCH_3$.

In another embodiment, the Diterpenoid Compounds of Formula (VIIa) or (VIIb) are those wherein B is $CR_4$ and $R_4$ is hydrogen.

In another embodiment, the Diterpenoid Compounds of Formula (VIIa) or (VIIb) are those wherein B is $CR_4$, $R_4$ is hydrogen, D is $CR_5$ and $R_5$ is $C_1$–$C_6$ alkoxy.

In another embodiment, the Diterpenoid Compounds of Formula (VIIa) or (VIIb) are those wherein B is $CR_4$, $R_4$ is hydrogen, D is $CR_5$ and $R_5$ is —$OCH_3$.

In another embodiment, the Diterpenoid Compounds of Formula (VIIa) or (VIIb) are those wherein B is $CR_4$ and $R_4$ is $C_1$–$C_{10}$ alkyl, in another embodiment, —$CH_3$.

In another embodiment, the Diterpenoid Compounds of Formula (VIIa) or (VIIb) are those wherein B is $CR_4$ and $R_4$ is $C_1$–$C_{10}$ (hydroxy)alkyl, in another embodiment, hydroxymethyl.

In another embodiment, $R_8$ and $R_9$ are hydrogen.

In another embodiment, $R_1$ and $R_2$ are independently $C_1$–$C_{10}$ alkyl, in another embodiment, —$CH_3$.

In another embodiment, $R_7$ is $C_1$–$C_{10}$ alkyl, in another embodiment —$CH_3$.

In another embodiment, the Diterpenoid Compounds of Formula (VIIa) or (VIIb) are in isolated and purified form.

5.9 Methods for Making Diterpenoid Compounds

The Diterpenoid Compounds can be obtained using conventional organic synthesis or by using the following illustrative methods shown in Schemes 1–7 below. In certain other embodiments, Diterpenoid Compounds of the invention can be isolated from natural sources, such as plant extracts.

Diterpenoid Compounds of Formula (I) or (II) can be obtained from a tetralone-type precursor such as depicted by compounds 13 in Scheme 1. Nucleophilic addition of $R_7$ using an appropriate organometallic reagent, such as a Grignard reagent (E. C. Ashby et al., *J. Am. Chem. Soc.*, 89:1964 (1967)), followed by dehydration (C. Utermoehlen et al., *J. Org. Chem.*, 52:5574 (1987)) provides compounds 14, which can undergo Diels-Alder cycloadditions with dienes such as compounds 15 (S. Danishefsky et al., *J. Am. Chem. Soc.*, 101:7001 (1979)), with or without Lewis acid catalysis, to yield after desilylation tricyclic intermediates 16. The a, b-unsaturation of compounds 17 can be introduced by treating compounds 16 with a strong base such as lithium diisopropyl amide, followed by treatment with phenylselenium chloride, hydrogen peroxide or meta-chloroperoxybenzoic acid (M. Tius et al., *J. Am. Chem. Soc.*, 114:5959 (1992)). Compounds 17 can then be oxidized with, for example, chromium trioxide/sulphuric acid or IBX in DMSO and oxygen with potassium t-butoxide in t-butanol to provide compounds 18 (Nicolaou et al., *J. Am. Chem. Soc.* 123:3183 (2001); Nicolaou et al., *Angew. Chem. Int. Ed.* 40:207 (2001)), which are in equilibrium with enols 19. Compounds 18a, 18b, 19a and 19b can be further modified to provide thioketones, imines, hydrazones, hydrazines, and arylhydrazones, as structurally described in Formulas (I), (II), (III) and (IV) by using simple organic transformations well recognised by chemists skilled in the art of organic synthesis.

Scheme 2 illustrates a synthesis of Diterpenoid Compounds of subgeneric formulas 5a, 5b, 6a, and 6b. This route uses compounds 21, which can be obtained (Scheme 3) in three steps from IBX-DMSO oxidation of aryl- or heteroaryl-substituted propanols 26 (Nicolaou et al., *J. Am. Chem. Soc.* 123:3183 (2001)), followed by Wittig reaction with aldehydes 27 (B. Maryanoff et al., *J. Am. Chem. Soc.*, 107:217, (1985); A. Maercker, *Organic Reactions*, 14:270 (1965)), desilylation of resultant product 28 using a reagent such as, but not limited to, TBAF, and bromination using tribromophosphine in a solvent such as dichloromethane to provide bromide 21.

Carbonyl-containing compounds 20 can be coupled with intermediates 21 using reagents such as NaH or n-butyllithium in tetrahydrofuran to provide compounds 22 (S. Welch et al., J. Am. Chem. Soc, 101:6768 (1979)), which can then be cyclised to the tricyclic intermediates 23 using manganese acetate in acetic acid (B. Snider et al., *J. Org. Chem.*, 50:3659 (1985)). The a, b-unsaturation of compounds 24 can be introduced by treating compounds 23 with lithium diisopropyl amide, phenylselenium chloride, hydrogen peroxide or meta-chloroperoxybenzoic acid (M. Tius et al., *J. Am. Chem. Soc.*, 114:5959 (1992)). Oxidation of compounds 23 and 24 with, for example, chromium trioxide/ acetic acid or oxygen and potassium t-butoxide in t-butanol, provides compounds 6a and 6b, respectively, which are in equilibrium with the enol forms of compounds 25a and 25b, respectively. Compounds 5a and 5b can be prepared from compounds 25a and 25b, respectively, by O-alkylating or O-acylating using well-known synthetic methods.

12-Methoxypodocarpa-8,11,13-trieneoic acid (29) is a useful starting material for Diterpenoid Compounds 11a, 11b, 12a, and 12b (Schemes 4 and 5). With reference to Scheme 4, compounds 30 can be obtained by treating compound 29 with a strong base such as n-butyllithium followed by alkylation using an alkyl halide, aldehyde, ketone, ester or epoxide. The resulting compounds 30 can then be treated with lead tetraacetate and monoperphtalic acid to provide epoxides 31 (R. Cambie and T. Fullerton, *Aust. J. Chem.*, 24:2611 (1971)), which can then be treated with lithium diethylamide and n-lithioethelenediamine to yield the tricyclic compounds 32 (R. Cambie and T. Fullerton, *Aust. J. Chem.*, 24:2611 (1971)). Compounds 33 can then be obtained by oxidizing compounds 32 with a reagent such as chromium trioxide and sulphuric acid, forming an enolate from the resultant ketone using a basic solution such as potassium t-butoxide in t-butanol and quenching the enolate with an alkylating agent, such as methyliodide (B. Snider et al., *J. Org. Chem.*, 50:3659 (1985)). Reduction of compounds 33 with a metal such as palladium in a solvent/ acid mixture such as ethanol and acetic acid provides the tricyclic ketones 34 (H. Thompson et al., *J. Org. Chem.*, 41:2903 (1976)). Compounds such as 11a, where $R_5$=OMe, can be obtained by treating compounds 34 with lithium diisopropyl amide, followed by phenylselenium chloride, hydrogen peroxide and meta-chloroperoxybenzoic acid, further followed by oxidation using, for example, chromium trioxide/acetic acid or oxygen with potassium t-butoxide in t-butanol (M. Tius et al., *J. Am. Chem. Soc.*, 114:5959 (1992)). Oxidation of compounds 34 using chromium trioxide/acetic acid and oxygen with potassium t-butoxide in t-butanol provides 11b where $R_5$=$OCH_3$. Compounds 11a and 11b ($R_5$=OMe) are in equilibrium with triketo compounds 12a and 12b, respectively.

Scheme 5 depicts an alternative method useful for the preparation of Diterpenoid Compounds 11a, 11b, 12a, and 12b. For example, compounds 36 having $R_5$ functional groups other than —$OCH_3$ can be obtained by demethylating compound 30 with a reagent such as boron trichloride, treating the resultant phenoxide with triflic anhydride or any other suitable triflating agent, and then displacing the triflate with an organometallic reagent such as a boronate or a cuprate. The conversion of compounds 36 to Diterpenoid Compounds 11a, 11b, 12a, and 12b can be achieved using the same or similar synthetic methods as described in Scheme 4 for converting compounds 31 to those of formula 11a, 11b ($R_5$=OMe) and 12a, 12b ($R_5$=OMe)(R. Cambie and T. Fullerton, *Aust. J. Chem.*, 24:2611 (1971); M. Tius et al., *J. Am. Chem. Soc.*, 114:5959 (1992)).

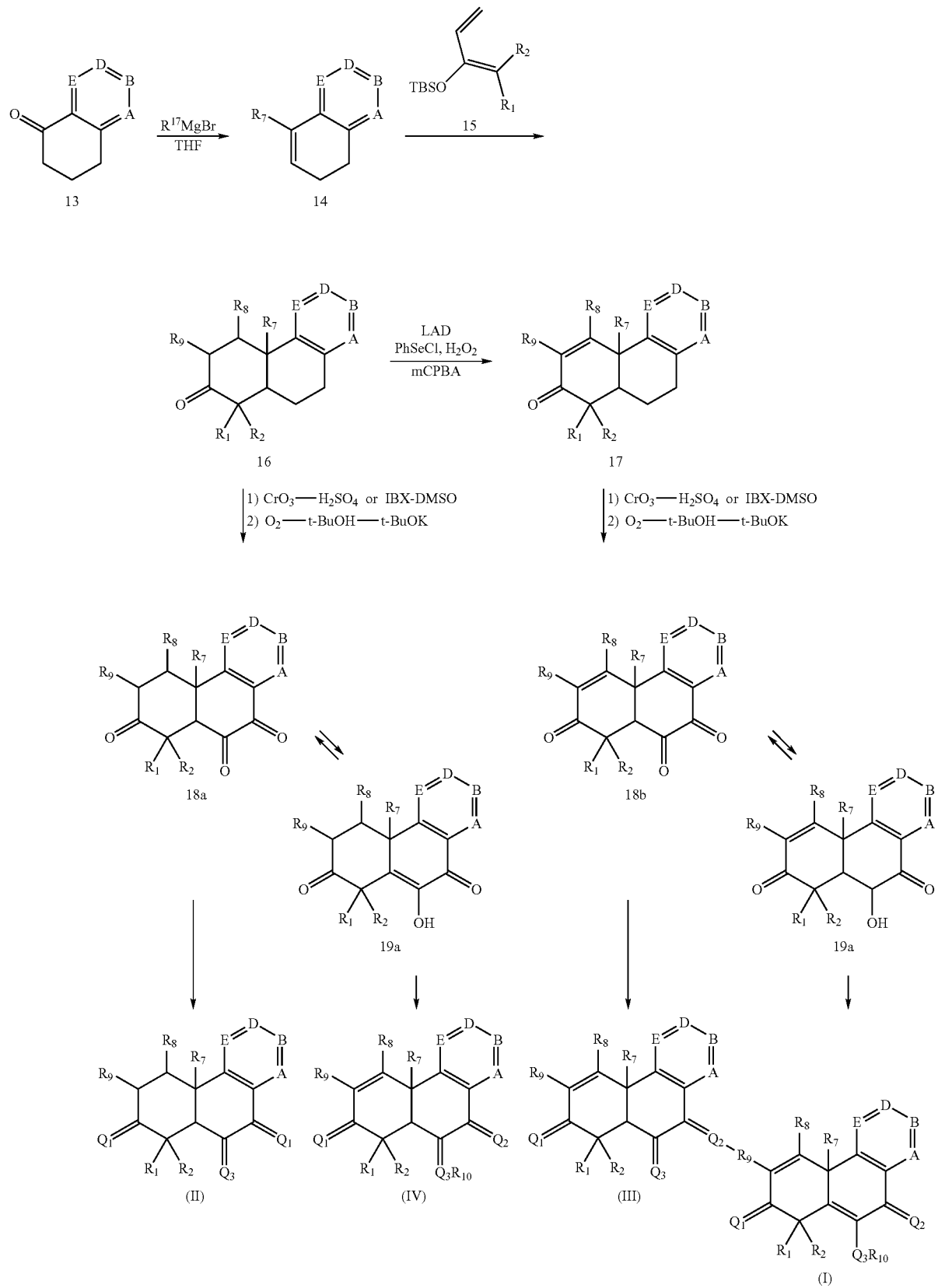
Scheme 1

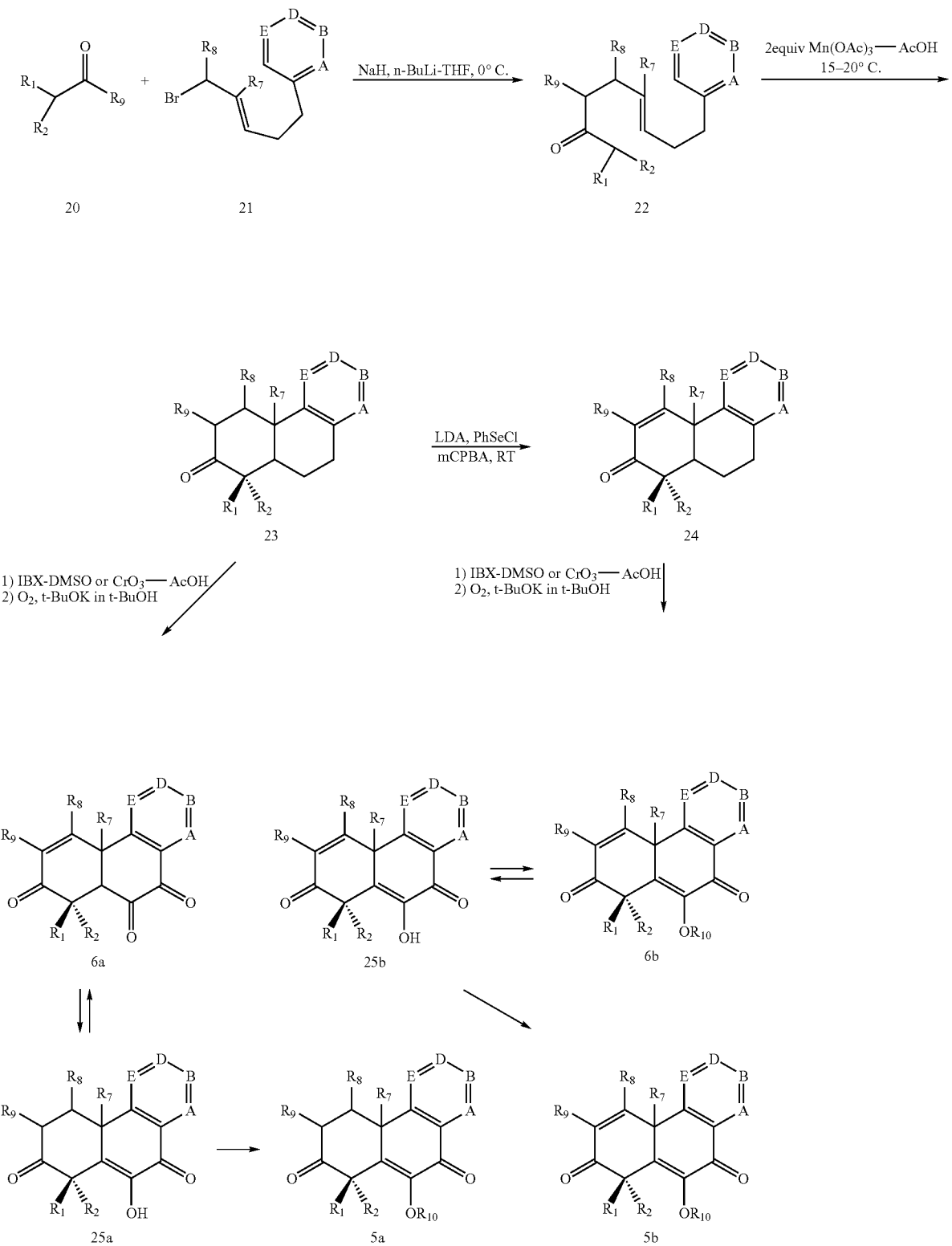

Scheme 3
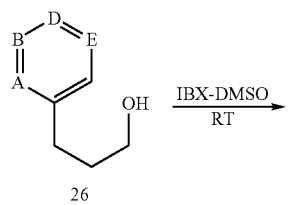
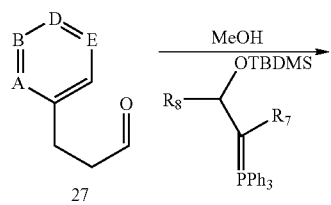
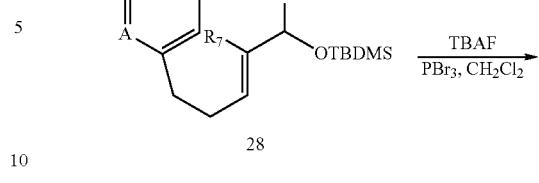
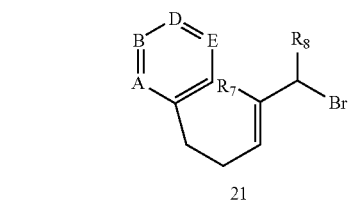
Scheme 4
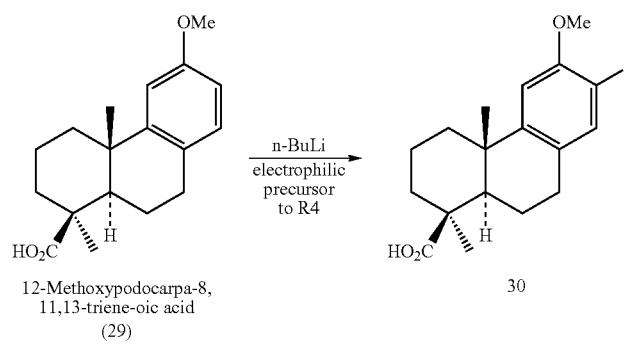
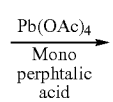
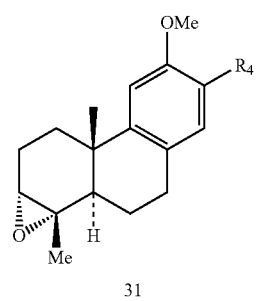
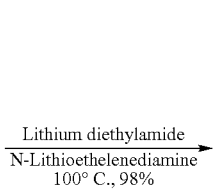
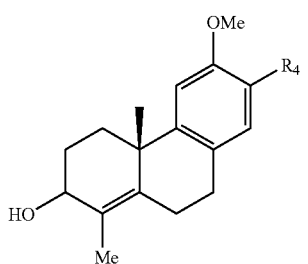
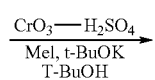
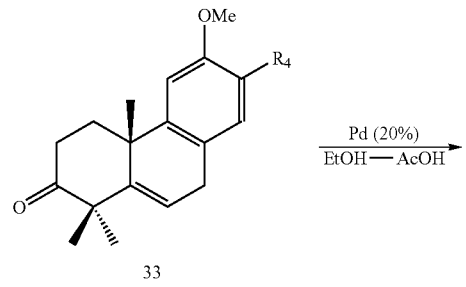

-continued
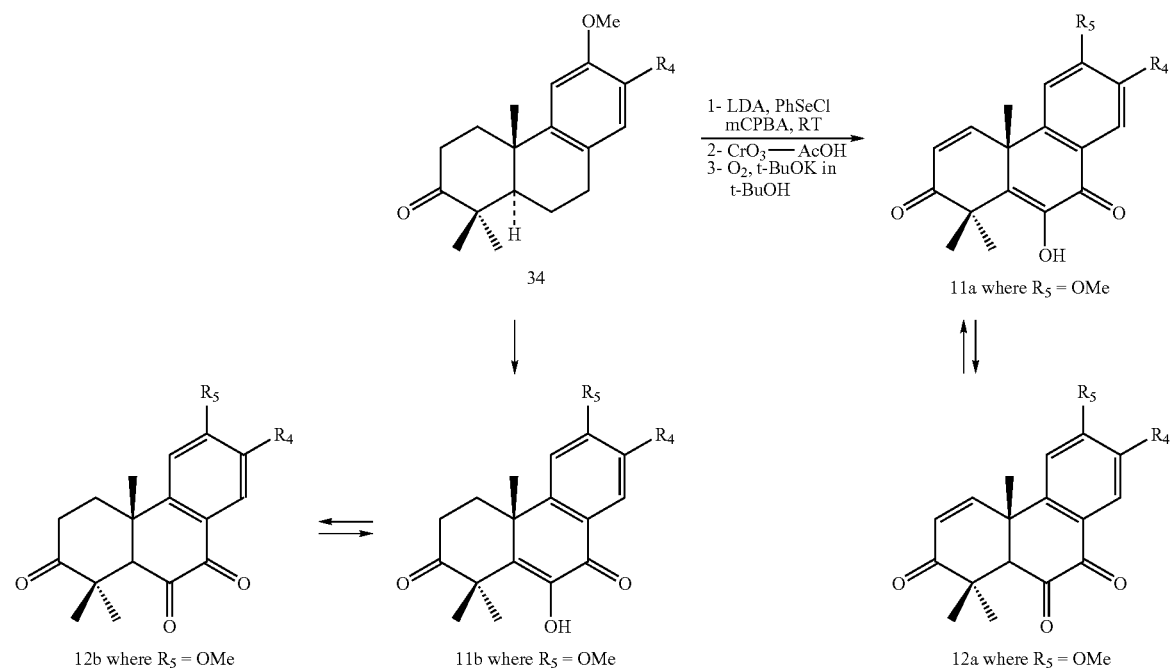
Scheme 5
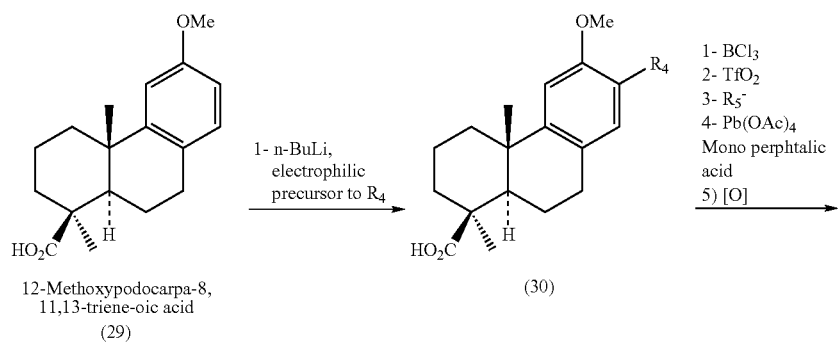
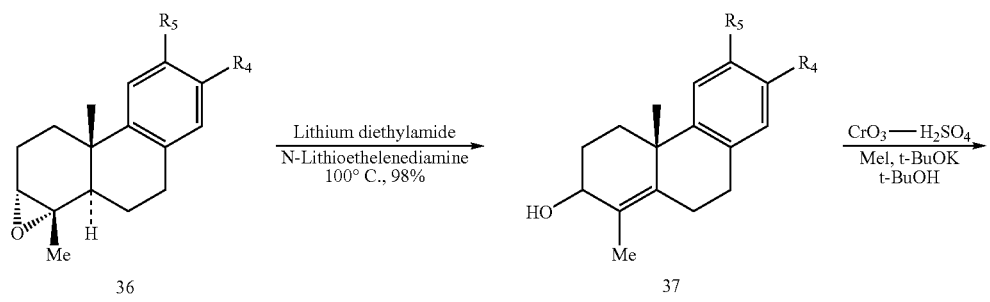

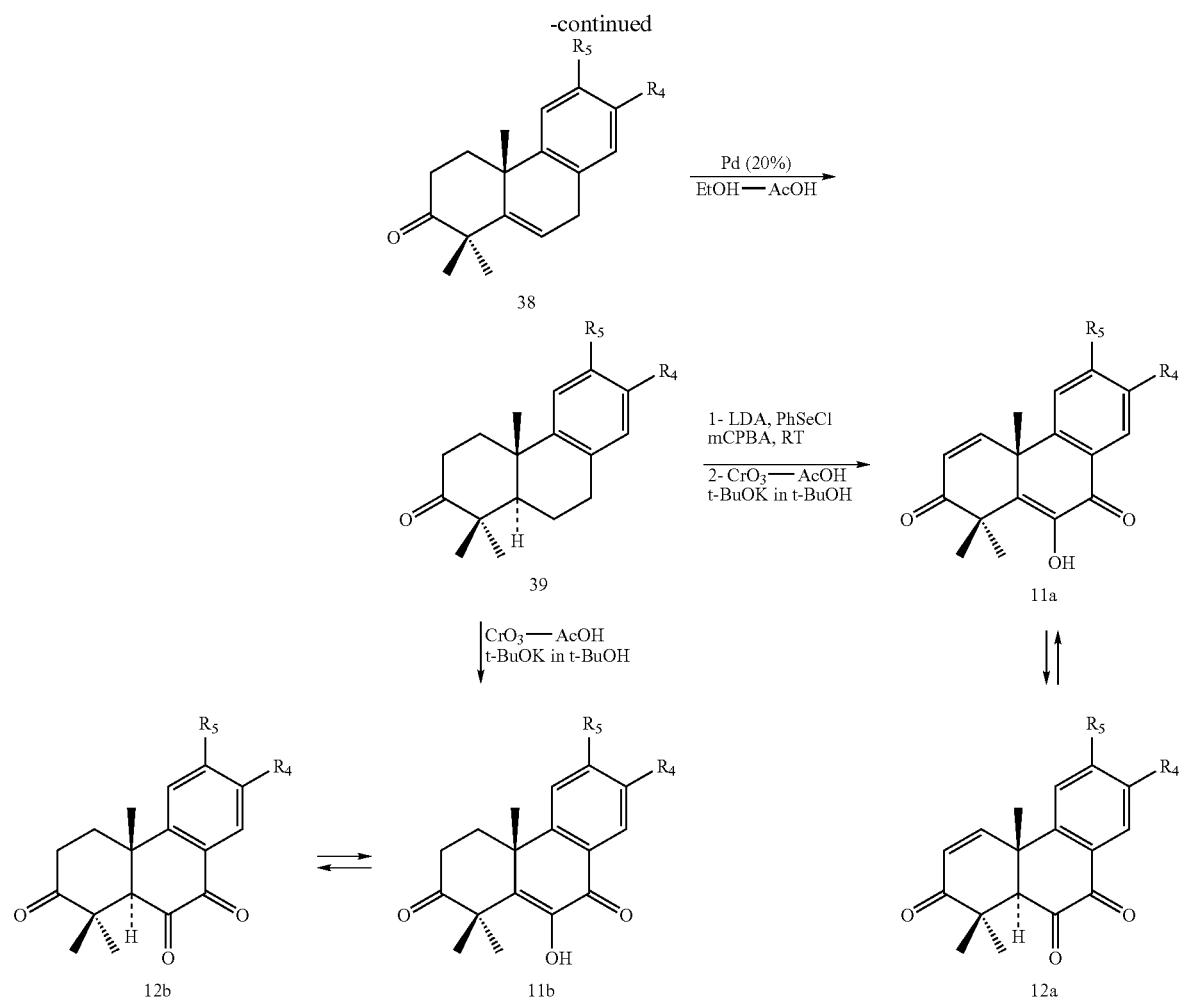
Synthesis of Compound 50
Compound 50 can be synthesized as illustrated in Scheme 6.
SCHEME 6
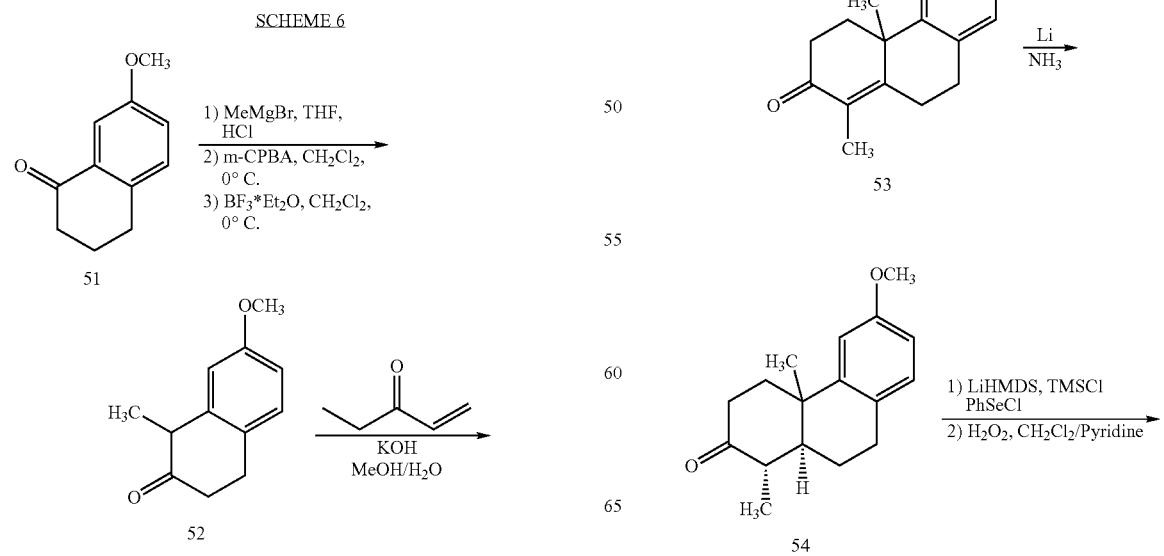

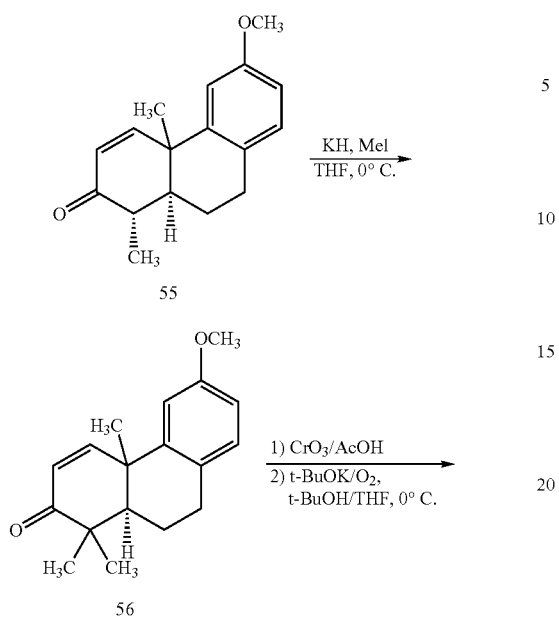
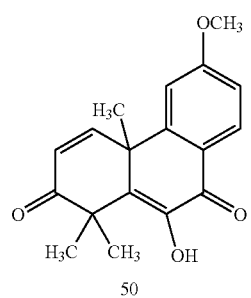
Compound 50a and Compound 50b can be synthesized as illustrated in Scheme 7.
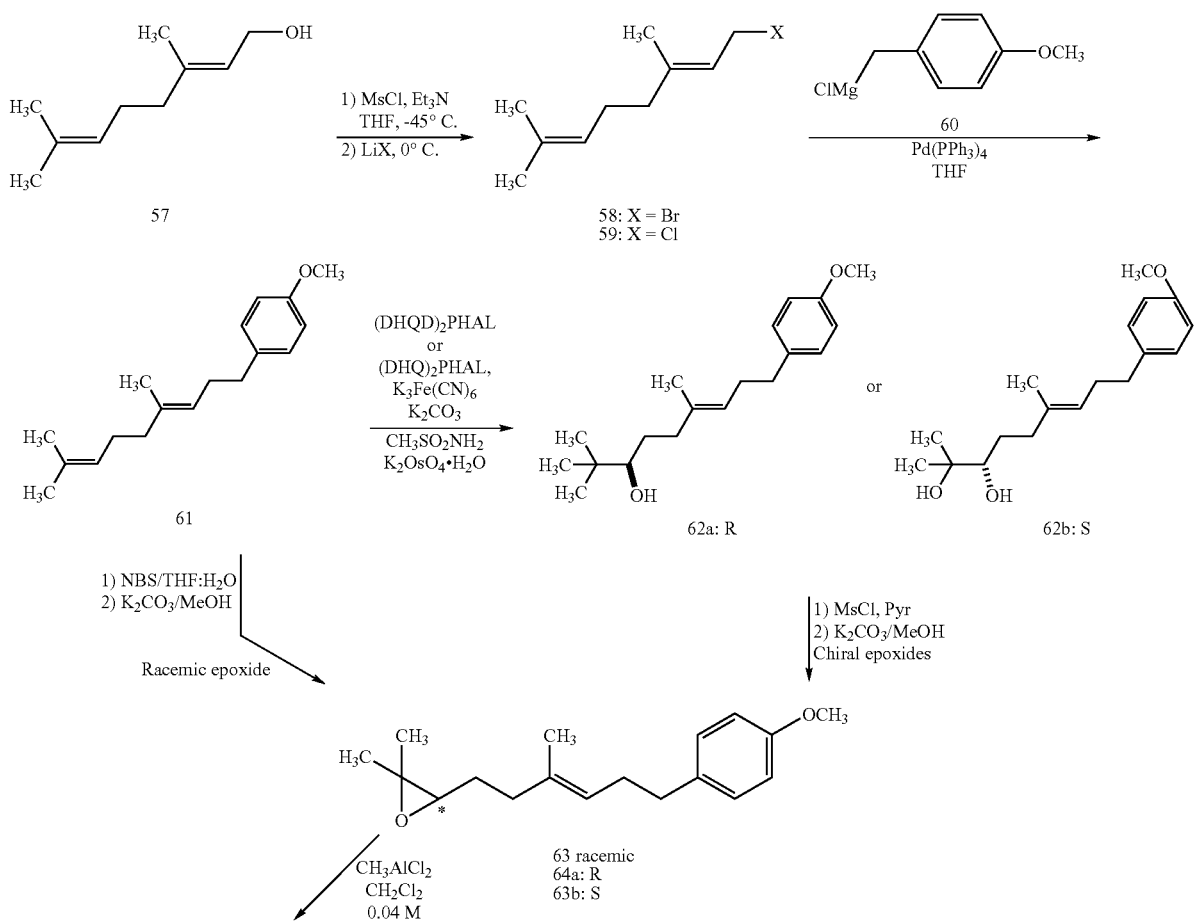

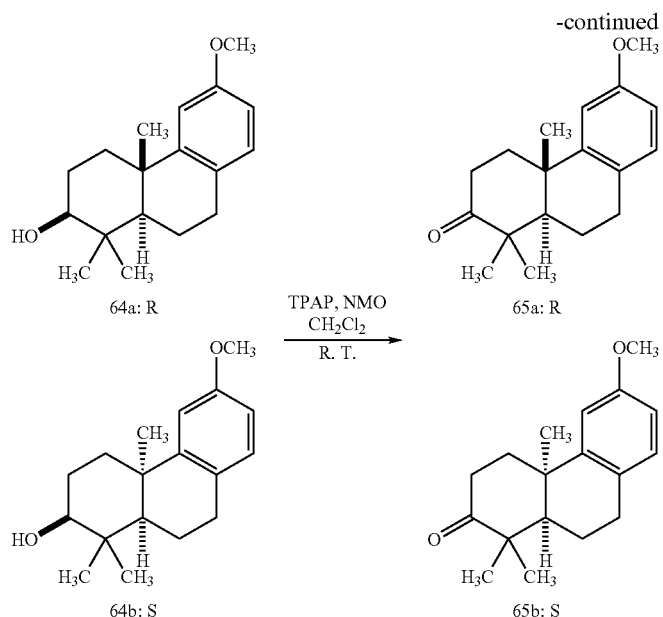
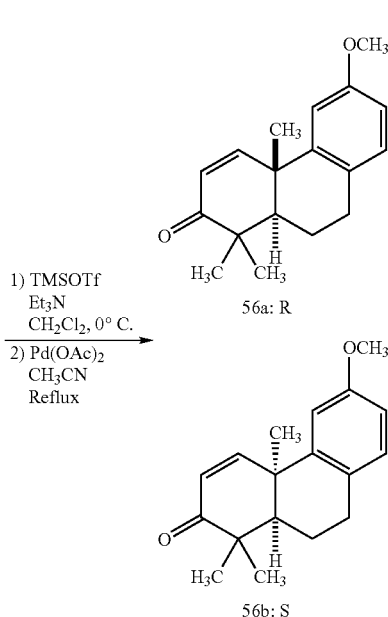
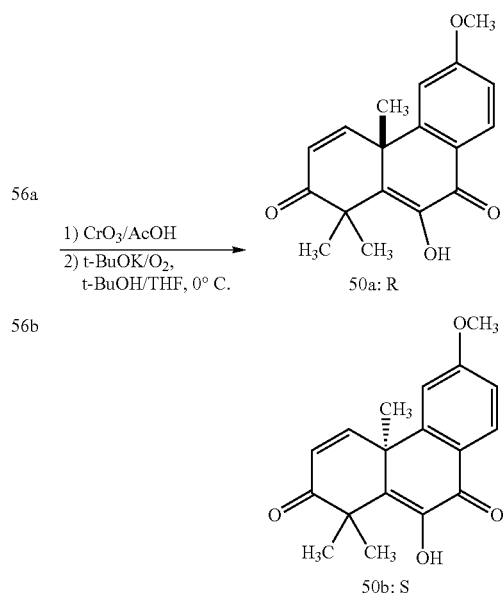

Synthesis of Compound of Formulas (Ib), (IIb) (IIIb), (IVb), (Vb), (VIb) and (VIIb)

In certain embodiments, compounds of Formulas (Ia), (IIa), (IIIa), (IVa), (Va), (VIa) and (VIIa) can be obtained by standard oxidization of compounds of Formulas (Ib), (IIb), (IIIb), (IVb), (Vb), (VIb) and (VIIb). In certain exemplary embodiments, compounds of Formulas (Ia), (IIa), (IIIa), (IVa), (Va), (VIa) and (VIIa) can be obtained by selectively oxidizing compounds of Formulas (Ib), (IIb), (IIIb), (IVb), (Vb), (VIb) and (VIIb). In certain, more specific embodiments, a compound of Formula (Ib), (IIb), (IIIb), (IVb), (Vb), (VIb) and (VIIb) with a carbonyl group at one or more of positions A, B, D and E can be obtained by oxidizing a compound of Formula (Ia), (IIa), (IIIa), (IVa), (Va), (VIa) or (VIIa) that has a COH at those positions where a carbonyl is desired.

5.10 Prodrugs

The present invention also provides prodrugs of the Diterpenoid Compounds of the invention. Illustrative prodrugs of the Diterpenoid Compounds of the invention are:

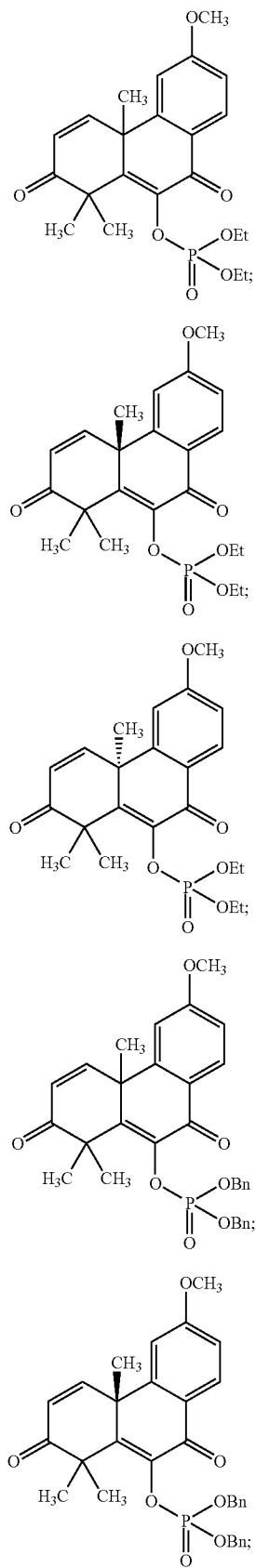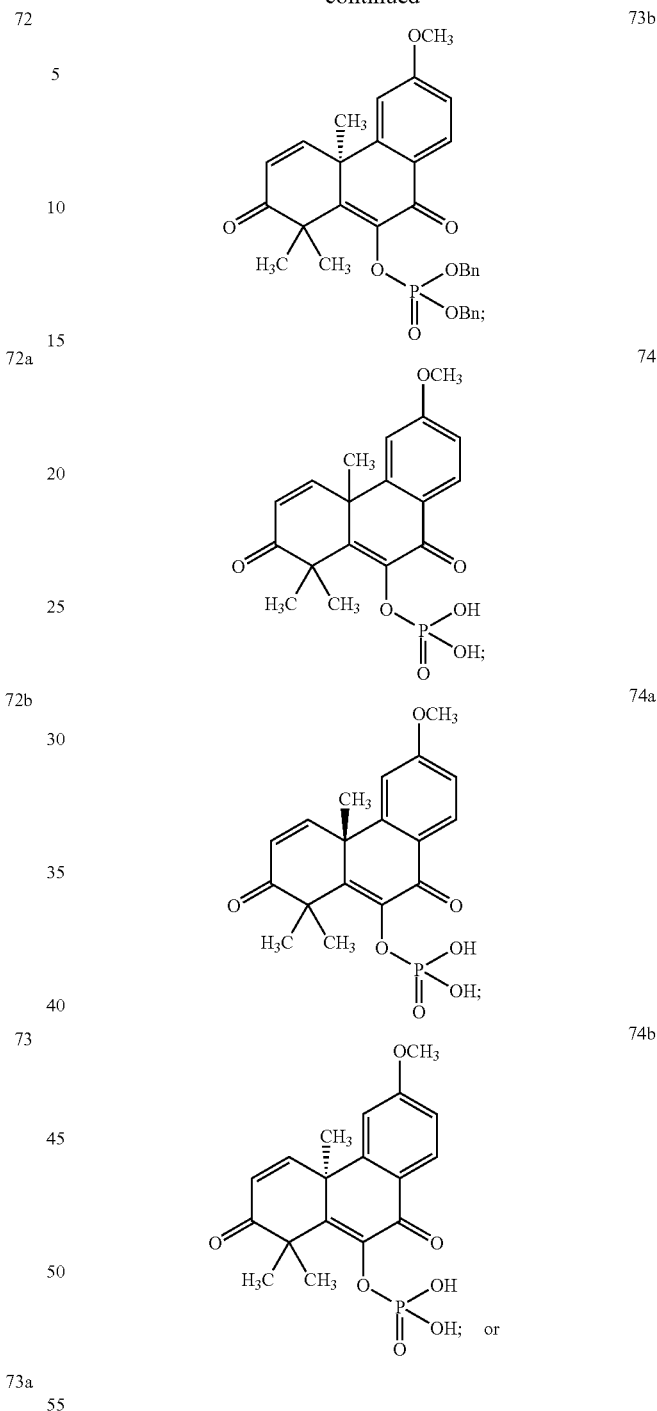

a pharmaceutically acceptable salt thereof (Bn is benzyl).

In certain embodiments, the invention provides methods for treating cancer in a patient, comprising administering to the patient an effective amount of a prodrug of a Diterpenoid Compound of the invention, e.g., Compound 72 or Compound 73 or Compound 74. A prodrug of a Diterpenoid Compound of the invention, e.g., Compound 72 or Compound 73 or Compound 74, is useful for treating or preventing cancer or neoplastic disease in a patient in need of such treatment or prevention. A prodrug of a Diterpenoid Compound of the invention, e.g., Compound 72 or Compound 73 or Compound 74, is also useful for inhibiting the growth of a cancer cell or neoplastic cell. A prodrug of a Diterpenoid Compound of the invention, e.g., Compound 72 or Compound 73 or Compound 74, is also useful for inducing cytotoxicity, e.g., through apoptosis, in a cancer cell or neoplastic cell. A prodrug of a Diterpenoid Compound of the invention, e.g., Compound 72 or Compound 73 or Compound 74, is further useful for treating or preventing a fungal infection. A prodrug of a Diterpenoid Compound of the invention, e.g., Compound 72 or Compound 73 or Compound 74, is also useful for inhibiting the growth of a fungus.

Illustrative methods for synthesizing Compound 72 or Compound 73 or Compound 74, respectively, are described in Example 6.5.

The present invention also provides prodrugs of the Diterpenoid Compounds of the invention. Prodrugs include derivatives of Diterpenoid Compounds that can hydrolyze, oxidize, or otherwise react under biological conditions (in vitro or in vivo) to provide an active Diterpenoid Compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, and biohydrolyzable phosphate analogues. In certain embodiments, prodrugs of Diterpenoid Compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of prodrugs* (H. Bundgaard ed., 1985, Harwood Academic Publishers Gmfh). Biohydrolyzable moieties of a Diterpenoid Compound (i) do not interfere with the biological activity of the compound but can confer upon that compound advantageous properties in vivo, such as uptake, duration of action, or onset of action; or (ii) are biologically inactive but are converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

5.11 Therapeutic/Prophylactic Administration and Compositions

Due to their activity, the Diterpenoid Compounds are advantageously useful in veterinary and human medicine. For example, the Diterpenoid Compounds are useful for treating or preventing cancer or neoplastic disease, inhibiting the growth of a cancer cell or neoplastic cell, inducing cytotoxicity, e.g., through apoptosis, in a cancer cell or neoplastic cell, treating or preventing a fungal infection, or inhibiting the growth of a fungus.

When administered to a patient, e.g., an animal for veterinary use or to a human for clinical use, or when made to contact a cell or tissue, the Diterpenoid Compounds can be in isolated and purified form.

The present compositions, which comprise a Diterpenoid Compound, can be administered by any convenient route, for example by infusion or bolus injection, by absorption through epithelial or mucocutaneous linings (e.g., oral mucosa, rectal and intestinal mucosa) and can be administered together with another active agent. Administration can be systemic or local. Various delivery systems are known, e.g., encapsulation in liposomes, microparticles, microcapsules, capsules, etc., and can be used to administer a Diterpenoid Compound. In certain embodiments, more than one Diterpenoid Compound is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The mode of administration can be left to the discretion of the practitioner, and can depend in-part upon the site of the medical condition (such as the site of cancer or neoplastic disease or fungal infection).

In specific embodiments, it might be desirable to administer one or more Diterpenoid Compounds locally to the area in need of treatment. This can be achieved, for example, and not by way of limitation, by local infusion during surgery, topical application, e.g., in conjunction with a wound dressing after surgery, by injection, by means of a catheter, by means of a suppository, by convection or by means of an implant, said implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue or fungal infection.

In certain embodiments, it might be desirable to administer one or more Diterpenoid Compounds by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Diterpenoid Compounds can be formulated as a suppository, with traditional binders and carriers such as triglycerides.

In another embodiment, the Diterpenoid Compounds can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the Diterpenoid Compounds can be delivered in a controlled-release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the Diterpenoid Compounds, thus requiring only a fraction of the systemic dose (see, e.g., Goodson, in Medical Applications of Controlled Release, supra, vol. 2, pp. 115–138 (1984)). Other controlled-release systems discussed in the review by Langer (Science 249:1527–1533 (1990)) can be used.

The present compositions comprise an effective amount of a Diterpenoid Compound, which can be in isolated and purified form, together with a suitable amount of a pharmaceutically acceptable carrier so as to provide a useful form for administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a Diterpenoid Compound is administered. Such pharmaceutical carriers can be liquids, such as water and oils, including those of petroleum, animal, vegetable or synthetic origin, such as peanut oil, soybean oil, mineral oil, sesame oil, polymethylated castor oil (CREMAPHOR EL) and the like. The pharmaceutical carriers can be saline, gum acacia, gelatin, starch paste, talc, keratin, colloidal silica, urea, and the like. In addition, auxiliary, stabilizing, thickening, lubricating and coloring agents can be used. When administered to a patient, the Diterpenoid Compounds and pharmaceutically acceptable carriers can be sterile. Water is a useful carrier when the Diterpenoid Compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

In one embodiment, the Diterpenoid Compounds are formulated in accordance with routine procedures as a pharmaceutical composition adapted for intravenous administration to human beings. Typically, Diterpenoid Compounds intended for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the Diterpenoid Compound is to be administered by infusion, it can be dispensed, for example, with an infusion bottle containing sterile pharmaceutical grade water or saline. Where the Diterpenoid Compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered Diterpenoid Compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard carriers such as mannitol, lactose, starch, magnesium stearate, sodium saccharine, cellulose, or magnesium carbonate. Such carriers can be of pharmaceutical grade.

The effective amount of the Diterpenoid Compound depends on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable effective amounts for intravenous administration generally range from about 10 micrograms to about 1 gram per kilogram body weight, in one embodiment from about 20 micrograms to about 500 micrograms, about 400 micrograms to about 2 milligrams, about 1 milligram to about 5 milligram, about 2 milligram to about 20 milligram, about 10 milligram to about 60 milligram, about 50 milligram to about 200 milligram, about 100 milligram to about 500 milligram, or about 200 milligram to about 800 milligram of Diterpenoid Compound per kilogram body weight. In specific embodiments of the invention, the effective amount for an i.v. dose ranges from about 10 to about 40, about 40 to about 60, about 60 to about 100, or about 100 to about 200 micrograms per kilogram body weight. In other embodiments, the effective amount for an i.v. dose ranges from about 75 to about 150, about 150 to about 250, about 250 to about 375 or about 375 to about 500 or about 400 to about 800 micrograms per kilogram body weight. In specific embodiments of the invention, the effective amount for an i.v. dose ranges from about 0.5 to about 2, from about 1 to about 10, from about 10 to about 40, about 40 to about 60, about 60 to about 100, or about 100 to about 200 milligrams per kilogram body weight. In other embodiments, the effective amount for an i.v. dose ranges from about 75 to about 150, about 150 to about 250, about 250 to about 375 or about 375 to about 500 milligrams per kilogram body weight. Suitable effective amounts for intranasal administration generally range from about 0.01 pg/kg body weight to about 1 mg/kg, from about 0.5 mg/kg to about 800 mg/kg body weight. Suppositories generally contain an effective amount in the range of about 0.5% to about 10% by weight. Oral compositions can contain from about 10% to about 95% of Diterpenoid Compound. In specific embodiments of the invention, suitable effective amounts for oral administration generally range from about 0.1 micrograms to about 10 milligrams, from about 0.75 micrograms to about 1 milligram, from about 1 to about 500 micrograms, from about 200 micrograms to about 2 milligrams, from about 1 milligram to about 10 milligram, from about 5 milligram to about 50 milligram, from about 20 milligram to about 200 milligram, or from about 100 milligram to about 800 milligram of Diterpenoid Compound per kilogram body weight. In specific embodiments, the effective amount for an oral dose ranges from about 1 to about 10, about 10 to about 30, about 30 to about 90, or about 90 to about 150 micrograms per kilogram body weight. In other embodiments, the oral dose ranges from about 150 to about 250, about 250 to about 325, about 325 to about 450 or about 450 to about 1000 micrograms per kilogram body weight. In other embodiments, the oral dose ranges from about 150 to about 250, about 250 to about 325, about 325 to about 450 or about 450 to about 1000 milligrams per kilogram body weight. Effective amounts can be extrapolated from dose-response curves derived from in vitro or animal model test systems. Such animal models and systems are well known in the art. In one embodiment, for testing the effectiveness of a Diterpenoid Compound in an in vitro cell culture, concentrations from about 0.1 micromolar to about 10 micromolar, from about 0.2 micromolar to about 10 micromolar, from about 0.5 micromolar to about 5 micromolar, or from about 0.2 micromolar to about 5 micromolar can be used.

The invention also provides pharmaceutical packs or kits comprising one or more containers containing one or more Diterpenoid Compounds. Optionally associated with such container(s) can be instructions for use of one or more Diterpenoid Compounds or a notice in the form prescribed by a governmental agency regulating the manufacture, use or sale of pharmaceuticals or biological products, which notice reflects approval by the agency of manufacture, use or sale for human administration. In one embodiment, e.g., when administered for the treatment or prevention of cancer, the kit can also contain one or more chemotherapeutic agents useful for treating cancer or a neoplastic disease to be administered prior to, subsequent to, or in combination with a Diterpenoid Compound. In another embodiment, e.g., when administered for the treatment or prevention of a fungal infection, the kit can also contain one or more other anti-fungal agents to be administered prior to, subsequent to or in combination with a Diterpenoid Compound. Such other anti-fungal agents include, but are not limited to, ketoconazole, itraconazole, amphotericin B, polyoxines, nikkomycines, carboxyamides, aromatic carbohydrates, carboxines, morpholines, inhibitors of sterol biosynthesis, and organophosphorus compounds.

The Diterpenoid Compounds can be assayed in vitro, and then in vivo, for the desired therapeutic or prophylactic activity, prior to use in humans. For example, in vitro assays can be used to determine whether administration of a specific Diterpenoid Compound or combination of Diterpenoid Compounds is preferred.

In one embodiment, a patient-tissue sample is grown in culture, and contacted or otherwise administered with a Diterpenoid Compound, and the effect of the Diterpenoid Compound upon the tissue sample is observed and compared with a non-contacted tissue. In other embodiments, a cell culture model is used in which the cells of the cell culture are contacted or otherwise administered with a Diterpenoid Compound, and the effect of the Diterpenoid Compound upon the tissue sample is observed and compared with a non-contacted cell culture. Generally, a lower level of proliferation or survival of the contacted cells compared to the non-contracted cells indicates that the Diterpenoid Compound is effective to treat or prevent cancer or a neoplastic disease. The Diterpenoid Compounds can also be demonstrated to be effective and safe using animal model systems.

In one embodiment, a fungus sample from an infected patient is grown in culture and contacted or otherwise administered with a Diterpenoid Compound, and the effect of the Diterpenoid Compound upon the growth of the fungus is observed and compared with a non-contacted tissue. Generally, a lower level of proliferation or survival of the contacted fungus compared to the non-contacted fungus indicates that the Diterpenoid Compound is effective to treat or prevent the fungal infection. The Diterpenoid Compounds can also be demonstrated to be effective and safe using animal model systems.

Other methods will be known to the skilled artisan and are within the scope of the invention.

5.12 Inhibition of Cancer and Neoplastic Cells and Disease

The Diterpenoid Compounds can be shown to inhibit tumor cell proliferation, cell transformation or tumorigenesis in vitro and in vivo using a variety of assays known in the art, or described herein. Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz Inc.). mRNA can be quantitated using methods that are well known and routine in the art, for example, using northern analysis, RNase protection, the polymerase chain reaction in connection with the reverse transcription. Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

The present invention provides for cell cycle and cell proliferation analysis using a variety of techniques known in the art, including but not limited to the following:

As one example, bromodeoxyuridine (BRDU) incorporation can be used as an assay to identify proliferating cells. The BRDU assay identifies a cell population undergoing DNA synthesis by incorporation of BRDU into newly synthesized DNA. Newly synthesized DNA can then be detected using an anti-BRDU antibody (see Hoshino et al., 1986, Int. J. Cancer 38, 369; Campana et al., 1988, J. Immunol. Meth. 107, 79).

Cell proliferation can also be examined using (3H)-thymidine incorporation (see e.g., Chen, J., 1996, Oncogene 13:1395–403; Jeoung, J., 1995, J. Biol. Chem. 270:18367–73). This assay allows for quantitative characterization of S-phase DNA synthesis. In this assay, cells synthesizing DNA will incorporate ($^3$H)-thymidine into newly synthesized DNA. Incorporation can then be measured by standard techniques in the art such as by counting of radioisotope in a Scintillation counter (e.g. Beckman LS 3800 Liquid Scintillation Counter).

Detection of proliferating cell nuclear antigen (PCNA) can also be used to measure cell proliferation. PCNA is a 36 kilodalton protein whose expression is elevated in proliferating cells, particularly in early G1 and S phases of the cell cycle and therefore can serve as a marker for proliferating cells. Positive cells can be identified by immunostaining using an anti-PCNA antibody (see Li et al., 1996, Curr. Biol. 6:189–199; Vassilev et al., 1995, J. Cell Sci. 108:1205–15).

Cell proliferation can be measured by counting samples of a cell population over time (e.g. daily cell counts). Cells can be counted using a hemacytometer and light microscopy (e.g. HyLite hemacytometer, Hausser Scientific). Cell number can be plotted against time in order to obtain a growth curve for the population of interest. In one embodiment, cells counted by this method are first mixed with the dye Trypan-blue (Sigma), such that living cells exclude the dye, and are counted as viable members of the population.

DNA content and/or mitotic index of the cells can be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) exhibit a ploidy value higher than 2N and up to 4N DNA content. Ploidy value and cell-cycle kinetics can be further measured using propidum iodide assay (see e.g. Turner, T., et al., 1998, Prostate 34:175–81). Alternatively, the DNA ploidy can be determined by quantitation of DNA Feulgen staining (which binds to DNA in a stoichiometric manner) on a computerized microdensitometrystaining system (see e.g., Bacus, S., 1989, Am. J. Pathol. 135:783–92). In an another embodiment, DNA content can be analyzed by preparation of a chromosomal spread (Zabalou, S., 1994, Hereditas. 120: 127–40; Pardue, 1994, Meth. Cell Biol. 44:333–351).

The expression of cell-cycle proteins (e.g., CycA, CycB, CycE, CycD, cdc2, Cdk4/6, Rb, p21, and p27) provide information relating to the proliferative state of a cell or population of cells. For example, identification in an anti-proliferation signaling pathway can be indicated by the induction of p21$^{ciP1}$. Increased levels of p21 expression in cells result in delayed entry into G1 of the cell cycle (Harper et al., 1993, Cell 75:805–816; Li et al., 1996, Curr. Biol. 6:189–199). p21 induction can be identified by immunostaining using a specific anti-p21 antibody available commercially (e.g. Santa Cruz). Similarly, cell-cycle proteins can be examined by Western blot analysis using commercially available antibodies. In another embodiment, cell populations are synchronized prior to detection of a cell cycle protein. Cell cycle proteins can also be detected by FACS (fluorescence-activated cell sorter) analysis using antibodies against the protein of interest.

Detection of changes in length of the cell cycle or speed of cell cycle can also be used to measure inhibition of cell proliferation by the Diterpenoid Compounds. In one embodiment the length of the cell cycle is determined by the doubling time of a population of cells (e.g., using cells contacted or not contacted with one or more Diterpenoid Compounds). In another embodiment, FACS analysis is used to analyze the phase of cell cycle progression, or purify G1, S, and G2/M fractions (see e.g., Delia, D. et al., 1997, Oncogene 14:2137–47).

Lapse of cell cycle checkpoint(s), and/or induction of cell cycle checkpoint(s), can be examined using the methods described herein, or by any method known in the art. Without limitation, a cell cycle checkpoint is a mechanism that ensures that the different steps of cell division occur in a particular order. Checkpoint genes are defined by mutations that allow late events to occur without prior completion of an early event (Weinert, T., and Hartwell, L., 1993, Genetics, 134:63–80). Induction or inhibition of cell cycle checkpoint genes can be assayed, for example, by Western blot analysis, or by immunostaining, for example. Lapse of cell cycle checkpoints can be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved in detecting post-translational modifications (e.g. phosphorylation) by any method known in the art. For example, antibodies that detect phosphorylated tyrosine residues are commercially available, and can be used in Western blot analysis to detect proteins with such modifications. In another example, modifications such as myristylation, can be detected on thin layer chromatography or reverse phase h.p.l.c. (see e.g., Glover, C., 1988, Biochem. J. 250:485–91; Paige, L., 1988, Biochem J.; 250:485–91).

Activity of signaling and cell cycle proteins and/or protein complexes is often mediated by a kinase activity. The present invention provides for analysis of kinase activity by assays such as the histone H1 assay (see e.g., Delia, D. et al., 1997, Oncogene 14:2137–47).

The Diterpenoid Compounds can also be demonstrated to alter cell proliferation in cultured cells in vitro using methods which are well known in the art. Specific examples of cell culture models include, but are not limited to, for lung cancer, primary rat lung tumor cells (Swafford et al., 1997, Mol. Cell. Biol., 17:1366–1374) and large-cell undifferentiated cancer cell lines (Mabry et al., 1991, Cancer Cells, 3:53–58); colorectal cell lines for colon cancer (Park and Gazdar, 1996, J. Cell Biochem. Suppl. 24:131–141); multiple established cell lines for breast cancer (Hambly et al., 1997, Breast Cancer Res. Treat. 43:247–258; Gierthy et al., 1997, Chemosphere 34:1495–1505; Prasad and Church, 1997, Biochem. Biophys. Res. Commun. 232:14–19); a number of well-characterized cell models for prostate cancer (Webber et al., 1996, Prostate, Part 1, 29:386–394; Part 2, 30:58–64; and Part 3, 30:136–142; Boulikas, 1997, Anticancer Res. 17:1471–1505); for genitourinary cancers, continuous human bladder cancer cell lines (Ribeiro et al., 1997, Int. J. Radiat. Biol. 72:11–20); organ cultures of transitional cell carcinomas (Booth et al., 1997, Lab Invest. 76:843–857) and rat progression models (Vet et al., 1997, Biochim. Biophys Acta 1360:39–44); and established cell lines for leukemias and lymphomas (Drexler, 1994, Leuk. Res. 18:919–927, Tohyama, 1997, Int. J. Hematol. 65:309–317).

The Diterpenoid Compounds can also be demonstrated to inhibit cell transformation (or progression to malignant phenotype) in vitro. In this embodiment, cells with a transformed cell phenotype are contacted with one or more Diterpenoid Compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology*, 3d Ed., John Wiley & Sons, New York, pp. 436–446).

Loss of invasiveness or decreased adhesion can also be used to demonstrate the anti-cancer effects of the Diterpenoid Compounds. For example, an aspect of the formation of a metastatic cancer is the ability of a precancerous or cancerous cell to detach from primary site of disease and establish a novel colony of growth at a secondary site. The ability of a cell to invade peripheral sites reflects its potential for a cancerous state. Loss of invasiveness can be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278:1464–66).

Loss of invasiveness can further be examined by inhibition of cell migration. A variety of 2-dimensional and 3-dimensional cellular matrices are commercially available (Calbiochem-Novabiochem Corp. San Diego, Calif.). Cell migration across or into a matrix can be examined using microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464–66).

Alternatively, loss of invasiveness can be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated can then be correlated with invasiveness (see e.g., Ohnishi, T., 1993, Biochem. Biophys. Res. Commun. 193:518–25).

The Diterpenoid Compounds can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in *Harrison's Principals of Internal Medicine*, 13*th Edition*, Isselbacher et al., eds., McGraw-Hill, New York, p. 1814, and Lovejoy et al., 1997, J. Pathol. 181:130–135). Specific examples include for lung cancer, transplantation of tumor nodules into rats (Wang et al., 1997, Ann. Thorac. Surg. 64:216–219) or establishment of lung cancer metastases in SCID mice depleted of NK cells (Yono and Sone, 1997, Gan To Kagaku Ryoho 24:489–494); for colon cancer, colon cancer transplantation of human colon cancer cells into nude mice (Gutman and Fidler, 1995, World J. Surg. 19:226–234), the cotton top tamarin model of human ulcerative colitis (Warren, 1996, Aliment. Pharmacol. Ther. 10 Supp 12:45–47) and mouse models with mutations of the adenomatous polyposis tumor suppressor (Polakis, 1997, Biochim. Biophys. Acta 1332:F127–F147); for breast cancer, transgenic models of breast cancer (Dankort and Muller, 1996, Cancer Treat. Res. 83:71–88; Amundadittir et al., 1996, Breast Cancer Res. Treat. 39:119–135) and chemical induction of tumors in rats (Russo and Russo, 1996, Breast Cancer Res. Treat. 39:7–20); for prostate cancer, chemically-induced and transgenic rodent models, and human xenograft models (Royai et al., 1996, Semin. Oncol. 23:35–40); for genitourinary cancers, induced bladder neoplasm in rats and mice (Oyasu, 1995, Food Chem. Toxicol 33:747–755) and xenografts of human transitional cell carcinomas into nude rats (Jarrett et al., 1995, J. Endourol. 9:1–7); and for hematopoietic cancers, transplanted allogeneic marrow in animals (Appelbaum, 1997, Leukemia 11 (Suppl. 4):S15–S17). Further, general animal models applicable to many types of cancer have been described, including, but not restricted to, the p53-deficient mouse model (Donehower, 1996, Semin. Cancer Biol. 7:269–278), the Min mouse (Shoemaker et al., 1997, Biochem. Biophys. Acta, 1332:F25–F48), and immune responses to tumors in rat (Frey, 1997, Methods, 12:173–188).

For example, a Diterpenoid Compound can be administered to a test animal, preferably a test animal predisposed to develop a type of tumor, and the test animal subsequently examined for a decreased incidence of tumor formation in comparison with controls not administered the Diterpenoid Compound. Alternatively, a Diterpenoid Compound can be administered to a test animal having a tumor (e.g., animals in which tumors have been induced by introduction of malignant, neoplastic, or transformed cells, or by administration of a carcinogen), and the tumors in the test animals can be subsequently examined for tumor regression and compared with controls that were not administered with the Diterpenoid Compound.

The Diterpenoid Compounds are useful for inhibiting the growth of a cancer cell or neoplastic cell and for inducing cytotoxicity, e.g., through apoptosis, of a cancer cell or neoplastic cell in vivo. Inhibiting the growth of a cancer cell or neoplastic cell and inducing cytotoxicity, e.g., through apoptosis, in a cancer cell or neoplastic cell in vivo is useful for treating, preventing and inhibiting the growth of a cancer. The Diterpenoid Compounds are useful for inhibiting the growth of a cancer cell or neoplastic cell and for inducing cytotoxicity, e.g., through apoptosis, in a cancer cell or neoplastic cell in vitro. Inhibiting the growth of a cancer cell or neoplastic cell and inducing cytotoxicity, e.g., through apoptosis, in a cancer cell or neoplastic cell in vitro is useful for assays to determine optimal concentration ranges of effectiveness of a Diterpenoid Compound.

5.12.1 Inducing Apoptosis in a Cancer Cell or a Neoplastic Cell

Without being bound by theory, apoptosis is a morphologically and biochemically distinct form of cell death that occurs in response to a diverse range of stimuli, including irradiation and activation of death receptors such as Fas and the tumor necrosis factor receptor. Neoplastic transformation or cancerous growth of a cell can trigger apoptosis of that cell. Impaired apoptosis is therefore a significant factor in the aetiology of cancer and neoplastic diseases.

Morphologic criteria that can be used to describe apoptotic cells include condensation and margination of chromatin, cytoplasmic vacuolization, cellular shrinkage, increase in cellular density, nuclear fragmentation and apoptotic body formation.

Without being bound by theory, Applicants believe that the Diterpenoid Compounds induce apoptosis in a cancer cell or in a neoplastic cell. Moreover, without being bound by theory, Applicants believe that Diterpenoid Compounds induce apoptosis selectively in a cancer cell or in a neoplastic cell, relative to a non-cancer cell or non-neoplastic cell. In one embodiment, a Diterpenoid Compound induces apoptosis with at least 2-fold selectivity in a cancer cell or in a neoplastic cell, relative to a non-cancer cell or non-neoplastic cell. In certain embodiments, a Diterpenoid Compound induces apoptosis with at least 5-fold, 10-fold, 15-fold, 20-fold, 25-fold, 50-fold, 75-fold, 100-fold, 150-fold, 200-fold or 250-fold selectivity in a cancer cell or in a neoplastic cell, relative to a non-cancer cell or non-neoplastic cell. In certain embodiments, a Diterpenoid Compound induces apoptosis with at most 5-fold, 10-fold, 15-fold, 20-fold, 25-fold, 50-fold, 75-fold, 100-fold, 150-fold, 200-fold or 250-fold selectivity in a cancer cell and/or in a neoplastic cell, relative to a non-cancer cell or non-neoplastic cell. When selectivity in a cancer cell or neoplastic cell is n-fold, relative to a non-cancer or non-neoplastic cell, a Diterpenoid Compound induces apoptosis in n-times as many cancer cells or neoplastic cells than non-cancer cells or non-neoplastic cells.

Without being bound by theory, inducing apoptosis selectively in cancer cells or in neoplastic cells is useful for treating cancer or a neoplastic disease in a patient.

5.12.2 Treatment or Prevention of Cancer or a Neoplastic Disease in Combination with Chemotherapy or Radiotherapy Cancer or a neoplastic disease, including, but not limited to, neoplasms, tumors, metastases, or any disease or disorder characterized by uncontrolled cell growth, can be treated or prevented by administration of an effective amount of a Diterpenoid Compound.

In certain embodiments, the present methods for treating or preventing cancer or a neoplastic disease comprise administering an effective amount of a Diterpenoid Compound and another active agent, such as a chemotherapeutic or anti-cancer agent, including, but not limited to, methotrexate, taxol, mercaptopurine, thioguanine, hydroxyurea, cytarabine, cyclophosphamide, ifosfamide, nitrosoureas, Cis-platin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In another embodiment, the other chemotherapeutic or anti-cancer agent includes, but is not limited to, those listed in Table 1.

TABLE 1

| CHEMOTHERAPEUTICS AND OTHER ANTI-CANCER AGENTS | |
|---|---|
| Radiation: | γ-radiation |
| Alkylating agents | |
| Nitrogen mustards: | cyclophosphamide |
|  | Ifosfamide |
|  | trofosfamide |
|  | Chlorambucil |
| Nitrosoureas: | carmustine (BCNU) |
|  | Lomustine (CCNU) |
| Alkylsulphonates: | busulfan |
|  | Treosulfan |
| Triazenes: | Dacarbazine |

TABLE 1-continued

| CHEMOTHERAPEUTICS AND OTHER ANTI-CANCER AGENTS | |
|---|---|
| Platinum containing compounds: | Cisplatin |
|  | carboplatin |
| Plant Alkaloids | |
| Vinca alkaloids: | vincristine |
|  | Vinblastine |
|  | Vindesine |
|  | Vinorelbine |
| Taxoids: | paclitaxel |
|  | Docetaxol |
| DNA Topoisomerase Inhibitors | |
| Epipodophyllins: | etoposide |
|  | Teniposide |
|  | Topotecan |
|  | 9-aminocamptothecin |
|  | campto irinotecan |
|  | crisnatol |
| mytomycins: | |
| mytomycin C | Mytomycin C |
| Anti-metabolites | |
| Anti-folates: | |
| DHFR inhibitors: | methotrexate |
|  | Trimetrexate |
| IMP dehydrogenase Inhibitors: | mycophenolic acid |
|  | Tiazofurin |
|  | Ribavirin |
|  | EICAR |
| Ribonucleotide reductase Inhibitors: | hydroxyurea |
|  | deferoxamine |
| Pyrimidine analogs: | |
| Uracil analogs 5-Fluorouracil | Floxuridine |
|  | Doxifluridine |
|  | Ratitrexed |
| Cytosine analogs | cytarabine (ara C) |
|  | Cytosine arabinoside |
|  | fludarabine |
| Purine analogs: | mercaptopurine |
|  | Thioguanine |
| Hormonal therapies: | |
| Receptor antagonists: | Anti-estrogens Tamoxifen |
|  | Raloxifene |
|  | megestrol |
| LHRH agonists: | goscrclin |
|  | Leuprolide acetate |
| Anti-androgens: | flutamide |
|  | bicalutamide |
| Retinoids/Deltoids | |
| Vitamin D3 analogs: | EB 1089 |
|  | CB 1093 |
|  | KH 1060 |
| Photodyamic therapies: | vertoporfin (BPD-MA) |
|  | Phthalocyanine |
|  | photosensitizer Pc4 |
|  | Demethoxy-hypocrellin A |
|  | (2BA-2-DMHA) |
| Cytokines: | Interferon-α |
|  | Interferon-γ |
|  | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Kinase inhibitors: | Imatinib Mesylate |
| Actinomycins: | Actinomycin D |
|  | Dactinomycin |
| Bleomycins: | bleomycin A2 |
|  | Bleomycin B2 |
|  | Peplomycin |
| Anthracyclines: | daunorubicin |
|  | Doxorubicin (adriamycin) |

TABLE 1-continued

CHEMOTHERAPEUTICS AND OTHER ANTI-CANCER AGENTS

| | |
|---|---|
| | Idarubicin |
| | Epirubicin |
| | Pirarubicin |
| | Zorubicin |
| | Mitoxantrone |
| MDR inhibitors: | verapamil |
| $Ca^{2+}$ ATPase inhibitors: | thapsigargin |

In other embodiments, the methods for treating or preventing cancer or a neoplastic disease comprise administering an effective amount of a Diterpenoid Compound and an effective amount of radiation therapy or another chemotherapeutic agent, in one embodiment, with a chemotherapeutic agent with which treatment of the cancer has not been found to be refractory. The Diterpenoid Compound can be administered to a patient that has also undergone surgery as treatment for the cancer.

In another specific embodiment, the invention provides methods for treating or preventing cancer that has shown to be refractory to treatment with a chemotherapy and/or radiation therapy.

In a specific embodiment, a Diterpenoid Compound is administered concurrently with chemotherapy or radiation therapy. In another specific embodiment, chemotherapy or radiation therapy is administered prior or subsequent to administration of a Diterpenoid Compound, preferably at least an hour, five hours, 12 hours, a day, a week, a month, more preferably several months (e.g., up to three months), subsequent to administration of the Diterpenoid Compound.

The chemotherapy or radiation therapy administered concurrently with, or prior or subsequent to, the administration of a Diterpenoid Compound can be accomplished using any method known in the art. The chemotherapeutic agents can be administered in a series of sessions, any one or a combination of the chemotherapeutic agents listed above can be administered. With respect to radiation therapy, any radiation therapy protocol can be used depending upon the type of cancer to be treated or prevented. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered to expose tissues to radiation.

Additionally, the invention provides methods for treating or preventing cancer or neoplastic disease with a Diterpenoid Compound as an alternative to chemotherapy or radiation therapy where the chemotherapy or the radiation therapy has proven or might prove too toxic, e.g., results in unacceptable or unbearable side effects, for the patient being treated. The patient being treated with the Diterpenoid Compound can, optionally, be treated with other cancer treatments such as surgery, radiation therapy or chemotherapy, depending on which treatment is found to be acceptable or bearable.

5.12.3 Cancer and Neoplastic Disease Treatable or Preventable

Cancers or neoplastic diseases and related disorders that can be treated or prevented by administration of an effective amount of a Diterpenoid Compound and cancer cells and neoplastic cells whose growth can be inhibited or in which cytotoxicity, e.g., through apoptosis, can be induced by contacting with an effective amount of a Diterpenoid Compound include but are not limited to those listed in Table 2 (for a review of such disorders, see Fishman et al., 1985, *Medicine*, 2d Ed., J.B. Lippincott Co., Philadelphia):

TABLE 2

CANCERS AND NEOPLASTIC DISORDERS

Leukemia
    acute leukemia
    acute T-cell leukemia
    acute lymphocytic leukemia
    acute myelocytic leukemia
        myeloblastic
        promyelocytic
        myelomonocytic
        monocytic
    erythroleukemia
    chronic leukemia
    chronic myelocytic (granulocytic) leukemia
    chronic lymphocytic leukemia
Polycythemia vera
Lymphoma
    Hodgkin's disease
    non-Hodgkin's disease
Multiple myeloma
Waldenström's macroglobulinemia
Heavy chain disease
Solid tumors
sarcomas and carcinomas
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
    pancreatic cancer
    breast cancer
    ovarian cancer
    prostate cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    cervical cancer
    uterine cancer
    testicular tumor
    lung carcinoma
    small cell lung carcinoma
    bladder carcinoma
    epithelial carcinoma
    glioma
    astrocytoma
    medulloblastoma TABLE 2-continued

CANCERS AND NEOPLASTIC DISORDERS craniopharyngioma
ependymoma
pinealoma
hemangioblastoma
acoustic neuroma
oligodendroglioma
meningioma
melanoma
neuroblastoma
retinoblastoma
NSCL-LC carcinoma
NSCL-adrenocarcinoma
Liver cancer
Breast epithelial cancer
Endothelial cancer
Bronchial epithelial cancer In specific embodiments, cancer, malignancy or dysproliferative changes (such as metaplasias and dysplasias), or hyperproliferative disorders, are treated or prevented in the ovary, breast, colon, lung, skin, pancreas, prostate, bladder, cervix or uterus. In other specific embodiments, sarcoma, melanoma, or leukemia is treated or prevented.

In one embodiment, the Diterpenoid Compounds are useful for treating or preventing cancers including prostate cancer, such as hormone-insensitive prostate cancer, Neuroblastoma, Lymphoma (preferably follicular or Diffuse Large B-cell), Breast (for example Estrogen-receptor positive), Colorectal, Endometrial, Ovarian, Lymphoma (for example non-Hodgkin's), Lung (for example Small cell), or Testicular (for example germ cell).

In another embodiment, the Diterpenoid Compounds are useful for inhibiting the growth of a cell derived from a cancer or neoplasm such as prostate (in one embodiment, hormone-insensitive), Neuroblastoma, Lymphoma (in one embodiment, follicular or Diffuse Large B-cell), Breast (in one embodiment, Estrogen-receptor positive), Colorectal, Endometrial, Ovarian, Lymphoma (in one embodiment, non-Hodgkin's), Lung (in one embodiment, Small cell), or Testicular (in one embodiment, germ cell).

In other embodiments of the invention, the Diterpenoid Compounds are useful for inhibiting the growth of a cell, said cell being derived from a cancer or neoplasm in Table 2 or herein.

5.13 Inhibition of Fungal Growth and Treatment and Prevention of Fungal Infections The invention provides methods for treating or preventing a fungal infection, comprising administering to a patient in need of such treatment or prevention an effective amount of a Diterpenoid Compound. Fungal Infections that can be treated or prevented by administering an effective amount of a Diterpenoid Compound include, but are not limited to, Candida (including C. albicans, C. tropicalis, C. parapsilosis, C. stellatoidea, C. krusei, C. parakrusei, C. lusitanae, C. pseudotropicalis, C. guilliermondi, C. dubliniesis, C. famata or C. glabrata), Aspergillus (including A. fumigatus, A. flavus, A. niger, A. nidulans, A. terreus, A. sydowi, A. flavatus or A. glaucus), Cryptococcus, Histoplasma, Coccidioides, Paracoccidioides, Blastomyces, Basidiobolus, Conidiobolus, Rhizopus, Rhizomucor, Mucor, Asbidia, Mortierella, Cunninghamella, Saksenaea, Pseudallescheria, Paecilomyces, Fusarium, Trichophyton, Trichosporon Microsporum, Epidermophyton, Scytalidium, Malassezia, Actinomycetes, Sporothrix, Penicillium, Sacharomyces, Pneumocystis or Scopulariopsis infections.

In certain embodiments, such fungal infections in animals, including humans, can be a systemic, topical or mucosal infection.

In view of their antifungal activity, Diterpenoid Compounds are useful in the treatment of variety of fungal infections in animals, including humans. Such infections can be superficial, cutaneous, subcutaneous or systemic mycotic infections such as respiratory tract infections, gastrointestinal infections, cardiovascular infections, urinary tract infections, CNS infections, candidiasis and chronic muccocandidiasis and skin infections caused by fungi, cutaneous and mucocutaneous candidiasis, athletes foot, paronychia, fungal nappy rash, candida vulvitis, candida balanitis and otitis extema. They may also be used as prophylactic agents to prevent systemic and topical fungal infections. Use as prophylactic agents may be appropriate as part of a selective gut decontamination regimen in the prevention of infection in immunocomprised patients, e.g., AIDS patients and patients receiving transplant therapy.

The invention further provides a method for inhibiting the growth of a fungus comprising contacting the fungus with an effective amount of a Diterpenoid Compound. The fungi whose growth can be inhibited with a Diterpenoid Compound include Candida (including C. albicans, C. tropicalis, C. parapsilosis, C. stellatoidea, C. krusei, C. parakrusei, C. lusitanae, C. pseudotropicalis, C. guilliermondi, C. dubliniesis, C. famata or C. glabrata), Aspergillus (including A. fumigatus, A. flavus, A. niger, A. nidulans, A. terreus, A. sydowi, A. flavatus or A. glaucus), Cryptococcus, Histoplasma, Coccidioides, Paracoccidioides, Blastomyces, Basidiobolus, Conidiobolus, Rhizopus, Rhizomucor, Mucor, Asbidia, Mortierella, Cunninghamella, Saksenaea, Pseudallescheria, Paecilomyces, Fusarium, Trichophyton, Trichosporon Microsporum, Epidermophyton, Scytalidium, Malassezia, Actinomycetes, Sporothrix, Penicillium, Sacharomyces, Pneumocystis or Scopulariopsis.

In certain embodiments, the Diterpenoid Compounds can be used as anti-fungal agents in vitro or in vivo. In a specific embodiment, the Diterpenoid Compounds can be used to prevent growth of a fungus wherever absence of fungal growth is desired, such as on or in food, medical instruments or devices, clothing, furniture and home appliances.

The following examples exemplify non-limiting aspects of the present invention.

6. EXAMPLES

6.1 Establishment and Manipulation of a Plant Cell Suspension Culture of Linum Arboreum A plant cell culture of Linum arboreum (Linaceae) was prepared using shoots of L. arboreum. The shoots were sterilized by immersion for 1 minute in 70% ethanol followed by immersion for 25 minutes in a solution of sodium hypochlorite (concentration 15%). The sterile shoots were chopped into small pieces of approximately 5 mm and placed upon solidified callus induction medium B5 (Gamborgs B5 recipe (Exp. Cell. Res. 50: 148 (1968)) containing 2,4-dichlorophenoxyacetic acid (2,4-D) (1 mg/L), kinetin (0.1 mg/L), sucrose (2%)). Callus initiations were incubated in continuous low light at 23_C. Upon establishment of callus, the material was used to initiate suspension cultures.

To establish suspension cultures, portions of established callus were placed in 100 mL conical flasks containing liquid medium B88, modified after Gamborgs B5 recipe to contain 2,4-D (1 mg/L), kinetin (0.1 mg/L), coconut water (10%)+3% sucrose. The liquid medium was replenished at 14 day intervals. After 4 months the established suspension culture was routinely maintained in a 250 mL conical flask, by transferring 40 mL of a 14 or 21 day old suspension culture into 100 mL fresh B88 medium. The culture was incubated at 25° C. in continuous low light and shaken at 140 rpm.

Accumulation of isolated compounds was induced in the *Linum arboreum* suspension culture according to either one of the following protocols.

(1) 2 L conical flasks each containing 750 mL of a secondary metabolite production medium B49 (Gamborgs B5, 5% sucrose, no hormones), were each inoculated with 260 mL of a 14-day old suspension culture grown on B88 medium. The cultures were incubated under low light conditions (approximately 30 lux) at 25° C. for 28 days.

(2) A 40 mL aliquot of a day 0 suspension growing on B88 medium was transferred to a 100 mL flask. On day 3, a sterile solution of 5-azacytidine (5-AC) in water was added for a final concentration of $3 \times 10^{-5}$ M, and the resultant mixture was incubated for 11 days. At this point the 40 mL 5-AC-treated culture was subcultured, twice before inoculating 190 mL B49 production medium in a 500 mL flask with 70 mL of a 14 day-old suspension. The culture was incubated under low light conditions (approximately 30 lux) at 25° C. for 7 days following inoculation, filter-sterilized methyl jasmonate (250 uM final concentration) and an autoclaved *Candida albicans* preparation (50 mg/L final concentration) were added. The *C. albicans* preparation was obtained by growing a culture of strain ATCC28516 on YEPD media (yeast extract 1%, yeast peptone 2%, glucose 2%) to maximum cell density and twice autoclaving the total yeast culture prior to addition to plant cultures. The culture was incubated for a further 7 days before harvest of biomass.

6.2 Isolation of Coumpounds 48 and 49

At harvest the plant cell culture of *Linum arboreum*, the culture was centrifuged and the supernatant liquid was decanted. The residual biomass was freeze-dried, and subsequently extracted. Biomass from the culture method (1) in Example 6.1 was used in the following isolation procedure.

81.85 g of dried biomass corresponding to a 6 L culture of *Linum arboreum* obtained above were placed in two 3 L glass beakers, 2 L of methanol was added to each beaker and stirred at room temperature for 20 hours. The mixture was then filtered under vacuum through a fritted funnel. After filtration the marc was washed twice with 250 mL portions of methanol and then the washings were combined with the main filtrate. The combined filtrate and washings were evaporated to dryness under vacuum using a rotary evaporator. The yield of the methanol extract (E11) was 22.8 g (see FIG. 1A).

The E11 extract was dissolved in 2 L of water and then partitioned with 2×1 L of butanol. The butanol phases were separated, combined and then concentrated to dryness. The yield of the butanol exact (E11B) was 7.65 g (33.5% from the methanol extract).

150 mL of HP-20 were placed in a 360 mL fritted glass column (3.8×30 cm) and equilibrated with 10% acetonitrile. Approximately 7.5 g of the E11B extract were re-dissolved in methanol and absorbed into 70 mL of HP-20. The absorbed HP-20 extract was placed on top of the HP-20 column and eluted with an aqueous acetonitrile gradient followed by methanol and acetone. The active fraction (A4) was eluted with methanol. It yielded approximately 420 mg (1.8% from the methanol extract).

Approximately 1 mg of the A4 fraction was fractionated by HPLC using the Gem5.met method (see Experimental Methods below). Fractions were collected in a 96-well plates.

The remainder of the A4 fraction was triturated with 2×50 mL of hexane under mechanical stirring. After centrifugation, the soluble material was concentrated to dryness yielding 197 mg of a hexane fraction (B1). The hexane insoluble material was triturated with 2×50 mL of ethyl acetate. After centrifugation, the soluble material was concentrated to dryness yielding 40 mg of an ethyl acetate fraction (B2). The ethyl acetate insoluble material yielded 135 mg of a methanol soluble fraction (B3). All fractions, B1–B3 were analyzed by HPLC.

B1 and B2 fractions were subjected to preparative reverse phase HPLC using the Gem8p.met method (see Experimental Methods below). Fractions B1C6 and B2C5 (peaks at $R_f$~25.8 mm) were combined to yield 4.3 mg of Compound 48. Fraction B1C4 (peak at $R_f$~14.3 min) yielded 1.5 mg of Compound 49.

Experimental Methods:

| HPLC: Gem5.net | | |
|---|---|---|
| Column: | Xterra™ $RP_{18}$ (150 × 7.8 mm, 7μ) | |
| Flow Rate: | 3 mL/min | |
| Detection: | UV @ 205, 220 and 280 nm | |
| Solvent system: | Time (min.) | $H_2O$ (%) | ACN (%) |
| | 0.0 | 80 | 20 |
| | 5.0 | 60 | 40 |
| | 35.0 | 0 | 100 |
| | 42.0 | 0 | 100 |
| | 45.0 | 80 | 20 |
| | 55.0 | 80 | 20 |
| HPLC: Gem8n.met | | |
| Column: | Xterra™ $RP_{18}$ (300 × 19 mm, 7μ) | |
| Flow Rate: | 14 mL/min | |
| Detection: | UV @ 205, 220 and 277 nm | |
| Solvent system: | Time (min.) | $H_2O$ (%) | ACN (%) |
| | 0.0 | 80 | 20 |
| | 5.0 | 55 | 45 |
| | 50.0 | 0 | 100 |
| | 65.0 | 0 | 100 |
| | 70.0 | 80 | 20 |
| | 85.0 | 80 | 20 |

Structure Elucidation:

Compound 48's $^1$H-NMR and $^{13}$C-NMR assignments were made based on the analysis of their 2D-NMR experiments. The mass spectra showed a peak at m/z 313 corresponding to M+1 ion. The UV spectra showed a maximum absorption at λ 218, 238 (sh), 277 and 326 nm. The $^1$H-NMR spectra run in $CDCl_3$ reveals the presence of four olefinic protons [δ 8.01 (s), δ 7.39 (d, J=10 Hz), δ 6.94 (s), δ 6.29 (d, J=10 Hz)], four methyl groups [δ 2.29 (s), δ 1.69 (s), δ 1.60 (s), δ 1.57 (s)], one methoxy group at δ 3.99 (s) and one exchangeable proton at δ 7.22 (s). The $^{13}$C-NMR spectra run in $CDCl_3$ showed signals for 19 carbons. Multiplicity information was obtained from the DEPT experiments. The olefinic proton at δ 7.39 COSY with the signal at δ 6.29. The magnitude of their coupling constant (J=10 Hz) is in agreement with the cis configuration. 2D-NMR experiments including COSY, HMQC and HMBC were performed in order to assign all proton and carbon signals (Table 3).

Figure 1B:
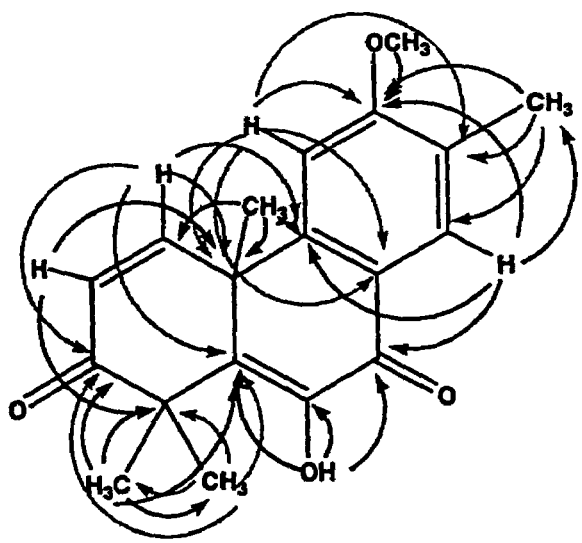
FIG. 1B is a summary of the $^1$H-$^{13}$C correlations observed for Compound 48.

$^1$H-$^{13}$C correlations observed from the HMBC experiment are summarized in FIG. 1B.

Compound 49's mass spectra showed a peak at m/z 329 corresponding to M+1 ion. The UV spectra showed a maximum absorption at λ 216, 238 (sh), 277 and 327 nm. The 1H-NMR spectra run in CDCl$_3$ reveals the presence of four olefinic protons [δ 8.21 (s), δ 7.38 (d, J=10 Hz), δ 7.02 (s), δ 6.30 (d, J=10 Hz)], three methyl groups [δ 1.70 (s), δ 1.60 (s), δ 1.58 (s)], one methoxy group at δ 4.04 (s), one methylene group at δ 4.77 and one exchangeable proton at δ 7.21 (s). The $^{13}$C-NMR spectra run in CDCl$_3$ showed signals for 19 carbons. Structure elucidation was performed by comparison of their $^1$H and $^{13}$C-NMR spectra with Compound 48. The difference appears to be in the aromatic ring where a methylene group is replacing a methyl group. NMR assignments are summarized in Table 4.

TABLE 3

NMR Assignments of Compound 48

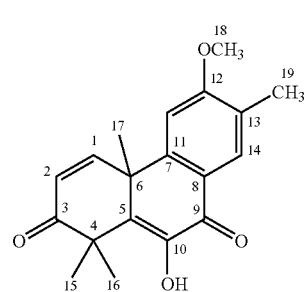

| Atom # | $^{13}$C-NMR (in CDCl$_3$) | $^1$H-NMR (in CDCl$_3$) | $^1$H-NMR (in MeOD) |
|---|---|---|---|
| 1 | 150.6 | 7.39(1H,d,J=10Hz) | 7.65(1H,d,J=10Hz) |
| 2 | 128.4 | 6.29(1H,d,J=10Hz) | 6.27(1H,d,J=10Hz) |
| 3 | 202.7 | — | — |
| 4 | 48.1 | — | — |
| 5 | 133.1 | — | — |
| 6 | 41.7 | — | — |
| 7 | 148.8 | — | — |
| 8 | 120.8 | — | — |
| 9 | 179.0 | — | — |
| 10 | 142.9 | — | — |
| 11 | 105.7 | 6.94(1H,s) | 7.24(1H,s) |
| 12 | 162.6 | — | — |
| 13 | 127.4 | — | — |
| 14 | 129.3 | 8.01(1H,s) | 7.92(3H,s) |
| 15 | 26.3 | 1.60(3H,s) | 1.58(3H,s) |
| 16 | 21.1 | 1.69(3H,s) | 1.67(3H,s) |
| 17 | 38.9 | 1.57(3H,s) | 1.56(3H,s) |
| 18 | 55.7 | 3.99(3H,s) | 4.02(3H,s) |
| 19 | 15.9 | 2.29(3H,s) | 2.26(3H,s) |
| OH | — | 7.22(1H,s) | — |

TABLE 4

NMR Assignments of Compound 49

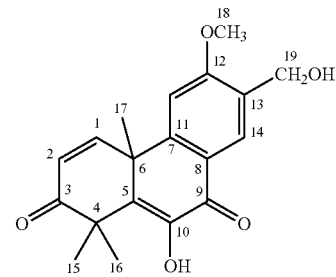

| Atom # | $^{13}$C-NMR (in CDCl$_3$) | $^1$H-NMR (in CDCl$_3$) | $^1$H-NMR (in MeOD) |
|---|---|---|---|
| 1 | 150.1 | 7.38(1H,d,J=10Hz) | 7.67(1H,d,J=10Hz) |
| 2 | 128.6 | 6.30(1H,d,J=10Hz) | 6.30(1H,d,J=10Hz) |
| 3 | 202.5 | — | — |
| 4 | 48.1 | — | — |
| 5 | 133.3 | — | — |
| 6 | 41.9 | — | — |
| 7 | 150.5 | — | — |
| 8 | 121.3 | — | — |
| 9 | 178.8 | — | — |
| 10 | 142.9 | — | — |
| 11 | 106.3 | 7.02(1H,s) | 7.30(1H,s) |
| 12 | 161.8 | — | — |
| 13 | 129.8 | — | — |
| 14 | 127.7 | 8.21(1H,s) | 8.22(1H,s) |
| 15 | 26.3 | 1.60(3H,s) | 1.59(3H,s) |
| 16 | 21.1 | 1.70(3H,s) | 1.68(3H,s) |
| 17 | 38.9 | 1.58(3H,s) | 1.58(3H,s) |
| 18 | 55.9 | 4.04(3H,s) | 4.03(3H,s) |
| 19 | 61.0 | 4.77(2H,s) | 4.67(2H,s) |
| 10-OH | — | 7.21(1H,s) | — |

6.3 Synthesis of Compound 50

Compound 50 was synthesized as illustrated in Scheme 6 and summarized below.

Tetralone 51 was treated with methylmagnesium bromide, and the resulting alcohol was eliminated with hydrochloric acid to provide an alkene. The alkene was treated with m-chloroperbenzoic acid, and the resultant epoxide was treated with boron trifluoride to provide tetralone 52 (Murphy et al. *J. Org. Chem.*, 1960, 25, 1386; Kuehne. *J. Amer. Chem. Soc.*, 1961, 83, 1492; Taylor; Chiang. *Tetrahedron Lett.*, 1977, 1827). A Robinson's annelation was performed on tetralone 52 using a modified method (Shishido, K. et al. *J. Org. Chem.*, 1994, 59, 406–414), and the resulting enone 53 was reduced by a Birch reduction to provide ketone 54. Enone 55 was obtained using known methods (Grieco et al., *J. Org. Chem.*, 1998, 63, 5929–5936) followed by the methylation of the enone to provide Compound 56. Chromium(VI)oxide was used for the benzylic oxidation according to Rutledge (Cambie et al., P. S. *Aust. J. Chem.*, 1998, 51, 931–940) to give ketone 56. The potassium enolate of ketone 56 was oxidized with oxygen, and the resultant 1,2-diketone formed was enolized in-situ to provide Compound 50.

Synthesis of Compound 52

Methylmagnesium bromide (100 mL; 3M solution; 300 mmol) was added to a stirred solution of 7-methoxy-1-teralone 51 (25 g; 142 mmol) in THF (400 mL) at −78° C. The resultant mixture was heated to room temperature and stirred for three hours. The solution was cooled to 0° C. and water (60 mL) was added dropwise, followed by a solution of hydrochloric acid (60 mL conc. HCl and 30 mL water). The resultant solution was stirred at room temperature for one hour and then extracted with ethyl acetate (3×200 mL). The combined organic layers were washed with a saturated aqueous solution of sodium bicarbonate (100 mL), dried over sodium sulfate, decanted and concentrated in vacuo. The resultant residue was dissolved in dichloromethane (400 mL) and cooled to 0° C., and to it was added m-chloroperbenzoic acid (38 g; 77%; 170 mmol). The resultant mixture was stirred at 0° C. for 30 min and then quenched with a saturated aqueous solution of sodium bicarbonate (100 mL) and a solution of saturated aqueous sodium thiosulfate (50 mL). The organic and aqueous layers were separated, and the aqueous layer was extracted with dichloromethane (2×100 mL). The combined organic layers were dried over sodium sulfate, decanted and concentrated in vacuo to a final volume of 400 mL. The solution was cooled to 0° C., and to it was added boron trifluoride diethyletherate (0.9 mL; 7.1 mmol). After 15 min at 0° C. the reaction was quenched with a solution of saturated aqueous sodium bicarbonate (100 mL). The organic and aqueous layers were separated, and the aqueous layer was extracted with dichloromethane (2×100 mL). The combined organic layers were dried over sodium sulfate, decanted and concentrated in vacuo. The resultant residue was purified via column chromatography over silica gel (10% ethyl acetate in hexane eluent) to provide Compound 52 (20 g, 74%) as a colorless oil.

NMR $^1$H (300 MHz, CDCl$_3$): δ (ppm) 1.46 (d, J=8 Hz, 3H), 2.53 (m, 2H), 3.0 (m, 2H), 3.48 (q, J=8 Hz, 1H), 3.82 (s, 3H), 6.77 (m, 2H), 7.13 (d, J=8 Hz, 1H).

Synthesis of Compound 53

To a stirred solution of potassium hydroxide (1.27 g; 22.7 mmol) in methanol (22 mL) and water (2.5 mL) at −15° C., was added, dropwise, Compound 52 (3.6 g; 18.9 mmol) in methanol (5 mL). After 30 min at −15° C., ethyl vinyl ketone (1.87 mL; 18.9 mmol) was added. The resultant solution was stirred 1 h at −15° C., heated at room temperature for 1 h and finally heated to 50° C. for 2 hrs. The methanol was removed in vacuo and the residue was dissolved in water (30 mL) and extracted with ethyl acetate (3×25 mL). The combined organic layers were dried over sodium sulfate, decanted and concentrated in vacuo. The resultant residue was purified via column chromatography over silica gel (10% ethyl acetate in hexane eluent) to provide Compound 53 (3.5 g, 72%) as a pale yellow solid.

NMR $^1$H (300 MHz, CDCl$_3$): δ (ppm) 1.52 (s, 3H), 1.85 (s, 3H), 2.06 (m, 1H), 2.3–3.1 (m, 7H), 3.80 (s, 3H), 6.72 (dd, J=9 Hz and 2 Hz, 1H), 6.84 (d, J=2 Hz, 1H), 7.03 (d, J=9 Hz, 1H).

Synthesis of Compound 54

To a stirred solution of lithium (948 mg; 136 mmol) in liquid ammonia (75 mL) at −78° C., was added dropwise a solution of Compound 53 (3.5 g; 13.6 mmol) and t-butanol (1.3 mL; 13.6 mmol) in tetrahydrofuran (25 mL). After 1.5 hr at −78° C., isoprene (7 mL; 68 mmol) was added dropwise, and the reaction mixture was heated to room temperature to allow the ammonia to evaporate. A saturated aqueous solution of ammonium chloride (50 mL) was added to the residue, and the resultant mixture was extracted with ethyl acetate (3×50 mL). The combined organic layers were dried over sodium sulfate, decanted and concentrated in vacuo. The resultant residue was purified via column chromatography over silica gel (10% ethyl acetate in hexane eluent) to provide Compound 54 (1.64 g, 66%) as a white solid.

NMR $^1$H (300 MHz, CDCl$_3$): δ (ppm) 1.12 (d, J=7 Hz, 3H), 1.38 (s, 3H), 1.63 (m, 2H), 1.86 (m, 1H), 1.97 (m, 1H), 2.40–2.69 (m, 4H), 2.86 (m, 2H), 3.79 (s, 3H), 6.71 (dd, J=9 Hz and 2 Hz, 1H), 6.85 (d, J=2 Hz, 1H), 7.00 (d, J=9 Hz, 1H).

Synthesis of Compound 55

Compound 54 was converted to Compound 55 using known methods (Grieco, et al. *J. Org. Chem.*, 1998, 63, 5929–5936).

NMR $^1$H (300 MHz, CDCl$_3$): δ (ppm) 1.23 (d, J=7 Hz, 3H), 1.34 (s, 3H), 1.67 (m, 1H), 2.00 (m, 2H), 2.43 (m, 1H), 2.88 (m, 2H), 3.80 (s, 3H), 5.97 (d, J=10 Hz, 1H), 6.71 (dd, J=9 Hz and 2 Hz, 1H), 6.95 (d, J=2 Hz, 1H), 7.00 (d, J=9 Hz, 1H), 7.54 (d, J=10 Hz, 1H).

Synthesis of Compound 56

To a stirred suspension of potassium hydride (492 mg; 30% dispersion in mineral oil; 3.69 mmol) in tetrahydrofuran (8 mL) at 0° C., was added dropwise a solution of Compound 55 (315 mg; 1.23 mmol) in tetrahydrofuran (9 mL). After 30 min at 0° C., freshly distilled iodomethane (0.765 mL; 12.3 mmol) was added. The reaction mixture was stirred at 0° C. for 1 hr and then quenched with a solution of saturated aqueous ammonium chloride (10 mL). The organic and aqueous layers were separated, and the aqueous layer was extracted with ethyl acetate (3×20 mL). The combined organic layers were dried over sodium sulfate, decanted and concentrated in vacuo. The resultant residue was purified via column chromatography over silica gel (15% ethyl acetate in hexane eluent) to provide Compound 56 (240 mg, 54%).

NMR $^1$H (300 MHz, CDCl$_3$): δ (ppm) 1.18 (s, 3H), 1.20 (s, 3H), 1.40 (s, 3H), 1.89 (m, 2H), 2.14 (dd, J=11 Hz and 4 Hz, 1H), 2.88 (m, 2H), 3.79 (s, 3H), 6.00 (d, J=10 Hz, 1H), 6.71 (dd, J=9 Hz and 2 Hz, 1H), 6.91 (d, J=2 Hz, 1H), 7.02 (d, J=9 Hz, 1H), 7.53 (d, J=10 Hz, 1H).

Synthesis of Compound 50

To a stirred solution of Compound 56 (240 mg; 0.89 mmol) in acetic acid (6 mL) at 0° C., was added, before freezing of the acetic acid, a solution of chromium(VI) oxide (222 mg; 2.23 mmol) in acetic acid/water (1.2 mL/0.3 mL) dropwise over 10 min. The reaction mixture was stirred at 0° C. for 15 min, and then water (10 mL) was added. The reaction mixture was extracted with ethyl acetate (3×10 mL), and the combined organic layers were washed with a solution of saturated aqueous sodium bicarbonate (10 mL), dried over sodium sulfate, filtered through a short pad of silica gel, washed with ethyl acetate (50 mL) and concentrated in vacuo. The resultant residue was dissolved in tetrahydrofuran (3 mL) and added dropwise to a stirred solution of potassium t-butoxide (300 mg; 2.67 mmol) in t-butanol (5.5 mL) and tetrahydrofuran (13 mL) at 0° C. The resultant solution was stirred at 0° C. under oxygen atmosphere (balloon) for 1 h and then quenched with a solution of saturated aqueous ammonium chloride (10 mL). The resultant reaction mixture was extracted with ethyl acetate (3×20 mL), and the combined organic layers were dried over sodium sulfate, filtered through a short pad of silica gel, washed with ethyl acetate (50 mL) and concentrated in vacuo. The resultant residue was triturated in cold ethanol (4 mL) and filtered to provide Compound 50 (130 mg, 49%) as a white solid.

NMR $^1$H (300 MHz, CDCl$_3$): δ (ppm) 1.57 (s, 3H), 1.59 (s, 3H), 1.69 (s, 3H), 3.95 (s, 3H), 6.27 (d, J=10 Hz, 1H), 7.00 (dd, J=9 Hz and 2 Hz, 1H), 7.08 (d, J=2 Hz, 1H), 7.20 (s, 1H), 7.37 (d, J=10 Hz, 1H), 8.20 (d, J=9 Hz, 1H). NMR $^{13}$C (75 MHz, CDCl$_3$): δ (ppm) 202.6, 179.0, 164.2, 150.8, 150.6, 143.0, 133.6, 130.1, 128.6, 121.6, 113.8, 111.0, 56.0, 48.4, 42.1, 39.3, 26.7, 21.5. MP: 167° C.–168° C.

Synthesis of Compound 50a and Compound 50b

Compound 50a and Compound 50b were synthesized as illustrated in Scheme 7.

Synthesis of Compound 61

Compound 61 was synthesized as described in Takahashi et al., *Syn. Lett.* 1999, 5, 6444–646; Corey, et al. *J. Am. Chem Soc.* 1997, 119, 9927–9928; and Rosales et al. *J. Org. Chem.* 2002, 67, 1167–1170.

To a solution of geraniol 57 (100 mol %; 5.0 mmole; 868 μL) in dry THF at −45° C. was added methanesulfonyl chloride (130 mol %; 6.5 mmole; 502 μL) and triethylamine (200 mol %; 10 mmole; 1.4 mL). The resultant solution was stirred at −45° C. for 45 min, then warmed to 0° C., at which point lithium chloride (400 mol %, 20 mmole, 848 mg as a solid) or lithium bromide (400 mol %, 20 mmole, 1.737 g as a solution in 8 mL of THF via cannula) was added. The resultant solution was stirred for 1 hr at 0° C. Water was added (50 mL), and the resultant mixture was extracted using hexane (2×30 mL). The combined organic solution was successively washed with saturated $NaHCO_3$ and brine, dried over $Na_2SO_4$, filtered and evaporated to provide crude allylic halides 58 and 59, which were used directly, without further purification, in the next step.

To a solution of tetrakis(triphenylphosphine)palladium(0) (5 mol %; 50 μmol; 58 mg) in dry and freshly degassed THF was added allylic halide 58 or 59 (100 mol %; 1.0 mmole; 58: 217 mg; 59: 173 mg). The resulting solution was stirred at room temperature (20° C.) for 5 min then cooled to 0° C. p-Methoxybenzyl magnesium chloride 60 (130 mol %; 1.3 mmole; 5.2 mL of a 0.25 M solution in THF) was added via syringe and the reaction mixture was stirred at room temperature (20° C., 58: 5 hrs; 59: 3 hrs). Water was added (20 mL), and the mixture was extracted using $Et_2O$ (2×10 mL). The combined organic solution was dried over $Na_2SO_4$, filtered and evaporated. The crude reaction product was dissolved in pentane and filtered through a pad of silica gel, the pad was further rinsed with $CHCl_3$. The $CHCl_3$ filtrate was evaporated and the resultant residue was purified via column chromatography over silica gel using a gradient of 0–2% of EtOAc/Hexanes to obtain Compound 61 (162 mg; 63%). This reaction was also performed on larger scale with 3.0 mmole of allylic halide 58 to give 61 (517 mg; 65%).

$MH^+/Z$ calc. for $C_{18}H_{27}O_1$=259.21. LRMS found=259.27. $^1$H NMR (300 MHz, $CDCl_3$): δ (ppm) 1.59 (s, 3H); 1.64 (s, 3H); 1.72 (s, 3H); 1.99–2.13 (m, 4H); 2.26–2.34 (m, 2H); 2.58–2.85 (m, 2H); 3.80 (s, 3H); 5.09–5.14 (m, 1H); 5.17–5.22 (m, 1H); 6.81–6.86 (m, 2H); 7.08–7.26 (m, 2H).

Synthesis of the Racemic Epoxide 63

The racemic epoxide 0.63 was synthesized as described in Ceruti, M. et al. *J. Med. Chem.* 1998, 41, 540–554.

To a solution of Compound 61 (100 mol %; 2.0 mmole; 517 mg) in THF (58 mL) at 0° C. was added water (50 mL) until the solution reached opalescence. The resultant mixture was stirred at 0° C., and N-bromosuccinimide (NBS; 110 mol %; 2.2 mmole; 392 mg) was added in portions over 10 min. Water was added during the addition to maintain opalescence of the solution. After the addition of NBS was completed the reaction mixture was stirred an additional 15 min at 0° C. and water was continuously added to maintain opalescence (total volume of water added: 20 mL). Saturated aqueous $NaHCO_3$ was added (60 mL) and the resulting mixture was extracted using $Et_2O$ (3×60 mL). The organic layers were combined and washed using saturated aqueous $NaHCO_3$ (60 mL) and brine (60 mL). The organic solution was dried over $Na_2SO_4$, filtered and evaporated. The resultant residue was purified via column chromatography over silica gel using a gradient of 0–6% EtOAc/Hexanes to provide a crude bromohydrin (487 mg; 69%).

$^1$H NMR (300 MHz, $CDCl_3$): δ (ppm) 1.34 (s, 3H); 1.34 (s, 3H); 1.54 (s, 3H); 1.76–1.84 (m, 1H); 1.93–1.99 (m, 1H); 2.12–2.16 (m, 2H); 2.27–2.34 (m, 2H); 2.59–2.65 (m, 2H); 3.80 (s, 3H); 3.92 (dd, $J_1$=2.0 Hz, $J_2$=11 Hz, 1H); 5.24–5.29 (m, 1H); 6.80–6.85 (m, 2H); 7.08–7.26 (m, 2H).

To a suspension of $K_2CO_3$ (300 mol %; 3.6 mmole; 498 mg) in methanol (20 mL) was added freshly prepared crude bromohydrin, above (100 mol %; 1.2 mmole; 426 mg). The reaction mixture was stirred at room temperature (20° C.) for 2.5 hrs (reaction was monitored by TLC analysis). Water was added and the resultant mixture was extracted with $Et_2O$ (3×50 mL). The organic layers were combined and washed using brine (2×50 mL). The organic solution was dried over $Na_2SO_4$, filtered and evaporated. The resultant residue was purified via column chromatography over silica gel using a gradient of 0–5% EtOAc/Hexanes to provide compound 63 (261 mg; 79%).

$^1$H NMR (300 MHz, $CDCl_3$): δ (ppm) 1.28 (s, 3H); 1.32 (s, 3H); 1.59 (s, 3H); 1.61–1.72 (m, 2 H); 2.07–2.18 (m, 2H); 2.30 (dd, $J_1$=7.2 Hz, $J_2$=15 Hz, 2H); 2.60 (t, J=7.6 Hz, 2H); 2.70 (t, J=6.4 Hz, 1H); 3.79 (s, 3H); 5.21–5.26 (m, 1H); 6.80–6.84 (m, 2H); 7.08–7.13 (m, 2H).

Synthesis of Chiral Diol 62b

The chiral diol 62b was synthesized as discribed in Corey, et al. *J. Am Chem Soc.* 1997. 119, 9927–9928; and Crispino, G. A. et al. *Synthesis* 1993, 777–779

To a mixture of 61 (100 mol %; 1.9 mmole; 500 mg) and chiral catalyst (1,4-bis(dihydroquinidinephthalazine) (($DHQD)_2PHAL$) for the synthesis of the R enantiomer or 1,4-bis(dihydroquininephthalazine) (($DHQD)_2PHAL$) for the synthesis of the S enantiomer (5 mol %; 96 μmol; 75.4 mg), in a 1:1 solution of water:tert-butanol (20 mL) at 0° C. was added potassium carbonate (300 mol %; 5.8 mmole; 800 mg), potassium ferricyanide (300 mol %; 5.8 mmole; 1.90 g), methanesulfonamide (100 mol %; 1.9 mmole; 184 mg), and potassium osmate dihydrate (1 mol %, 19 μmole; 7.1 mg). An additional 15 mL of the 1:1 solution of water:tert-butanol was added, and the reaction mixture was stirred at 0° C. for 4.5 hrs. Saturated aqueous $Na_2S_2O_3$ (10 mL) was added and the reaction was stirred at room temperature (20° C.) for an additional 45 min. Evaporation of the volatiles on rotary evaporator (no heat) was followed by extraction using EtOAc (4×30 mL). The organic layers were combined and washed with KOH (1M; 30 mL) and brine (30 mL). The organic solution was dried over $Na_2SO_4$, filtered and evaporated. Crude diol 62 was purified (first by precipitation of tetrol (overoxydation product) in $Et_2O$ followed by column chromatography over silica gel using a gradient of 0–40% EtOAc/Hexanes to provide Compound 62a (184 mg; 33%) and Compound 62b (127 mg; 22%).

$^1$H NMR (300 MHz, $CDCl_3$): δ (ppm) 1.16 (s, 3H); 1.19 (s, 3H); 1.38–1.46 (m, 1H); 1.57 (s, 3H); 2.05–2.09 (m, 1H); 2.21–2.24 (m, 2H); 2.30 (dd, J=7.6 Hz, $J_2$=15 Hz, 2H); 2.56–2.63 (m, 2H); 3.29 (dd, $J_1$=2.0 Hz, $J_2$=11 Hz, 1H); 3.79 (s, 3H); 5.21–5.26 (m, 1H); 6.79–6.84 (m, 2H); 7.07–7.11 (m, 2H).

Synthesis of Chiral Epoxide 63b

The chiral epoxides 63a and 63b were synthesized as described in Corey, et al. *J. Am. Chem Soc.* 1997, 119, 9927–9928.

The following example is for a synthesis of 63a, but the same procedure was used for synthesis of 63b except that chiral diol 62b was used in place of chiral diol 62a. To a solution of chiral diol 62a (100 mol %; 0.60 mmole; 175 mg) in CH$_2$Cl$_2$ (4 mL) at 0° C. was added pyridine (800 mol %; 4.8 mmole; 388 µL) and methanesulfonyl chloride (480 mol %; 2.8 mmole; 223 µL). The reaction mixture was stirred at 0° C. for 5 min then for an additional 3 hrs at room temperature (20° C.). The solvent was evaporated by nitrogen gas circulation through the reaction flask. Methanol (12 mL) was added along with potassium carbonate (1667 mol %; 10 mmole; 1.44 g), and the resultant suspension was stirred at room temperature (20° C.) for 1–2 hrs (monitored by TLC analysis). Water (20 mL) was added, and the mixture was extracted using Et$_2$O (2×20 mL). The organic layers were combined and washed using dilute Cu(II) nitrate (2×20 mL), water (20 mL), and brine (20 mL). The organic solution was dried over MgSO$_4$, filtered and evaporated. Crude epoxide 63 was purified by column chromatography over silica gel using a gradient of 0–2% EtOAc/Hexanes to provide Compound 63a (105 mg; 64% over two steps) and Compound 63b (70 mg 64% over two steps starting from 0.40 mmole of 62b).

$^1$H NMR (300 MHz, CDCl$_3$): δ (ppm) 1.27 (s, 3H); 1.31 (s, 3H); 1.58 (s, 3H); 1.60–1.72 (m, 2H); 2.09–2.28 (m, 2H); 2.30–2.33 (m, 2H); 2.57–2.62 (m, 2H); 2.70 (t, J=6.4 Hz, 1H); 3.79 (s, 3H); 5.20–5.25 (m, 1H); 6.79–6.84 (m, 2H); 7.07–7.12 (m, 2H).

Synthesis of Compound 64b

Compounds 64a and 64b were synthesized as described in Corey, et al. *J. Am. Chem Soc.* 1997, 119, 9927–9928.

The following example is for synthesis of Compound 64a, but the same procedure was used for synthesis of Compound 64b except that chiral epoxide 63b was used in place of chiral epoxide 63a. To a solution of chiral epoxide 63a (100 mol %; 0.38 mmole; 105 mg) in dichloromethane (3 mL) at −78° C. was added a solution of methylaluminum dichloride (120 mol %; 0.46 mmole; 460 µL of a 1M solution in hexanes) in dichloromethane (3 mL) cooled at −78° C. via cannula. The reaction mixture was stirred at −78° C. for 4 hrs. Triethylamine (0.80 mL) and 1:1 water:methanol (0.80 mL) were added, the resultant mixture was poured onto half saturated aqueous ammonium chloride (20 mL) and extracted using dichloromethane (10 mL) and Et$_2$O (2×20 mL). The organic layers were combined and washed using brine (30 mL). The organic solution was dried over Na$_2$SO$_4$, filtered and evaporated. The resultant residue was purified via column chromatography over silica gel using a gradient of 0–4% EtOAc/Hexanes to provide Compound 64a (52 mg; 50%) and 64b (38 mg, 56% starting from 0.25 mmole of 63b).

$^1$H NMR (300 MHz, CDCl$_3$): δ (ppm) 0.91 (s, 3H); 1.09 (s, 3H); 1.22 (s, 3H); 1.25–1.30 (m, 1H); 1.44–1.62 (m, 1H); 1.67–1.94 (m, 4H); 2.25–2.32 (m, 1H); 2.74–2.96 (m, 2H); 3.29–3.34 (m, 1H); 3.78 (s, 3H); 6.68–6.69 (m, 1H); 6.78–6.79 (m, 1H); 6.95–6.98 (m, 1H).

Synthesis of Compound 65b

Compounds 65a and 65b were synthesized as described in Ley, S. V. et al.; Marsden S. P. *Synthesis* 1994, 639–666.

The following example is for a synthesis of Compound 65a, but the same procedure was used for synthesis of Compound 65b except that Compound 64b was used in place of Compound 64a. To 4 Å dry powdered molecular sieves (121 mg) was added a solution of Compound 64a (100 mol %; 0.19 mmole; 52 mg) in dichloromethane (3 mL), 4-methylmorpholine N-oxide (200 mol %; 0.38 mmole; 45 mg), and tetrapropylammonium perruthenate (10 mol %; 19 µmole; 7.0 mg). The reaction mixture was stirred at room temperature (20° C.) for 1–2 hrs (monitored by TLC analysis). The reaction mixture was filtered through a pad of silica gel, which was rinsed using 5% EtOAc/Hexanes (40 mL). The filtrate was discarded, and the silica gel was washed with 100% EtOAc (40 mL). The filtrate was evaporated to provide Compound 65a (52 mg; 99%) and Compound 65b (36 mg; 96% starting from 0.14 mmole of 64b).

$^1$H NMR (300 MHz, CDCl$_3$): δ (ppm) 1.15 (s, 3H); 1.18 (s, 3H); 1.31 (s, 3H); 1.77–1.84 (m, 2H); 1.89–2.10 (m, 2H); 2.41–2.50 (m, 1H); 2.60–2.91 (m, 4H); 3.78 (s, 3H); 6.68–6.71 (m, 1H); 6.78–6.79 (m, 1H); 6.98–7.00 (m, 1H).

Enantiomeric excess of Compound 65a and Compound 65b was for Compound 65a (R enantiomer)=21.57 min 97% ee. Retention time (Rt) for Compound 65b (S enantiomer)= 21.57 min 92% ee.

Synthesis Compound 56b

Compounds 56a and 56b were synthesized as described in Poigny, S. et al., *J. Org. Chem.* 1998, 63, 5890–5894; and Ito, Y. et al. *J. Org. Chem.* 1978, 43, 1011–1013.

The following example is for a synthesis of Compound 56a, but the same procedure was used for synthesis of Compound 56b except that Compound 65b was used in place of Compound 65a. To a solution of Compound 65a (100 mol %; 0.23 mmole; 64 mg) in dichloromethane (4 mL) at 0° C. was added trimethylsilyl trifluoromethanesulfonate (200 mol %; 0.46 mmole; 84 µL), and the resulting mixture was stirred at 0° C. for 5 min. Triethylamine (250 mol %; 0.58 mmole; 81 µL) was added, and the reaction mixture was stirred at 0° C. for 1 hr (monitored by TLC analysis). Saturated aqueous NaHCO$_3$ was added (10 mL,) and the resultant mixture was extracted using Et$_2$O (3×10 mL). The organic layers were combined and washed using brine (10 mL). The organic solution was dried over MgSO$_4$, filtered and evaporated. Conversion of ketone 65a to its corresponding silyl enol ether appeared to be quantitative, and the silyl enol ether was used without further purification in the next step.

$^1$H NMR (300 MHz, CDCl$_3$): δ (ppm) 0.00 (s, 9H); 0.75 (s, 3H); 0.87 (s, 3H); 1.03 (s, 3H); 1.41–1.45 (m, 2H); 1.56–1.61 (m, 1H); 1.92–1.98 (m, 1H); 2.21–2.29 (m, 1H); 2.51–2.67 (m, 2H); 3.54 (s, 3H); 4.51–4.54 (m, 1H); 6.42–6.45 (m, 1H); 6.56–6.57 (m, 1H); 6.71–6.74 (m, 1H).

To a solution of the silyl enol ether above (100 mol % 0.23 mmole; 80 mg) in acetonitrile (4 mL) was added palladium (II) acetate (200 mol %; 0.47 mmole; 105 mg). The resultant reaction mixture was stirred at reflux for 1 hr. Palladium (II) acetate (100 mol %; 0.23 mmole; 105 mg) was added, and the reaction mixture was stirred at reflux for 30 min. The reaction mixture was cooled to room temperature (20° C.) and stirred for 11.5 hrs, then stirred at reflux for 1 hr. The reaction mixture was then cooled to room temperature (20° C.), filtered and evaporated. Crude enone 56a was purified via column chromatography over silica gel using a gradient of 0–4% EtOAc/Hexanes to provide Compound 56a (40 mg; 63%) and Compound 56b (40 mg; 65% starting from 0.23 mmole of 65b).

Synthesis of Compound 50a and Compound 50b

Compound 50a and Compound 50b were made from Compound 56a and 56b, respectively, according to the procedure, above, used to make Compound 50 from Compound 56. Enantiomeric excess of Compound 50a and Compound 50b was measured using HPLC analysis with a chiral column (Chiralcel OD-RH, 4.6×150 mm): mobile phase A=100 mM KPF$_6$ in water (pH2), mobile phase B=100% acetonitrile, isocratic 40% acetonitrile 60% water at 0.5 mL/min over 60 min, column temperature 30° C., on a Waters Alliance HPLC System 2795 using a PDA detector (200 to 600 nm). Retention time (Rt) for Compound 50a (R enantiomer)=67.25 min 95% ee. Retention time (Rt) for Compound 50b (S enantiomer)=70.92 min 93% ee.

Synthesis of Compound 66, 67, 68 and 69

Compounds 66, 67, 68 and 69 were synthesized according to the method used to synthesize Compound 50, except:

for Compound 66, ethyl iodide was used instead of iodomethane;

for Compound 67, propenyl iodide was used instead of iodomethane;

for Compound 68, benzyl iodide was used instead of iodomethane; and for Compound 69, $CH_3CH_2C(O)C(=CH_2)C(O)OCH_3$ was used instead of ethyl vinyl ketone.

Synthesis of Compound 70

Compound 70 was synthesized according to the method used to synthesize Compound 50, except that twice as much chromium(VI) oxide was used and that the corresponding oxidation was performed at 80° C.

Compound 50, Compound 50a and Compound 50b have also been synthesized by the following procedure.

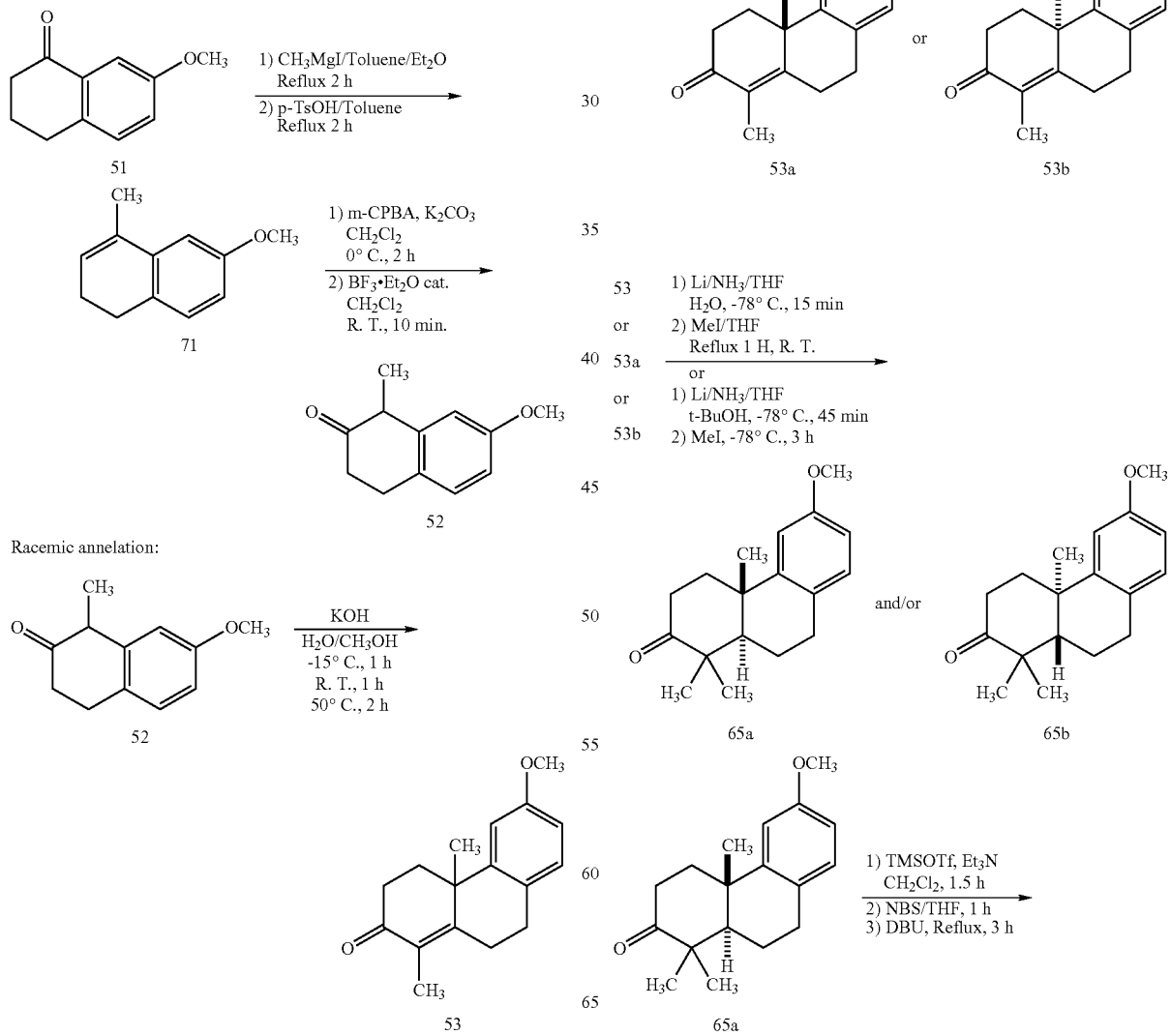

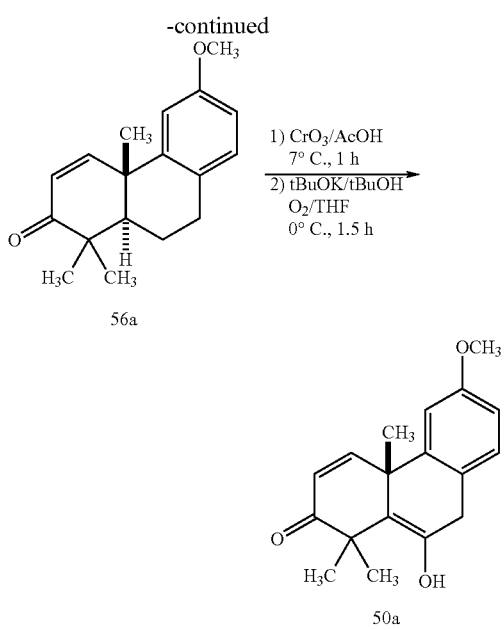

Synthesis of Compound 52

For a description of synthetic methods employed in this example, see also: Selwood, D. L.; Challand, S. R.; Champness, J. N.; Gillam, J.; Hibberd, D. K.; Jandu, K. S.; Lowe, D.; Pether, M.; Selway, J.; Trantor, G. E. *J. Med. Chem.* 1993, 36, 3503–3510. Referring to Scheme 8, to a stirred solution of methylmagnesium iodide (3 M solution in diethyl ether; 130 mol %; 300 mmole; 100 mL) in diethyl ether (100 mL, dry) and toluene (40 mL, dry) is added 7-methoxy-1-tetralone (51, solid; 100 mol %; 231 mmole; 40.67 g) at such a rate as to maintain a steady (but gentle) reflux. After addition of the solid is complete, the reaction mixture is stirred at reflux for 1.5 h. When the reaction is complete (monitored by TLC analysis), a solution of saturated aqueous ammonium chloride (100 mL) is added very slowly over a time-period of ca. five minutes. The mixture is transferred into a separatory funnel and extracted using diethyl ether (50 mL). The organic layer is separated and washed successively using, water (100 mL) and brine (100 mL). The organic layer is dried over sodium sulfate and filtered. The diethyl ether is then concentrated in vacuo taking care to leave the toluene in the flask. Toluene is added if needed to adjust volume at 80 mL. p-Toluenesulfonic acid monohydrate (0.5 mol %; 1.1 mmole; 203 mg) is added and the reaction mixture is stirred at reflux using a Dean Stark trap for 1 h. The reaction mixture is cooled to room temperature and washed using saturated aqueous sodium bicarbonate (100 mL) and brine (100 mL). The organic layer is dried over sodium sulfate. At this point the volume of the organic phase is approximately 75 mL (of toluene). Hexanes are added (80 mL), the mixture is filtered through a pad of silica gel and rinsed using hexanes (2×80 mL). The combined filtrate is concentrated in vacuo to give 31.2 g; 179 mmole; 77% of 71. This product is taken directly to the next step.

3-Chloroperoxybenzoic acid (m-CPBA, 77%; 150 mol %; 270 mmole; 60.52 g) and potassium carbonate (200 mol %; 360 mmol; 50 g) are added to a solution of 71 (100 mol %; 179 mmole; 31.2 g) in dichloromethane (510 mL) at 0° C. The reaction mixture is stirred at 0° C. for 3 h (after this time an additional 25 mol % of m-CPBA can be added if needed and the mixture stirred for an additional 1 h). When the reaction appears complete (TLC analysis), the mixture is pored onto 200 mL of ice cold water, saturated aqueous sodium bicarbonate (100 mL) is added along with saturated aqueous sodium thiosulfate (100 mL), the organic layer is separated and conserved (i). The aqueous layer is further extracted with dichloromethane (2×200 mL; ii). The combined organic layers (i+ii) are washed with brine, dried over sodium sulfate, filtered, and reduced down to a volume of 400 mL (of dichloromethane). Boron trifluoride diethyl etherate (1.00 mol %; 2.00 mmole; 0.25 mL) is added and the reaction mixture is stirred at room temperature for 10 min. Saturated aqueous sodium bicarbonate (100 mL) is added, the organic layer is separated and conserved (iii). The aqueous layer is further extracted with dichloromethane (2×100 mL; iv). The combined organic layers (iii+iv) are washed with brine, dried over sodium sulfate, filtered, and concentrated in vacuo. The resulting oil is loaded on a pad of silica gel and eluted using 10% ethyl acetate in hexanes (500 mL) to give 52 (30.1 g, 88%, 68% over two steps). The product obtained (52, either an oil or a solid) can be crystallized in diethyl ether (≈1 mL/g) at −78° C. until some crystals form (1 to 2 h) and then in the freezer (−20° C.) overnight to give 52 as white crystals (26.3 g, 60% from starting 7-methoxy-1-tetralone).

$^1$H NMR (300 MHz, CDCl$_3$): δ (ppm) 1.48 (d, J=7 Hz, 3H); 2.43–2.67 (m, 2H); 3.01–3.06 (m, 2H); 3.47–3.54 (m, 1H); 3.81 (s, 3H); 6.74–6.77 (m, 2H); 7.13 (d, J=9 Hz, 1H).

Synthesis of Compound 53

Racemic Robinson Annelation:

To a stirred solution of potassium hydroxide (120 mol %; 22.7 mmole; 1.27 g) in methanol (22 mL) and water (2.5 mL) at −15° C., is added, dropwise, 3 (100 mol %; 18.9 mmole; 3.6 g) in methanol (5 mL). After 30 min at −15° C., ethyl vinyl ketone (freshly distilled, 100 mol %; 18.9 mmole; 1.87 mL) is added and the resulting solution is stirred 1 hr at −15° C., then warmed to room temperature and stirred for 1 h, followed by heating at 50° C. for 2 hrs. The methanol is removed by rotary evaporation and the residue is dissolved in water (30 mL) and extracted with ethyl acetate (3×25 mL). The combined organic layers are dried over sodium sulfate, filtered and concentrated by rotary evaporation. The residue is purified by column chromatography over silica gel and eluted using 10% ethyl acetate in hexanes to give 53 (3.5 g, 72%) as a pale yellow solid. This procedure was repeated on larger scale, using 13 g of 52, to give 16 g; 94% of 53.

$^1$H NMR (300 MHz, CDCl$_3$): δ (ppm) 1.54 (s, 3H); 1.85 (s, 3H); 2.06–2.13 (m, 1H); 2.33–2.99 (m, 7H); 3.81 (s, 3H); 6.72 (dd, J=9 Hz and 3 Hz, 1H); 6.84 (d, J=3 Hz, 1H); 7.04 (d, J=8 Hz, 1H).

Synthesis of Compound 53a and Compound 53b

The following experimental procedure is an example for the synthesis of 53a (for a description of synthetic methods employed in this example, see also: Selwood, D. L.; Challand, S. R.; Champness, J. N.; Gillam, J.; Hibberd, D. K.; Jandu, K. S.; Lowe, D.; Pether, M.; Selway, J.; Trantor, G. E. *J. Med. Chem.* 1993, 36, 3503–3510). The same procedure can be followed using (S)-(−)-α-methylbenzylamine as chiral inducer for synthesis of 53b.

Chiral Robinson Annelation:

(R)-(+)-α-Methylbenzylamine (110 mol %; 23.1 mmole; 2.94 g) and p-toluenesulfonic acid monohydrate (1.6 mol %; 336 μmole; 64 mg) are added to a solution of 7-methoxy-1-methyl-3,4-dihydro-1H-naphthalen-2-one (52) in toluene (30 mL). The reaction mixture is stirred at reflux using a Dean Stark trap for 5 hrs. The reaction mixture is then cooled to room temperature, the toluene is removed by rotary evaporation, and the oily residue is dissolved in tetrahydrofuran (26 mL). Ethyl vinyl ketone (freshly distilled, 140 mol %; 29.4 mmole; 2.93 mL) is added and the reaction mixture is stirred at room temperature for 16 hrs. A solution of acetic acid (20% aqueous, 32 mL) is then added and the resulting mixture is stirred for an additional 1 h. After removal of the volatiles by rotary evaporation, the residue is dissolved in ethyl acetate (50 mL) and washed successively using: saturated aqueous sodium bicarbonate (2×50 mL) and brine (50 mL). The organic layer is dried over magnesium sulfate, filtered and concentrated in vacuo. The residue is dissolved in methanol (30 mL), sodium methoxide (97 mol %; 20.4 mmole; 1.39 g) is added and the mixture is stirred at reflux for 3.5 hrs. The methanol is removed by rotary evaporation (careful: foaming), the residue is dissolved in ethyl acetate (50 mL) and washed successively using: water (30 mL) and brine (30 mL). The organic layer is dried over magnesium sulfate, filtered and concentrated in vacuo. The resulting oil is purified by column chromatography over silica gel and eluted using a gradient of 0–10% ethyl acetate in hexanes, to give 53a (4.04 g; 15.8 mmole, 75%, determined to be 74% ee by chiral HPLC). Crystallization in diethyl ether:hexanes 1:1 followed by recrystallization in diethyl ether gave material of >99% ee (determined by chiral HPLC).

Enantiomeric excess was determined using HPLC analysis with a chiral column (Chiralcel™ OD-RH, 4.6×150 mm): mobile phase isocratic 40% acetonitrile 60% water at 0.5 mL/min over 70 min, column temperature 25° C., on a Waters Alliance HPLC System 2795 using a PDA detector (200 to 600 nm).

$^1$H NMR (300 MHz, CDCl$_3$): δ (ppm) 1.54 (s, 3H); 1.85 (s, 3H); 2.06–2.13 (m, 1H); 2.33–2.99 (m, 7H); 3.81 (s, 3H); 6.72 (dd, J=9 Hz and 3 Hz, 1H); 6.84 (d, J=3 Hz, 1H); 7.04 (d, J=8 Hz, 1H).

Synthesis of Compound 65

Birch Reduction/Alkylation, Method 1

Robinson annelation product 53 (100 mol %; 3.90 mmole; 1.0 g) is dissolved in tetrahydrofuran (25 mL) at −78° C. (under nitrogen). Water (100 mol %; 3.90 mmole; 70 μL) is added along with ammonia (20 mL). Lithium metal (wire, 225 mol %; 8.80 mmole; 61 mg) is introduced carefully and the clear solution slowly turns blue. Stirring is continued until reduction appears complete by TLC analysis. When reduction is complete the reaction is warmed to −20° C. and the ammonia is allowed to evaporate. When most of the ammonia is gone, the reaction mixture is warmed to room temperature and stirred for 30 min, then cooled to 0° C. and iodomethane (500 mol %; 19.5 mmole; 1.21 mL) is added. The reaction is stirred for 30 min at room temperature and for 3 hrs at reflux. The reaction mixture is allowed to cool and is then quenched with an ammonium chloride solution (saturated aqueous, 30 mL), water is added and the mixture is extracted using dichloromethane (2×40 mL). The organic layers are combined and washed using a sodium thiosulfate solution (saturated aqueous, 30 mL) and brine (30 mL). The organic layer is dried over sodium sulfate, filtered, and concentrated in vacuo to give crude 65 as an oily residue. The product is purified by column chromatography on silica gel using a gradient of 0–3% of ethyl acetate in hexanes. The product thus obtained is crystallized from diethyl ether: hexanes 4:1 at −78° C. to give 65 (246 mg, 23%).

Synthesis of Compound 65

Birch Reduction/Alkylation, Method 2

For a description of synthetic methods employed in this example, see also Majetich, G.; Liu, S.; Fang, J.; Siesel, D.; Zhang, Y. *J. Org. Chem.* 1997, 62, 6928–6951. Lithium wire is added (cut in small pieces, 1000 mol %; 137 mmole; 948 mg) to ammonia (200 mL) at −78° C., the resulting blue solution is stirred at −78° C. for 15 min. A solution of 6-methoxy-1,4a-dimethyl-4,4a,9,10-tetrahydro-3H-phenanthren-2-one (53, 100 mol %; 13.7 mmole; 3.50 g) in tetrahydrofuran (100 mL) and 2-methyl-2-propanol (100 mol %; 13.7 mmole; 1.28 mL) is added via cannula over 10 min, the flask containing this solution is rinsed using tetrahydrofuran (40 mL), and the liquid is transferred to the reaction mixture via cannula and the resulting solution is stirred at −78° C. for 45 min. Iodomethane (2000 mol %; 273 mmole; 17 mL) is added slowly, and the reaction mixture is stirred at −78° C. for an additional 3 h. The reaction is quenched with an ammonium chloride solution (saturated aqueous, 150 mL) and the mixture is extracted using diethyl ether (3×100 mL). The organic layers are combined and washed successively using: water (2×100 mL), a sodium thiosulfate solution (saturated aqueous, 200 mL), an hydrochloric acid solution (0.25 N, 150 mL), and brine (200 mL). The organic layer is dried over magnesium sulfate, filtered, and concentrated in vacuo to give crude 65. Purification over silica gel using a gradient of 0–5% of ethyl acetate in hexanes gave 65 (1.72 g, 46%).

$^1$H NMR (300 MHz, CDCl$_3$): δ (ppm) 1.15 (s, 3H); 1.18 (s, 3H); 1.31 (s, 3H); 1.77–1.84 (m, 2H); 1.89–2.10 (m, 2H); 2.41–2.50 (m, 1H); 2.60–2.91 (m, 4H); 3.78 (s, 3H); 6.68–6.71 (m, 1H); 6.78–6.79 (m, 1H); 6.98–7.00 (m, 1H).

Synthesis of Compound 56b

The following example illustrates the synthesis of Compound 56b (4aS, 10aS; for a description of synthetic methods employed in this example, see also Paquette, L. A.; Ross, R. J.; Springer, J. P. *J. Am. Chem. Soc.* 1988, 110, 6192–6204). The same procedure can be used for the preparation of racemic 56 and enantiomer 56a (4aR, 10aR).

To a stirred solution of 65b (100 mol %, 4.21 mmole; 1.15 g) at 0° C. in dichloromethane (100 mL), trimethylsilyl trifluoromethanesulfonate (200 mol %; 8.41 mmol; 1.52 mL) is added and this mixture is stirred at 0° C. for 10 minutes. Triethylamine (250 mol %; 10.5 mmol; 1.46 mL) is added and the reaction mixture is stirred at 0° C. for 1.5 h (monitoired by TLC analysis). A solution of sodium bicarbonate (saturated aqueous, 100 mL) is added and the resulting mixture is extracted using diethyl ether (2×100 mL). The organic layers are combined and washed with brine (100 mL). The organic solution is dried over magnesium sulfate, filtered and concentrated in vacuo. The crude oil is dissolved in THF (50 mL) followed by addition of N-bromosuccinimide (110 mol %; 4.63 mmole; 825 mg). The mixture is stirred 20 min at room temperature, after which, 1,8-diazabicyclo[5.4.0]undec-7-ene (2400 mol %; 100 mmole; 15 mL) is added and the resulting mixture is stirred at reflux for 2 h. A solution of ammonium chloride (saturated aqueous, 100 mL) is added to the cooled reaction mixture. The resulting solution is extracted using diethyl ether (2×100 mL). The combined organic layers are washed successively using a solution of NH$_4$Cl (saturated aqueous, 2×100 mL) and brine (100 mL). The organic solution is dried over magnesium sulfate, filtered and concentrated in vacuo. Crude 56b is purified by column chromatography over silica gel using 3% of ethyl acetate in hexanes to give 56b (754 mg, 66%).

$^1$HNMR (300 MHz, CDCl$_3$): δ (ppm) 1.20 (s, 3H); 1.22 (s, 3H); 1.42 (s, 3H); 1.84–1.94 (m, 2H); 2.16 (dd, J=11 Hz and 4 Hz, 1H); 2.87–2.96 (m, 2H); 3.82 (s, 3H); 6.00 (d, J=10 Hz, 1H); 6.73 (dd, J=8 Hz and 3 Hz, 1H); 6.93 (d, J=3 Hz, 1H); 7.04 (d, J=8 Hz, 1H); 7.56 (d, J=10 Hz, 1H).

Synthesis of Compound 50a

The following example illustrates the synthesis of Compound 50a (4aR) (for a description of synthetic methods employed in this example, see also Cambie, R. C.; Mitchell, L. H. and Rutledge, P. S. *Aust. J. Chem.*, 1998, 51, 931–940). The same procedure can be used for the preparation of racemic 56 and enantiomer 50b (4aS). To a stirred solution of 56a (100 mlo %; 4.44 mmole; 1.20 g) in acetic acid (38 mL) at 7° C., is added, before freezing of the acetic acid, a solution of chrominium(VI) oxide (250 mol %; 11.1 mmole; 1.11 g) in a mixture of acetic acid (12 mL) and water (3.0 mL), dropwise over 10 min. The reaction mixture is stirred at 7° C. for 2 h before water (30 mL) was added along with solid sodium chloride (500 mg). The resulting mixture is extracted using diethyl ether (5×50 mL), the organic layers are combined and washed with a solution of saturated aqueous sodium bicarbonate (5×50 mL). The combined aqueous layers are back-extracted using diethyl ether (50 mL), the organic layers are combined and dried over magnesium sulfate, filtered and concentrated in vacuo. The residue is dissolved in tetrahydrofuran (40 mL) and added dropwise to a stirred solution of potassium tert-butoxide the combined organic layers are dried over magnesium sulfate, filtered concentrated in vacuo. The residue is purified by column chromatography over silica gel using a gradient of 0–10% of ethyl acetate in hexanes to give 50a (655 mg, 50%). Enantiomeric excess from annelation product (53) is conserved as determined by chiral HPLC. However, crystallization in diethyl ether:hexanes 4:1 or methanol:water 4:1 can afford enantioenriched material if required (determined by chiral HPLC).

Enantiomeric excess is determined using HPLC analysis with a chiral column (Chiralcel™ OD-RH, 4.6×150 mm): mobile phase isocratic 40% acetonitrile 60% water at 0.5 mL/min over 70 min, column temperature 25° C., on a Waters Alliance HPLC System 2795 using a PDA detector (200 to 600 nm).

$^1$H NMR (300 MHz, CDCl$_3$): δ (ppm) 1.57 (s, 3H); 1.59 (s, 3H); 1.69 (s, 3H); 3.95 (s, 3H); 6.27 (d, J=10 Hz, 1H); 7.00 (dd, J=9 Hz and 2 Hz, 1H); 7.08 (d, J=2 Hz, 1H); 7.20 (s, 1H); 7.37 (d, J=10 Hz, 1H); 8.20 (d, J=9 Hz, 1H). $^{13}$C NMR (75 MHz, CDCl$_3$): δ (ppm) 202.6, 179.0, 164.2, 150.8, 150.6, 143.0, 133.6, 130.1, 128.6, 121.6, 113.8, 111.0, 56.0, 48.4, 42.1, 39.3, 26.7, 21.5. MP: 167° C.–168° C.

6.4 Synthesis of Compounds 75, 76, 77, 78, and 79

Comounds 75, 76, 77, 78, and 79 have been synthesized by the following procedure.

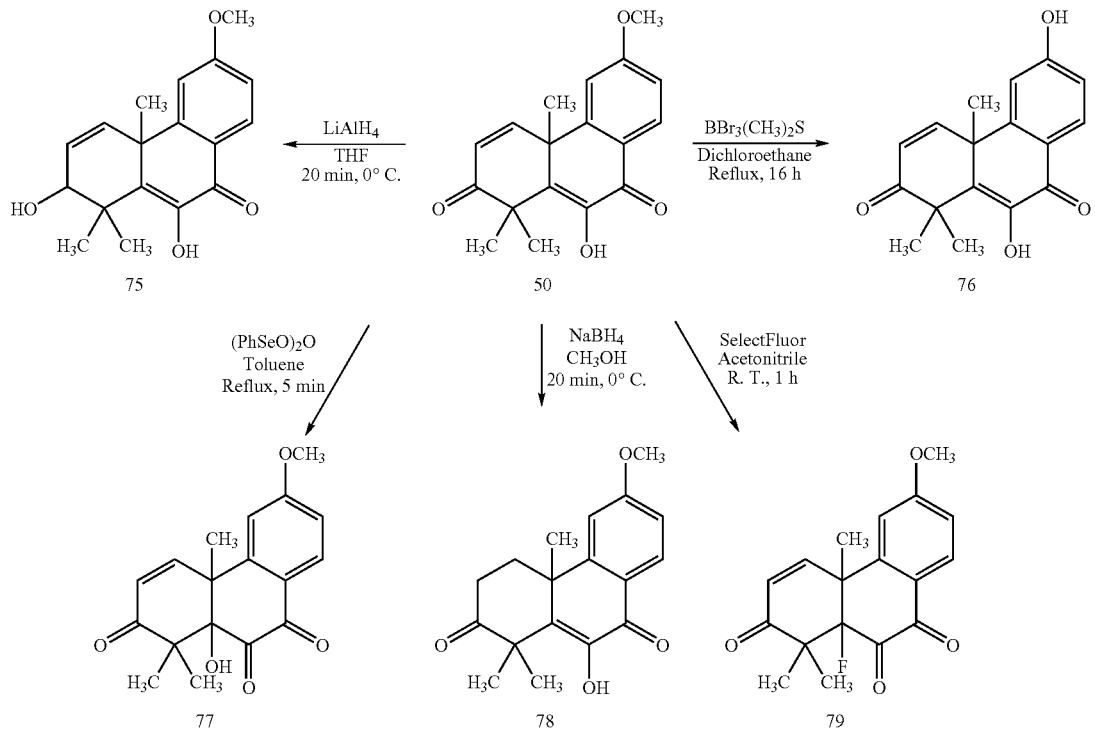

Scheme 9:

(310 mol %; 14.0 mmole; 28 mL of a 0.5 M solution in 2-methyl-2-propanol) and tetrahydrofuran (50 mL) at 0° C. The solution is stirred at 0° C. under oxygen atmosphere (balloon) for 1.5 hr. and then quenched with a solution of saturated aqueous ammonium chloride (50 mL). The resulting mixture is extracted using ethyl acetate (3×50 mL), and Synthesis of Compound 75

Referring to Scheme 9, lithium aluminum hydride (78 mol %; 0.052 mmole; 2 mg) is added slowly to a solution of compound 50 (100 mol %; 0.067 mmole; 20 mg) in dry tetrahydrofuran (3 ml) at 0° C., the mixture is stirred for 20 min. Ethyl acetate (25 ml) is added to the mixture and the organic layer is washed with a solution of ammonium chloride (saturated aqueous, 2×15 ml). The organic layer is dried over sodium sulfate, filtered and concentrated in vacuo. The crude product is purified by column chromatography over silica gel using a gradient of 0–20% ethyl acetate in hexanes to give the desired product 75 (2 mg, 10%).

$^1$H NMR (300 MHz, CDCl$_3$): δ (ppm) 0.71 (s, 3H); 1.20 (s, 3H); 1.53 (s, 3H); 3.27 (s, 1H); 3.94 (s, 3H); 6.16 (d, J=10 Hz, 1H); 6.85 (d, J=3 Hz, 1H); 6.96 (m, 1H); 7.19 (d, J=10 Hz, 1H); 8.19 (d, J=8 Hz, 1H).

Synthesis of Compound 76

Boron tribromide-methylsulfide complex (500 mol %; 1.00 mmole, 312 mg) is added to a solution of compound 50 (100 mol %; 0.201 mmole; 60 mg,) in dichloroethane (8 ml), the mixture is heated at reflux for 16 h. Ethyl acetate (40 ml) is added to the mixture and the organic layer is washed successively with HCl 1N (20 ml) and brine (20 ml). The organic layer is dried with sodium sulfate, filtered and concentrated in vacuo. The crude product is purified by column chromatography over silica gel using a gradient of 10–35% % ethyl acetate in hexanes to give the desired product 76 (21 mg, 37%).

$^1$H NMR (300 MHz, CDCl$_3$): δ (ppm) 1.49 (s, 3H); 1.52 (s, 3H); 1.62 (s, 3H); 5.49 (s, 1H); 6.19 (d, J=10 Hz, 1H); 6.85 (m, 1H); 7.00 (s, 1H); 7.10 (s; 1H); 7.28 (d, J=10 Hz, 1H); 8.07 (d, J=8 Hz, 1H).

Synthesis of Compound 77

Benzeneselenic anhydride (100 mol %; 0.033 mmole; 12 mg) is added to a solution of compound 50 (100 mol %; 0.033 mmole; 10 mg) in toluene (1 ml) and the mixture is heated at reflux for 5 min. Ethyl acetate (10 ml) is added to the mixture and the organic layer is washed successively with HCl 1N (5 ml) and brine (5 ml). The organic layer is dried with sodium sulfate, filtered and concentrated in vacuo. The crude product is purified by column chromatography over silica gel using a gradient of 15–35% ethyl acetate in hexanes to give the desired product 77 (5 mg, 50%).

$^1$H NMR (300 MHz, CDCl$_3$): δ (ppm) 1.45 (s, 3H), 1.60 (s, 3H); 1.65 (s, 3H); 2.58 (s, 1H); 3.94 (s, 3H); 6.19 (d, J=10 Hz, 1H); 6.94 (m, 1H); 7.01 (d, J=3 Hz, 1H); 7.20 (d, J=10 Hz, 1H); 8.18 (d, J=9 Hz, 1H).

Synthesis of Compound 78

Sodium borohydride (78 mol %; 0.052 mmole; 2 mg) is added slowly to a solution of compound 50 (100 mol %; 0.067 mmole; 20 mg) in methanol (3 ml) at 0° C. The mixture is stirred 20 min. Ethyl acetate (25 ml) is added to the mixture and the organic layer is washed with a solution of ammonium chloride (saturated aqueous, 2×15 ml). The organic layer is dried with sodium sulfate, filtered and concentrated in vacuo. The crude product is purified by column chromatography over silica gel using a gradient of 0–20% ethyl acetate in hexanes to give the desired product 78 (13 mg, 65%).

$^1$H NMR (300 MHz, CDCl$_3$): δ (ppm) 1.32 (s, 3H); 1.55 (s, 3H); 1.59 (s, 3H); 2.10 (m, 1H); 2.47 (m, 1H); 2.79 (t, J=9 Hz, 2H); 3.90 (s, 3H); 6.96 (m, 2H); 7.12 (s, 1H); 8.16 (d, J=10 Hz, 1H).

Synthesis of Compound 79

Selectfluor™ (100 mol %; 0.033 mmole; 12 mg) is added to a solution of compound 50 (100 mol %; 0.033 mmole; 10 mg) in acetonitrile (2 ml) and the mixture is stirred at room temperature for 1 h. Ethyl acetate (10 ml) is added to the mixture and the organic layer is washed with a solution of ammonium chloride (saturated aqueous, 2×15 ml). The organic layer is dried with sodium sulfate, filtered and concentrated in vacuo. The crude product is purified by column chromatography over silica gel using a gradient of 5–15% ethyl acetate in hexanes to give the desired product 79 (7 mg, 67%).

$^1$H NMR (300 MHz, CD$_3$OD): δ (ppm) 1.35 (s, 3H); 1.61 (s, 3H); 1.66 (s, 3H); 3.98 (s, 3H); 6.19 (d, J=10 Hz, 1H); 7.07 (m, 1H); 7.25 (d, J=3 Hz, 1H); 7.62 (d, J=10 Hz, 1H); 8.12 (d, J=9 Hz, 1H).

6.5 Synthesis of Pro-Drugs: Compound 72, 73, and 74

Compounds 72, 73, and 74 have been synthesized as described below.

Scheme 10

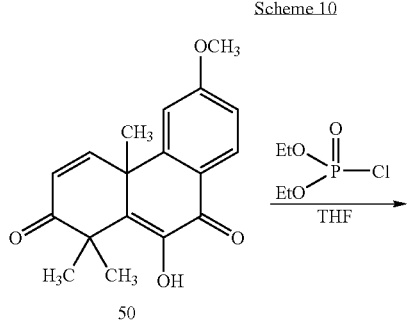

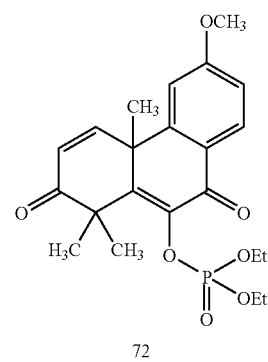

lp;4p

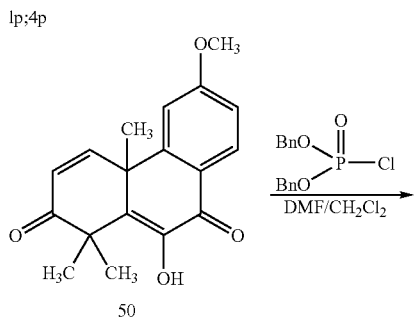

4.30–4.45 (m, 4H): 6.33 (d, J=10.3 Hz, 1H); 7.10 (dd, J=8.8 Hz and 2.4 Hz, 1H); 7.31 (d, J=2.4 Hz, 1H); 7.60 (d, J=10 Hz, 1H); 8.11 (d, J=8.8 Hz 1H).

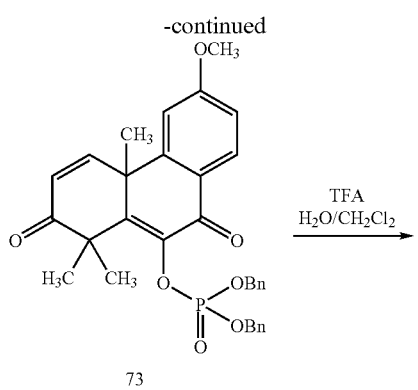

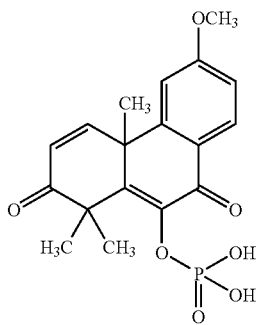

Synthesis of Compound 72

For a description of synthetic methods employed in this example, see also Mäntylä, A.; Garnier, T.; Rautio J.; Nevalainen T.; Vepsäläinen, J.; Koskinen, A.; Croft S. L.; Järvinen T.: *J. Med. Chem.*, 2004, 47, 188–195. Sodium hydride (200 mol %; 0.200 mmole; 10.0 mg) is added to a stirred solution of compound 7 (100 mol %; 0.100 mmole; 30.0 mg,) in THF (10 mL) at 0° C., and the reaction mixture is stirred at 0° C. for 30 min. Referring to Scheme 9, diethyl chlorophosphate is added and the reaction mixture is warmed to room temperature overnight. The reaction is quenched with water (10 mL), the resulting mixture is extracted using ethyl acetate (20 mL). The organic layer is washed with a solution of sodium bicarbonate (saturated aqueous, 20 mL). The combined aqueous solutions are extracted with ethyl acetate (20 mL). The combined organic phases are dried over magnesium sulfate, filtered and concentrated in vacuo. Crude diethyl phosphate 72 is purified by column chromatography over silica gel using a gradient of 30–50% ethyl acetate in hexanes to give pure 72 (31.1 mg, 71%).

$^1$H NMR (300 MHz, CD$_3$OD): δ (ppm): 1.42 (m, 6H); 1.57 (s, 3H): 1.64 (s, 3H); 1.72 (s, 3H); 3.96 (s, 3H);

Synthesis of Compound 73b

The following example can be used for the synthesis of 73b (4bS). The same procedure can be used for the synthesis of racemic 73 and enantiomer 73a (4bR). Freshly prepared chlorodibenzyl phosphate is obtained as follows: dibenzyl phosphate (200 mol %; 1.31 mmole; 366 mg) is dissolved in dichloromethane (20 mL), oxalyl chloride (200 mol %; 1.31 mmole; 120 μL) is added to the solution followed by two drops of N,N-dimethylformamide, the resulting solution is stirred for 45 min at room temperature, and then concentrated in vacuo. Dichloromethane (20 mL) is added to the solution which is concentrated again in vacuo. The chlorodibenzyl phosphate is dissolved in a minimum of dichloromethane (1 mL) and this solution is added to a stirred solution of compound 50b (100 mol %; 0.66 mmole; 196 mg) and sodium hydride (200 mol %; 1.31 mmole; 55 mg) in N,N-dimethylformamide (20 mL) at room temperature. The reaction mixture is stirred for 1 hr and a solution of sodium bicarbonate (saturated aqueous, 75 mL) is added. The mixture is extracted with ethyl acetate (2×75 mL). The combined organic layers are washed with brine (2×75 mL) and water (2×75 mL). The organic solution is dried over magnesium sulfate, filtered and concentrated in vacuo. Crude 73b is purified by column chromatography over silica gel using a gradient of 40–50% ethyl acetate in hexanes to give pure 73b (357.1 mg, 97

$^1$H NMR (300 MHz, CDCl$_3$): δ (ppm): 1.56 (s, 3H); 1.60 (s, 3H); 1.70 (s, 3H); 3.94 (s, 3H); 5.30 (m, 4H); 6.30 (d, J=10 Hz, 1H); 7.02 (m, 2H); 7.40 (m, 11H); 8.23 (d, J=9 Hz, 1H).

Synthesis of Compound 74b

The following example can be used for the synthesis of 74b (4bS). The same procedure can be used for the synthesis of racemic 74 and enantiomer 74a (4bR). To a stirred solution of 74b (100 mol %; 0.637 mmole; 357.1 mg) in dichloromethane (10 mL), 3 drops of water are added followed by trifluoroacetic acid (10 mL). The mixture is stirred for 2 hr at room temperature (monitored by TLC analysis). The solution is concentrated in vacuo, dichloromethane (20 mL) is added and again the solution is concentrated in vacuo. Diethyl ether (15 mL) is added and the reaction mixture is extracted with water (75 mL, HPLC grade). The aqueous layer is washed with diethyl ether (2×15 mL) and 5% methanol in ethyl acetate (10 mL) and then lyophilized. Crude 74b is purified by column chromatography over C18-reverse phase silica gel using a gradient 0–10% acetonitrile in water. The corresponding fractions are lyophilized to give pure 74b (132 mg, 53%).

$^1$H NMR (300 MHz, D$_2$O): δ (ppm): 1.46 (s, 3H); 1.49 (s, 3H); 1.59 (s, 3H); 3.82 (s, 3H); 6.23 (d, J=10 Hz, 1H); 6.96 (dd, J=9 and 2 Hz, 1H); 7.16 (d, J=2 Hz, 1H); 7.50 (d, J=10 Hz, 1H); 7.92 (d, J=9 Hz, 1H).

6.6 Synthesis of Compounds 80 and 81

Compounds 80 and Compound 81 have been synthesized as described below:

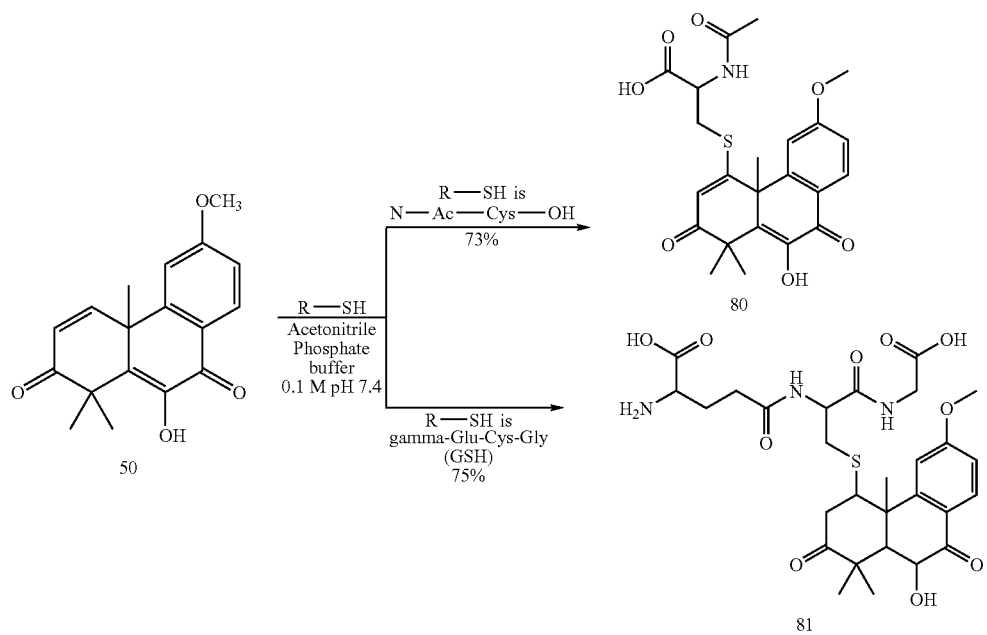

Scheme 11: Michael additions of cysteine derivatives on Compound 50

Synthesis of Compound 80 and Compound 81

Glutathione (γ-Glu-Cys-Gly, also called GSH; 970 mol %; 0.651 mmole; 200 mg) is added to a stirred solution of Compound 50 (100 mol %; 0.0671 mmole; 20.0 mg) in acetonitrile:aqueous phosphate buffer (0.1M, pH 7.4) 1:1 (6 mL). The reaction mixture is stirred at room temperature for 16 h, the volatiles are removed by rotary evaporation and the remaining aqueous mixture is lyophilized. The product is purified on a C18 cartridge using a gradient of 0–100% acetonitrile in water, the fractions containing the desired product are combined, the volatiles are removed by rotary evaporation and the remaining aqueous solution is lyophilized to give 30.3 mg, 75% of Compound 81. Product is reported has a mixture of diastereoisomers: $_1$H NMR (300 MHz, CD$_3$OD): δ (ppm) 1.35 (s, 3H); 1.36 (s, 3H); 1.46 (s, 3H); 1.46 (s, 3H; overlap with previous); 1.58 (s, 3H); 1.61 (s, 3H); 1.85–3.29 (m, 16H); 3.44–3.50 (m, 2H); 3.68–3.77 (m, 2H); 3.84 (s, 3H); 3.86 (s, 3H); 3.82–3.93 (m, 2H); 4.15 (dd, J=4 Hz and 10 Hz, 2H); 4.34 (dd, J=6 Hz and 9 Hz, 2H); 6.91 (t, J=2 Hz, 1H); 6.94 (t, J=3 Hz, 1H); 7.14 (d, J=2 Hz, 1 H); 7.21 (d, J=2 Hz, 1 H); 7.96 (d, J=9 Hz, 1H); 7.98 (d, J=9 Hz, 1H).

The same procedure can be used for the preparation of Compound 80 using N-acetyl-cysteine (913 mol %; 0.613 mmole; 100 mg) to give 22.7 mg, 73% of the desired compound, after purification. Product is reported has a mixture of diastereoisomers: $_1$H NMR (300 MHz, acetone-D6): δ (ppm) 1.51 (s, 3H); 1.52 (s, 3H); 1.55 (s, 3H); 1.55 (s, 3H; overlap with previous); 1.67 (s, 3H); 1.69 (s, 3H); 1.82 (s, 3H); 1.93 (s, 3H); 2.63–3.37 (m, 8H); 3.97 (s, 3H); 3.99 (s, 3H); 4.16 (dd, J=6 Hz and 8 Hz, 2H); 4.43–4.60 (m, 2H); 7.02–7.06 (m, 2H); 7.14 (dd, J=3 Hz and 5 Hz, 1H); 7.15 (d, J=8 Hz, 1H); 7.37 (d, J=2 Hz, 1H); 7.44 (d, J=2 Hz, 1H); 7.87 (s, 1H); 7.88 (s, 1H); 8.07 (d, J=9 Hz, 1H); 8.07 (d, J=9 Hz, 1H; overlap with previous).

6.7 Solubility of Phosphate Pro-Drug Compound 74

Material and Methods

To determine whether a compound is soluble in a solution, the solution was filtered on 0.2 μM polytetrafluoroethylene filters (Whatman Inc. Clifton, N.J., USA) and the compound concentration in the filtrate was measured by LC/MS and compared to the expected concentration. If the concentration of the compound in the filtrate was equal +/−15% to the expected concentration, the compound was judged to be soluble in the solution.

The detection of Compound 74 or Compound 50 by LC/MS was carried out using the HPLC system that consisted of a Waters Alliance quaternary gradient HPLC pump (Waters, Milford, Mass., USA) and a ZQ2000 single quadrupole mass spectrometer (Waters, Milford, Mass., USA). The column used was XTerra MS C18: 50×2.1 mm, 3.5 mm column at 20° C. Samples were injected and separated under the following conditions: The mobile phase "A" consisted of 5 mM ammonium formate, 0.1% formic acid in water and mobile phase "B" consisted of 5 mM ammonium formate, 0.1% formic acid in methanol. A linear gradient was applied as follows: 0 to 1 min, 94% "A" and 6% "B"; 1 to 4 min, 6% to 100% "B"; 4 to 8 min 100% "B"; 8 to 9 min, 100% "B" to 6% "B"; 9 to 12 min, 94% "A" and 6% "B". The Mass Spectrometer system consisted of a Waters ZQ2000 single quadrupole mass spectrometer (Waters, Milford, Mass., USA) equipped with an Electrospray Ionization Source (ES). The mass detector was operated in positive ion mode (ES+) and Selected Ion Recording mode (SIR). Compounds were detected at m/z equal to their respective molecular weight plus 1.

Results and Discussion

Without being bound by theory, the addition of a phosphate increases the solubility of a poorly soluble compounds. Even though, the phosphate prevents the compound from entering cells, the phosphate moiety is gradually removed by alkaline phosphatase in the plasma. Hence, the compound to which a phosphate is added is a pro-drug. For example, Compound 74 is the phosphate pro-drug of Compound 50. The solubility of compound Compound 50 is less than 0.1 mg/mL whereas the solubility of Compound 74 in water is equal or greater to 10 mg/mL. In vivo, because the phosphate is not removed instantly by alkaline phosphatase, the pro-drug has the time to disperse itself in the total blood volume. As the phosphate group is removed, the liberated drug is distributed in the tissue and enters the cells. Hence; the less soluble drug does not precipitate in the blood. The advantage of a pro-drug is that it can be injected in a smaller volume because it can be formulated at high concentration in aqueous solution.

6.8 The Conversion of Phosphate Pro-Drug Compound 74 into its Biologically Active Counterpart by Alkaline Phosphatases In Vitro The conversion into biologically active drug of phosphate pro-drugs by human placental alkaline phosphatase was measured in vitro using purified enzymes. Purified human placental alkaline phosphatase (Sigma-Aldrich Canada Ltd. Oakville, Ontario, Canada) was added at a concentration of 0.02 U/100 µL to a solution containing 15 µM of phosphate pro-drug, 20 mM Tris-HCl, pH 7.4 and 0.9% NaCl. The solutions were incubated for 10, 20 or 30 minutes. A solution containing 15 µM of phosphate pro-drug, 20 mM Tris-HCl, pH 7.4 and 0.9% NaCl was used a reference (time=0 minutes). To each solution, an equal volume (100 µL) of ice-cold acetonitrile was added, and then the mixture was vortexed and transferred to glass vials. A standard concentration curve of the pro-drug and the drug was prepared in 10 mM Tris-HCl, pH 7.4, 0.45% NaCl and 50% acetonitrile. All samples were immediately analyzed by LC/MS.

Figure 8:
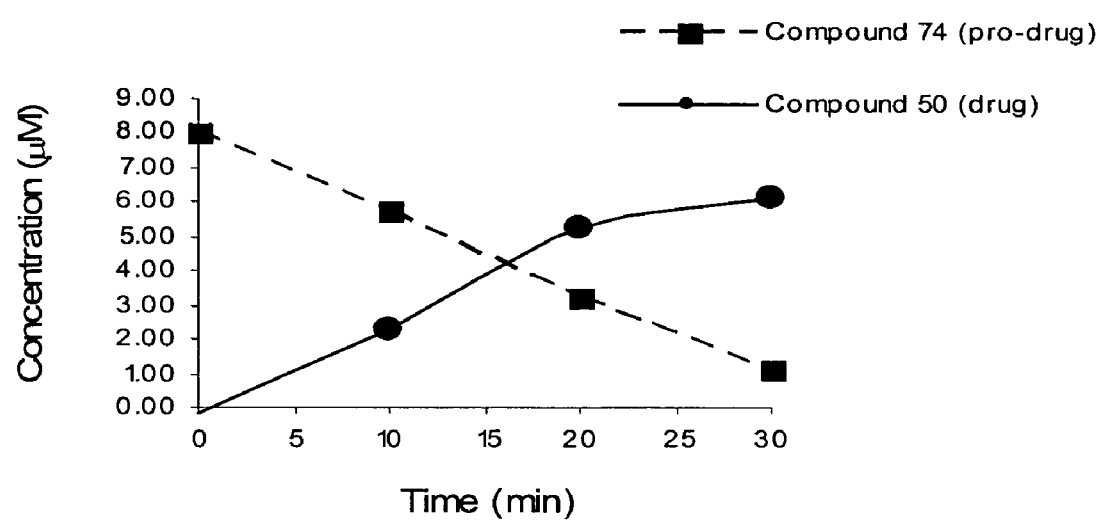
FIG. 8 shows the conversion of Compound 74 (pro-drug) into Compound 50 (drug) over time in the presence of human placental alkaline phosphatase.

As shown on FIG. 8, human placental alkaline phosphatase, can convert a fraction of the pro-drug Compound 74 present in solution into the drug Compound 50 within thirty minutes.

6.9 Compound 48 Selectively Induces Apoptosis

The ability of Compound 48 to selectively induce apoptosis in a variety of cancer cells is described below.

A wide range of anticancer agents, including chemotherapeutic agents, induces apoptosis in malignant cells in vitro. Without being bound by theory, apoptosis is a regulated process manifested by the activation of proteolytic cleavages resulting mostly from the action of a unique family of cysteine-proteases called caspases. To demonstrate the ability of Compound 48 to trigger caspase activation, lysates of cells treated with various concentrations of the Compound 48 were prepared. In particular, H 1299 non-small cell lung carcinoma cells, C33A cervical carcinoma cells, Mrc-5 normal lung fibroblasts (American Type Culture Collection, Manassas, Va. USA) and HMEC normal mammary epithelial cells (Clonetics San Diego, Calif., USA) were maintained in RPMI 1640 media supplemented with 10% fetal calf serum (Sigma-Aldrich Inc., St. Louis, Mo. USA). Cells were harvested and suspended at $0.6 \times 10^6$ cells/mL in media. A 45 µL aliquot of cell-suspension was added to each well of a 96-well microtiter plate (PerkinElmer Life Sciences Inc, Boston, Mass. USA). Cells were incubated overnight in a 5% $CO_2$, 95% humidity incubator at 37° C. and then, 5 µL of a 10% dimethyl sulfoxide (Sigma-Aldrich Inc., St. Louis, Mo. USA) solution containing various concentrations of Compound 48 or 5 µL of 10% dimethyl sulfoxide (solvent control) was added. The plates were further incubated for 16 hr. Cells were lysed in lysis buffer (50 mM Hepes pH 7.4; 0.1% Chaps; 10 mM EDTA; 10 mM DTT) and set aside for the caspase activity assay.

To demonstrate the caspase activity in the cell lysates, 0.35 µg of N-terminal biotinylated EGKRKGDEVDGVP-DRRASV peptide (Phoenix Pharmaceuticals Inc, Belmont, Calif. USA) was labeled with 1 mCi of $^{32}$P-γATP (PerkinElmer Life Sciences Inc, Boston, Mass. USA) using 250 units of Protein Kinase A catalytic subunit from bovine heart (Sigma-Aldrich Inc., St. Louis, Mo. USA) in 500 µL of HMK buffer (20 mM pH 7.5 Tris-HCl; 0.1 M NaCl; 12 mM $MgCl_2$; 1 mM DTT) at 37° C. for one hour. The reaction was then filtered using Sephadex G-10 Poly-Prep chromatography column (Amersham Biosciences, Inc, Piscataway, N.J., USA). The labeled peptide was coupled to 1.25 mL of streptavidin sepharose beads (Amersham Biosciences, Inc, Piscataway, N.J., USA) during 15 minutes at room temperature on a rotary mixer. The beads were washed seven times with 6 mL of 0.5M NaCl in PBS and resuspended in a total volume of 7.25 mL of 0.5 M NaCl PBS solution to which 9 mL of RPMI 1640 media was added. 96-well 0.45 µm MultiScreen-HV filter plates (Millipore, Bedford, Mass USA) were then prewetted with 200 µL of 0.5M NaCl in PBS and 40 µL of beads suspension was added to each well. Each well was washed five times with 200 µL of 0.5 M NaCl in PBS. In each well, 50 µL of cell lysate was added together with 12.5 µL of 0.5 M NaCl in 30% glycerol solution to each well. The plates were incubated at 30 C with shaking at 220 rpm overnight. On the next day, the filter plates containing the beads and the extract were placed on top of 96-well sample plates (PerkinElmer Life Sciences Inc, Boston, Mass. USA) containing 100 µL of Optiphase SuperMix liquid scintillant fluid (PerkinElmer Life Sciences Inc, Boston, Mass. USA) in each well and centrifuged at 1500 rpm for 10 minutes at room temperature. The number of radioactive counts per minute (cpm) in each well of the sample plate was measured using a liquid scintillation counter (PerkinElmer Life Sciences Inc, Boston, Mass. USA). The potency of caspase cascade activation was determined by the percentage increase in cpm in wells compared to cells treated with dimethyl sulfoxide only. Values two fold higher (200%) than control were considered positive and demonstrated that the compound triggered caspase activation in the cells.

Figure 2:
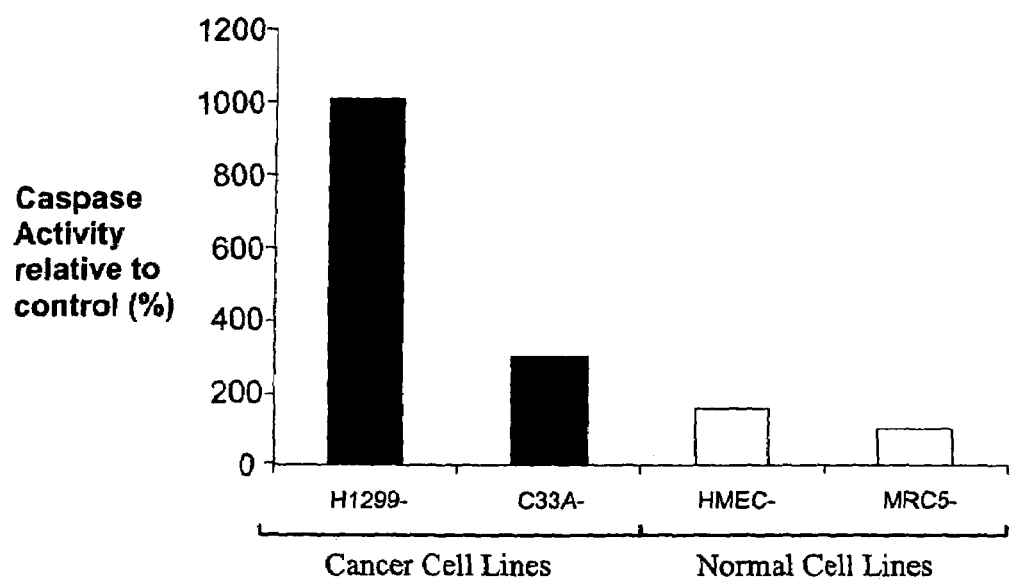
FIG. 2 is a bar graph depicting Caspase activity in different cell lines following 16 hours of in vitro treatment with 1.6 μM of Compound 48 (10-Hydroxy-6-methoxy-1,1,4a,7-tetramethyl-1H,4aH-phenanthrene-2,9-dione).

As depicted in FIG. 2, results showed that caspases were activated in the cancer cell lines H1299 and C33A and not in the normal cell line following 16 hours incubation with 1.6 µM of Compound 48. These results demonstrate that Compound 48 induces apoptosis selectively in cancer cells and is useful for treating or preventing cancer, particularly lung or cervical cancer.

6.10 Compound 48 Selectively Affects Cancer-Cell Viability

To demonstrate the effect of Compound 48 on cell viability, cellular ATP levels were measured following Compound 48 treatment. H1299 non-small cell lung carcinoma cells, C33A cervical carcinoma cells, Mrc-5 normal lung fibroblasts (American Type Culture Collection, Manassas, Va. USA) and HMEC normal mammary epithelial cells (Clonetics San Diego, Calif., USA) were cultured in RPMI 1640 media supplemented with 10% fetal calf serum (Sigma-Aldrich Inc., St. Louis, Mo. USA). The four cells lines were plated in 96-well microtiter plates (PerkinElmer Life Sciences Inc, Boston, Mass. USA) at a confluency that allowed them to reach confluence after 4 days of growth. One day after plating, the cells were treated either with 10 µM etoposide, 100 nM staurosporine or 1.6 µM of Compound 48. Stock solutions of each compound were prepared in dimethyl sulfoxide (Sigma-Aldrich Inc., St. Louis, Mo. USA), diluted in media then added to the cells. The total dimethyl sulfoxide on the cells was 1%. After 3 days of incubation, the ATP levels in the cells were quantified using the luminescent ViaLight detection system (Bio-Whittaker, Md., USA). The results were plotted relative to untreated control cells, which were set at 100.

Figure 3:
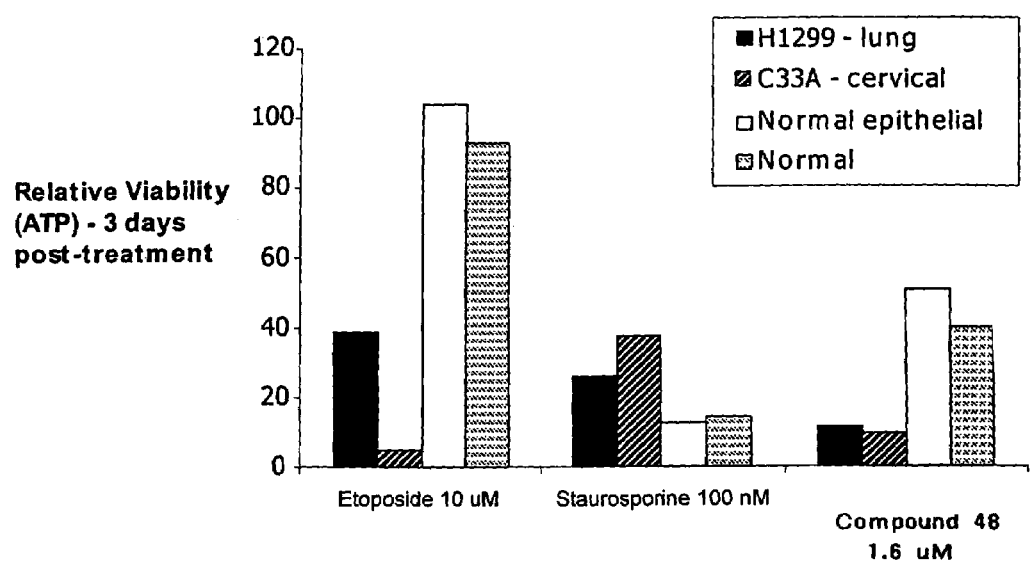
FIG. 3 is a bar graph depicting cell survival of different cell types following 72 hours of in vitro treatment with Compound 48 (10-Hydroxy-6-methoxy-1,1,4a,7-tetramethyl-1H,4aH-phenanthrene-2,9-dione).

As depicted in FIG. 3, Compound 48 has a significantly greater effect on the ATP levels in cancer cells than in normal cells. After 72 hours, treatment with 1.6 µM Compound 48 was significantly more effective at lowering ATP levels in cells of the cancer cell line H1299 and C33A compared with cells of the lines HMEC and MRC-5. Control compounds were tested to illustrate the significance of this effect. The anti-cancer drug etoposide as well as Compound 48, but not the protein kinase inhibitor staurosporine, are selectively cytotoxic towards cancer cells, particularly lung and cervical cancer. These results demonstrate that Compound 48 is selectively cytotoxic to cancer cells and is useful for treating or preventing cancer, particularly lung or cervical cancer.

6.11 Anti-Oncogenic Effects of Compound 50

6.11.1 Effects of Compound 50A and Compound 50B on Cancer Cell Viability In Vitro To demonstrate the effect of Compounds 50a and 50b, respectively, on cell viability, cellular ATP levels were measured before and after treating cell lines with each compound. The following cell lines were used: A549 human non-small cell lung carcinoma; C33A human cervical carcinoma; H1299 human non-small cell lung carcinoma; Hep-3B human hepatocellular carcinoma; MIA-Paca-2 human pancreatic carcinoma; PC-3 human prostatic adenocarcinoma (American Type Culture Collection, Manassas, Va., USA); HMEC normal human mammary epithelial cells; HUVEC normal human umbilical vein endothelial cells; and NHBE normal human bronchial epithelial cells (Cambrex Bio Science, Rockland, Me., USA). All tumor cell lines were cultured in RPMI 1640 media supplemented with 10% fetal bovine serum (FBS, Hyclone, Logan, Vt., USA), 100 U/mL penicillin, 100 µg/mL streptomycin and 2 mM L-glutamine (Invitrogen, Carlsbad, Calif., USA). HMEC, HUVEC and NHBE cell lines were cultured in MEGM, EGM-2 and BEGM media, respectively (Cambrex Bio Science, Rockland, Me., USA). The cell lines were plated in 96-well microtitre plate at a density of $2-4\times10^3$ cells per well. After 16 hours, the cells were treated with various concentrations of Compound 50a or Compound 50b. Stock solutions of Compound 50a and Compound 50b, respectively, were prepared in dimethyl sulfoxide at a concentration of 5 mM. Serial dilutions were prepared in RPMI, 10% FBS and 2% DMSO and then added to the cells. The total DMSO in the cell cultures was 1%. After 72 hours of incubation, the ATP levels in the cells were quantified using the Vialight HS kit (Cambrex Bio Science, Rockland, Me., USA). The results were plotted relative to untreated control cells, which were set at a value of 100. The IC50s were determined using a best-fit sigmoidal dose response curve with variable slope.

As depicted in Table 5, Compound 50a and Compound 50b showed greater efficacy in decreasing cellular ATP levels in the cancer cell lines than in normal cell lines. These results demonstrate that Compound 50a and Compound 50b are selectively cytotoxic to cancer cells and are useful for treating or preventing cancer, particularly NSCL-LC carcinoma, NSCL-adrenocarcinoma, liver cancer, pancreatic cancer, cervial cancer, prostate cancer or lung cancer.

TABLE 5

Anti-oncogenic effects of Compound 50a and Compound 50b

|  | Cell line | Tissue type | Species | IC50 of Compound 50a (µM) | IC50 of Compound 50b (µM) |
|---|---|---|---|---|---|
| Tumor | H1299 | NSCL-LC carcinoma | Human | 0.550 | 0.230 |
|  | A549 | NSCL-adrenocarinoma | Human | 0.630 | 0.580 |
|  | Hep 3B | Liver | Human | 0.970 | 0.770 |
|  | MIA-Paca-2 | Pancreas | Human | 0.660 | 0.250 |
|  | C33A | Cervix | Human | 0.500 | 0.450 |
|  | PC-3 | Prostate | Human | 0.370 | 0.350 |
| Normal | HMEC | Breast epithelial | Human | 2.300 | 2.100 |
|  | HUVEC | Endothelial | Human | 1.700 | 1.300 |
|  | NHBE | Bronchial epithelial | Human | 1.200 | 1.200 |

*Measurement of ATP levels were taken 72 h post-treatment and compared to untreated cells.

6.11.2 Effect of Compound 50 on Growth of Cervical Tumor Cells In Vivo

To demonstrate the anti-tumor activity of Compounds 50 in vivo, CB17 SCID/SCUD female mice (Charles River, Mass., USA) that were injected with C33A human cervical cancer cells were used. The resultant mice are a model for a human having cervical cancer.

The C33A human cervical cancer cells were maintained in RPMI supplemented with 10% inactivated fetal bovine serum and 1% penicillin-streptomycin-L-Glutamine, under 5% $CO_2$ at 37° C., and passaged twice a week. The cells were grown at a confluency lower than 70% and then collected with Trypsin (Bio-Whittaker, Md., USA). The cells were then centrifuged and washed twice using phosphate buffered saline solution (PBS) and resuspended in PBS at $2\times10^6$ cells per 100 µl. Viability was examined by staining with Trypan Blue and only flasks with cell viability of greater than 95% were used for in vivo studies.

C33A cells were transplanted subcutaneously into the flank of female CB17 SCID/SCID mice. Each mouse was inoculated with a suspension of $2\times10^6$ tumor cells per 100 µL on day zero. The following six treatment groups of ten mice each were used: (a) a negative control group treated with intravenous (i.v.) injection of vehicle, (b) a negative control group treated with intraperitoneal (i.p.) injection of vehicle, (c) a positive control group treated with i.p. injection of Cisplatin, (d) a group treated with i.v. injection of a Compound 50, (e) a group treated with i.p. injection of Compound 50, and (f) a group treated with subcutaneous (s.c.) injection of Compound 50.

Treatment started on day thirteen after C33A cells transplantation for Compound 50 treated groups and on day fourteen for Cisplatin treated group. Compound 50 was administered i.v., i.p., and s.c. once daily for five consecutive days at a dose of 10, 15 and 30 mg/kg, respectively. Compound 50 was prepared as a working solution of 1.5 mg/mL in a vehicle solution of 20% Cremaphor EL (Sigma, St. Louis, Mo., USA), 10% Ethanol and 5% Dextrose (Abbot Laboratories, QC, Canada). The negative control groups were treated with vehicle alone. The positive control group was treated once every 3 days for fifteen days at a dose of 3.5 mg/kg. Cisplatin was formulated in PBS on each day of the injection and was administered i.p.

Figure 4:
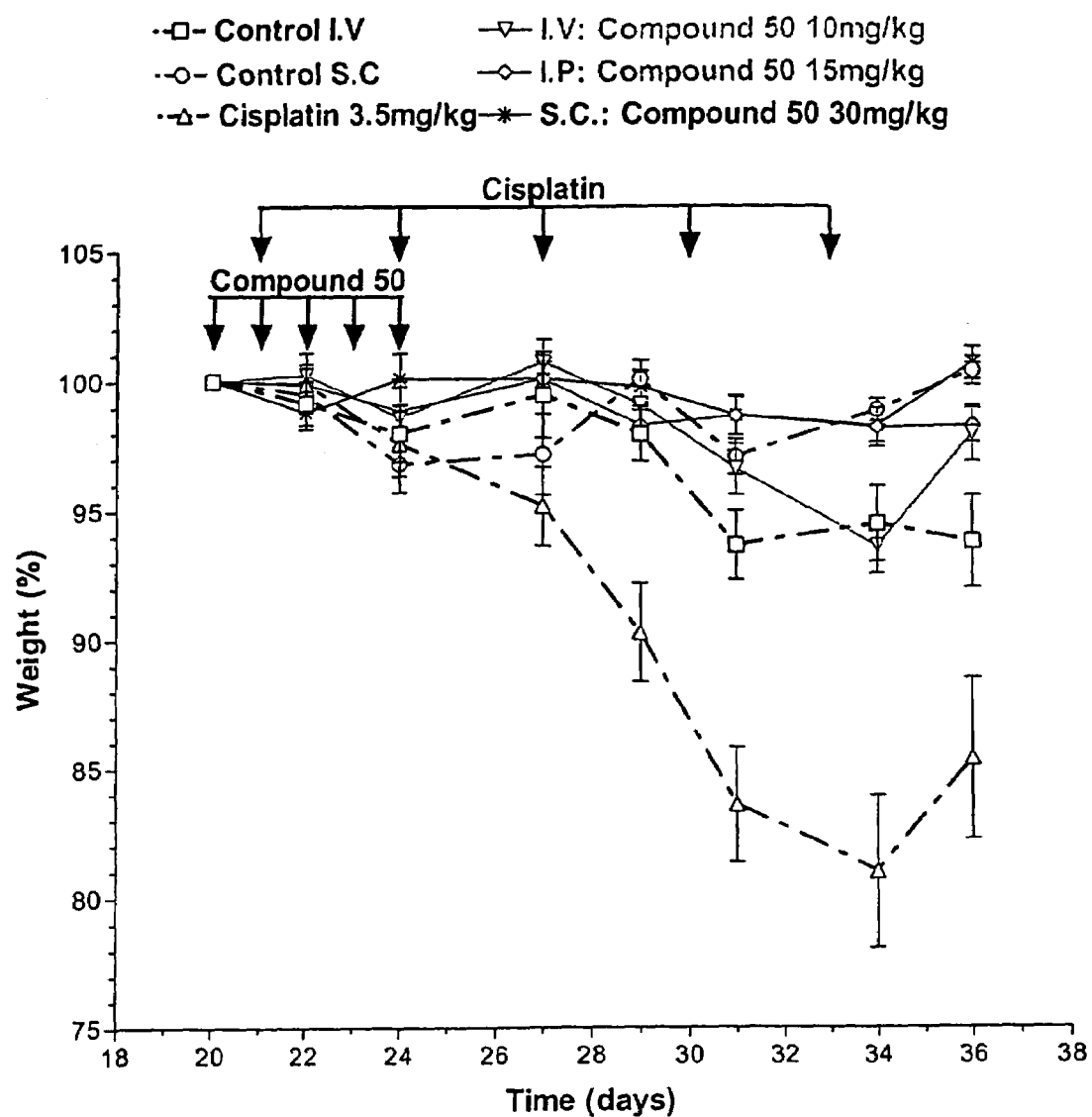
FIG. 4 is a graph depicting the weight of mice following treatment with Cisplatin or Compound 50. The time-points of administration of Cisplatin or Compound 50 are indicated by arrows on top of the graph.
Figure 5:
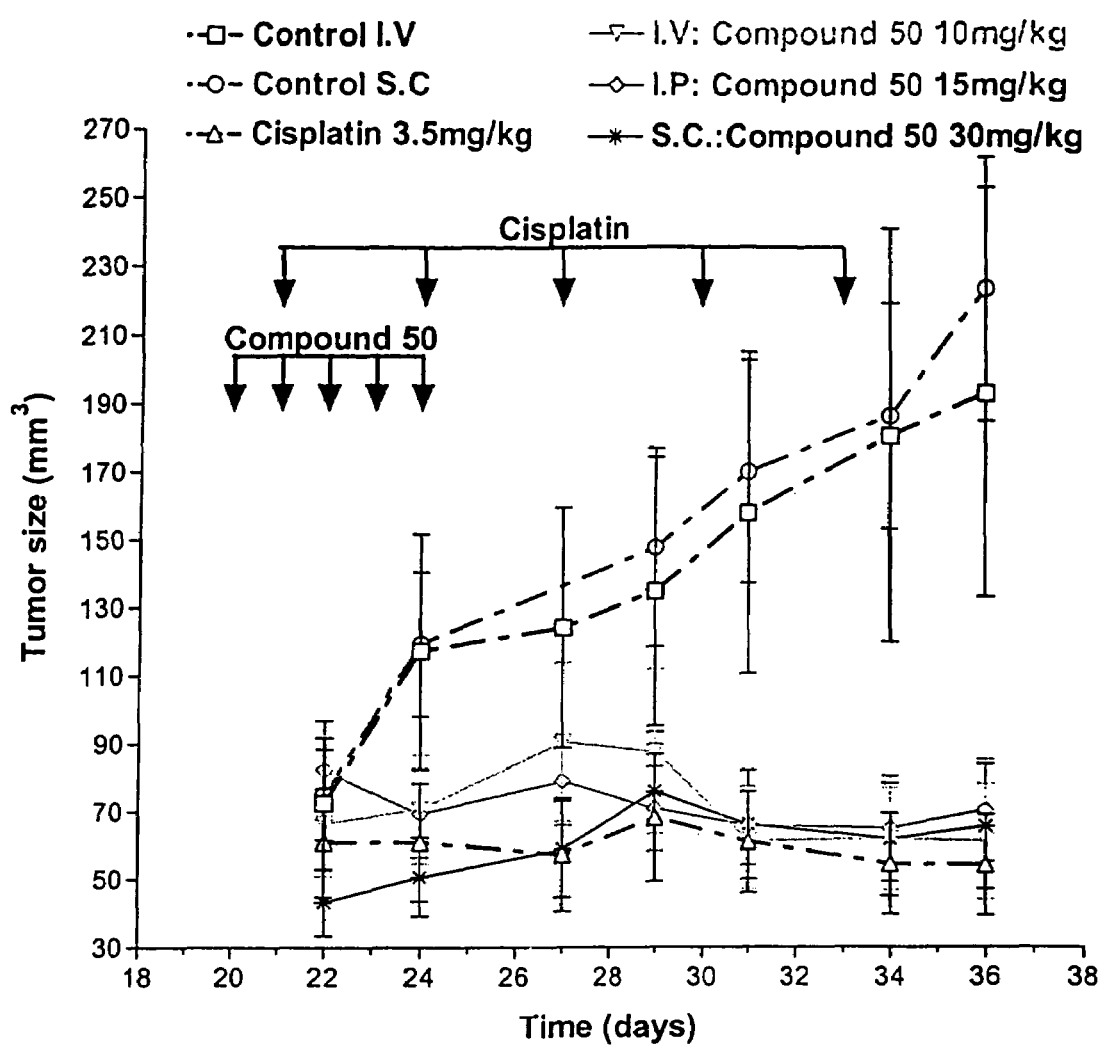
FIG. 5 is a graph depicting the tumor size in mice following treatment with Cisplatin or Compound 50. The time-points of administration of Cisplatin or Compound 50 are indicated by arrows on top of the graph.

The mice were weighed and the tumors measured on day 13 and every 2 to 3 days after treatment commenced. Observations continued for 36 days after initial tumor implantation. The changes in body weight and in the calculated tumor volume were plotted (FIGS. 4 and 5). Statistical analysis was performed using GraphPad Prism (GraphPad Software Inc., San Diego, Calif.). Two-way ANOVA was used to determine how the treatment affected tumor growth over time. Following the two-way ANOVA, post-tests were performed using the Benferroni method to determine the statistical difference between the mean tumor-size of the two groups being compared on every day that the tumors were measured. Four animals in the negative control injected i.v. with vehicle and two animals in the group treated i.v. with Compound 50 died during the observation period. Therefore, the data collected from these animals were excluded from all calculations and the total number of animals in the groups changed to six for the negative control injected i.v. with vehicle and eight for the group treated i.v. with Compound 50.

As shown in FIG. 4, mice treated with Compound 50 experienced a non-significant change in body weight, whereas Cisplatin treated positive control group experienced a weight loss of 19% on day 34.

As shown in FIG. 5, Compound 50 administered i.v. or i.p. at a dose of 10 or 15 mg/kg, respectively, once a day for five days resulted in a significant reduction ($p<0.001$) in tumor growth compared to mice treated i.v. with vehicle only. On day 36, animals treated i.v. with 10 mg/kg of Compound 50 had significantly ($p<0.05$) smaller mean tumor-size than animals treated with vehicle only. Similarly, animals treated i.p. with Compound 50 had a significantly ($p<0.05$) smaller mean tumor-size than animals treated with vehicle on day 34 and day 36. Furthermore, Compound 50 administered s.c. at a dose of 30 mg/kg once a day for five days resulted in a significant reduction ($p<0.001$) in tumor growth compared to mice treated s.c. with vehicle alone. Animals treated s.c. with Compound 50 had a significantly smaller mean tumor-size than animals treated with vehicle on day 34 ($p<0.01$) and day 36 ($p<0.001$).

As indicated in FIG. 5, Compound 50 significantly reduces the human cervical tumors implanted in SCID mice, an art-accepted model for human cervical cancer. Accordingly, Compound 50 is useful for inhibiting the growth of a cancer cell, particularly a cervical cancer cell, and for treating or or preventing cancer, particularly cervical cancer, in a patient.

6.12 Anti-Fungal Biological Activity of Compound 50

6.12.1 Effect of Compound 50 on the Growth of the Yeast *Saccharomyces Cerevisiae*

Figure 6:
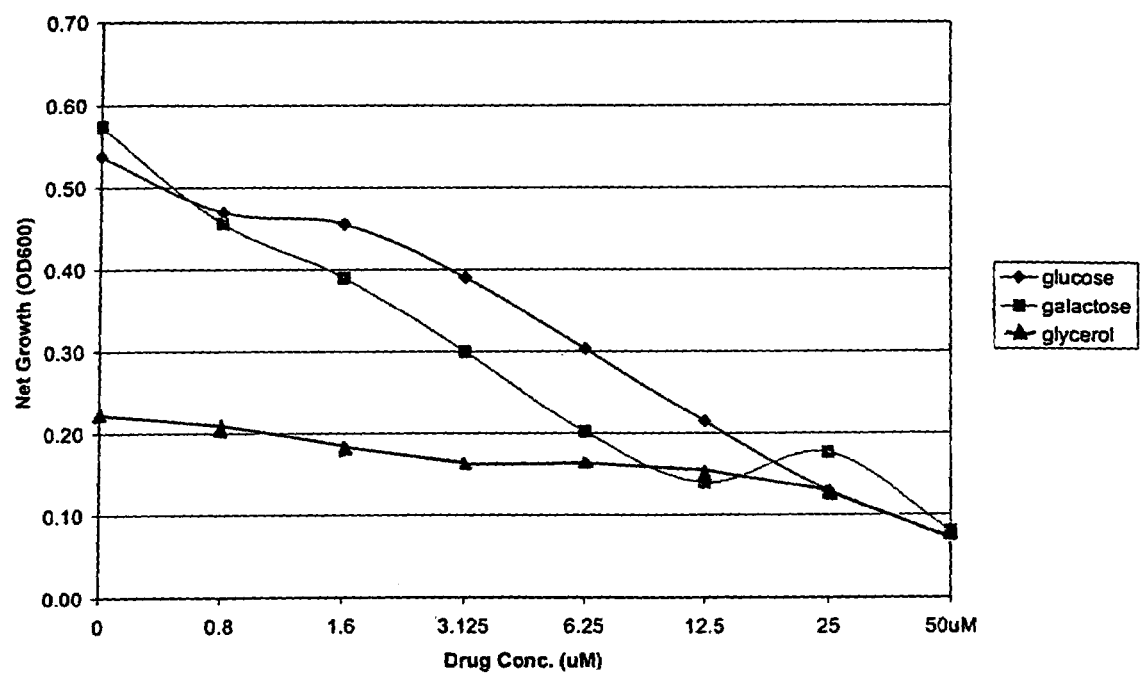
FIG. 6 is a graph depicting the net growth of *Saccharomyces cerevisiae* following treatment with Compound 50.

To demonstrate that Compound 50 inhibits the growth of the yeast *Saccharomyces cerevisiae*, the strain W303a was cultured in YEP media, containing Bacto Yeast Extract and Bacto Peptone (Becton Dickinson Microbiology Systems, Sparks, Md., USA) and supplemented with one of three different carbon sources, 2% glucose (Sigma Chemical Co. St. Louis, Mo., USA), 2% galactose (BDH Laboratory Supplies, Poole, England), or 2% glycerol (EM Science, Gibbstown, N.J., USA). Yeast cells were first cultured overnight in 10 mL of YEP glucose-containing medium at 30° C. The following day, 5 µL of the overnight culture ($5-6\times10^3$ cells) was added to 100 µL of YEP media supplemented with 2% of one of the three carbon sources mentioned above in a 96-well microtitre plate. To these cultures a dilution series of Compound 50 was added. Compound 50 was prepared as a stock solution in 100% dimethyl sulfoxide (DMSO) at a concentration of 10 mM. Serial dilutions were prepared in distilled water. The final DMSO concentration in each well was 0.5%. Yeast cells were grown at 30° C. and cell growth was monitored by reading the $OD_{600}$ (optical density at 600 nm) with a Tecan ULTRA plate reader (TECAN U.S. Inc., Research Triangle Park, N.C., USA). As depicted in FIG. 6, Compound 50 significantly inhibited growth of the yeast *Saccharomyces cerevisiae* in dose-dependent manner. Accordingly, Compound 50, an illustrative Diterpenoid Compound, is useful for inhibiting the growth of a fungus or treating a fungal infection.

6.12.2 Effect of Compound 50 on Growth of the Fungus *Candida Albicans*

Figure 7:
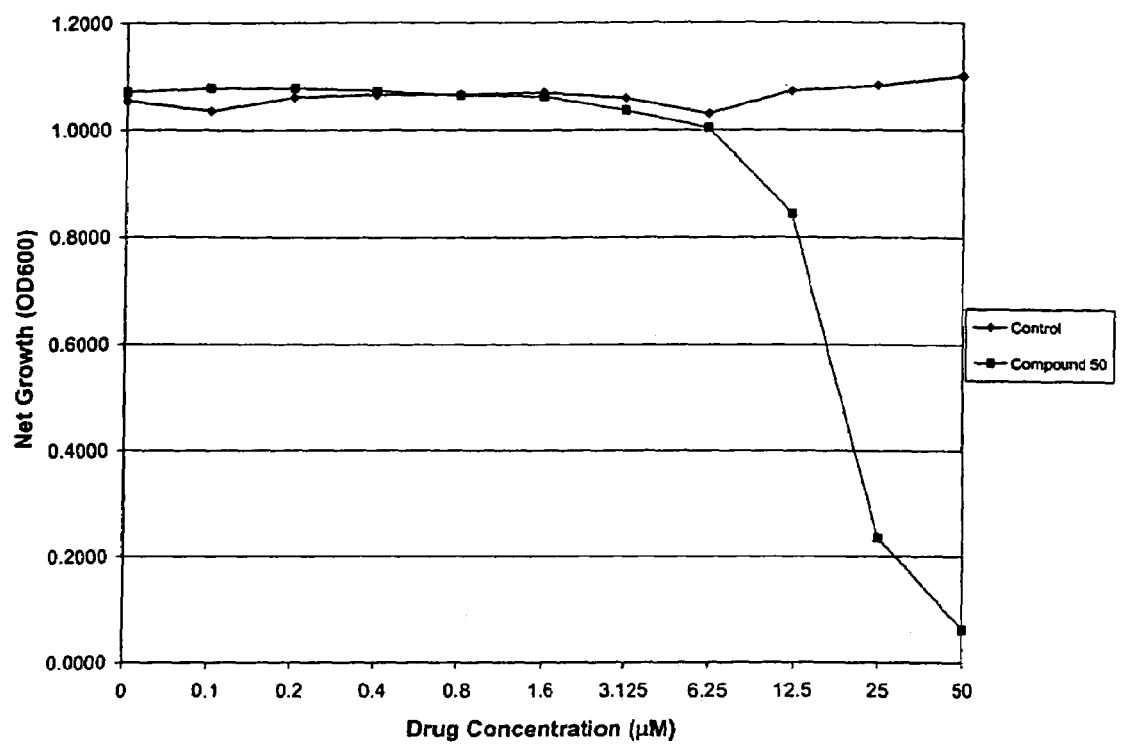
FIG. 7 is a graph depicting the net growth of *Candida albicans* following treatment with Compound 50.

To demonstrate that Compound 50 inhibits the growth of the fungus *Candida albicans*, the strain ATCC 10231 was cultured in YEP media, containing Bacto Yeast Extract and Bacto Peptone (Becton Dickinson Microbiology Systems, Sparks, Md., USA) and supplemented with 2% glucose (Sigma Chemical Co. St. Louis, Mo., USA). Fungus cells were first cultured overnight in 10 mL of YEP glucose-containing medium at 30° C. The following day, 5 µL of the overnight culture ($5-6\times10^3$ cells) was added to 100 µL of YEP glucose-containing medium in a 96-well microtitre plate. To these cultures a dilution series of Compound 50 was added. Compound 50 was prepared as a stock solution in 100% dimethyl sulfoxide (DMSO) at a concentration of 10 mM. Serial dilutions were prepared in distilled water. The final DMSO concentration in each well was 0.5%. Fungus cells were grown at 30° C. and cell growth was monitored by reading the $OD_{600}$ (optical density at 600 nm) with a Tecan Ultra plate reader (TECAN U.S. Inc. Research Triangle Park, N.C., USA). As depicted in FIG. 7, Compound 50 significantly inhibited growth of the fungus *Candida albicans* in a dose-dependent manner. Accordingly, Compound 50, an illustrative Diterpenoid Compound, is useful for inhibiting the growth of a fungus or treating a fungal infection.

6.13 Biological Activity of Compounds 66, 67, 68, 69 and 70

6.13.1 Effects of Compounds 66, 67, 68, 69 and 70 on Cancer Cell Viability In Vitro To demonstrate the effect of compounds 66, 67, 68, 69 and 70 on cell viability, cellular ATP levels were measured before and after treating cell lines with each compound. The selected tumor cell lines included C33A human cervical carcinoma and H1299 human non-small cell lung carcinoma (American Type Culture Collection, Manassas, Va., USA). The cell lines were cultured in RPMI 1640 media supplemented with 10% FBS (Hyclone, Logan, Vt., USA), 100 U/mL penicillin, 100 μg/mL streptomycin and 2 mM L-glutamine (Invitrogen, Carlsbad, Calif., USA). The cell lines were plated in 96-well microtitre plate at a density of $2-4 \times 10^3$ cells per well. After 16 hours, the cells were treated with various concentrations of compound 66, 67, 68, 69 and 70, respectively. Stock solutions of compounds 66, 67, 68, 69 and 70 were prepared in dimethyl sulfoxide at a concentration of 5 mM. Serial dilutions were prepared in RPMI, 10% FBS and 2% DMSO and then added to the cells. The total DMSO on the cells was 1%. After 72 hours of incubation the ATP levels in the cells were quantified using Vialight HS kit (Cambrex Bio Science, Rockland, Me., USA). The results were plotted relative to untreated control cells, which were set at a value of 100. The IC50s were determined using a best-fit sigmoidal dose response curve with variable slope.

As depicted in Table 6, treatment with Compound 66, 67, 68, 69 or 70 decreased the cellular ATP levels in the cancer cell lines. These results demonstrate that Compounds 66, 67, 68, 69 and 70 inhibit the growth of a cancer cell, particularly a C33A human cervical carcinoma cell and H1299 human non-small cell lung carcinoma cell, and are useful for treating or preventing cancer, particularly human cervical carcinoma and human non-small cell lung carcinoma, in a patient.

TABLE 6

The IC50s in μM of Compounds 66, 67, 68, 69 and 70 for anti-oncogenic effects*.

| Compound | Formula | H1299 | C33A |
|---|---|---|---|
| 66 | I | 1.440 | 1.550 |
| 67 | I | 0.950 | 1.190 |
| 68 | I | 2.070 | 2.530 |
| 69 | I | 1.360 | 0.870 |
| 70 | III | 16.810 | 15.890 |

*Measurement of ATP levels were taken 72 h post-treatment and compared to untreated cells.

6.14 Effects of Compounds 72, 73 and 76 on Cancer Cell Viability In Vitro

To demonstrate the effect of pro-drugs Compounds 72 and 73, and analogue Compound 76 on cancer cell viability, cellular ATP levels were measured before and after treating H1299 and C33A cancer cell lines as described in section 6.8.1 of this application.

As depicted in Table 7, these compounds were efficient in decreasing cellular ATP levels in H1299 and C33A cancer cell lines. These results demonstrate that Compounds 72, 73 and 76 inhibit the growth of a cancer cell and are useful for treating or preventing cancer, particularly, human cervical carcinoma and human non-small cell lung carcinoma, in a patient.

TABLE 7

The IC50s μM of Compounds 72, 73, and 76 for anti-oncogenic effects

| Compound | H1299 | C33A |
|---|---|---|
| 72 | 0.997 | 0.212 |
| 73 | 1.544 | 0.655 |
| 76 | 0.302 | 0.200 |

6.15 Effects of Compounds 80 and 81 on Cancer Cell Viability In Vitro

To demonstrate the effect of analogues Compound 80 and Compound 81 on cancer cell viability, cellular ATP levels were measured before and after treating H 1299 and C33A cancer cell lines as described above in section 6.13.1.

As depicted in Table 8, these compounds were efficient in decreasing cellular ATP levels in H1299 and C33A cancer cell lines. These results demonstrate that Compounds 80 and 81 inhibit the growth of a cancer cell and are useful for treating or preventing cancer, particularly, human cervical carcinoma and human non-small cell lung carcinoma, in a patient.

TABLE 8

The IC50s [μM] of Compounds 80 and 81 for anti-oncogenic effects

| Compound | H1299 | C33A |
|---|---|---|
| 80 | 0.208 | 0.216 |
| 81 | 0.155 | 0.186 |

6.16 Effect of Compound 50, 50A, 50B and 74A on Growth of Colon Carcinoma Tumor Cells In Vivo To demonstrate the anti-tumor activity of Compounds 50, 50a, 50b and 74a in vivo, CB17 SCID/SCID female mice (Charles River, Mass., USA) that were injected with SW480 human colon carcinoma cancer cells were used. The resultant mice are a model for a human having colon carcinoma cancer.

The SW480 human colon carcinoma cancer cells were maintained in RPMI supplemented with 10% inactivated fetal bovine serum and 1% penicillin-streptomycin-L-Glutamine, under 5% $CO_2$ at 37° C., and passaged twice a week. The cells were grown at a confluency lower than 70% and then collected with Trypsin (Bio-Whittaker, Md., USA). The cells were then centrifuged and washed twice using phosphate buffered saline solution (PBS) and resuspended in PBS at $1 \times 10^6$ cells per 100 μl. Viability was examined by staining with Trypan Blue and only flasks with cell viability of greater than 95% were used for in vivo studies.

SW480 cells were transplanted subcutaneously into the flank of female CB 17 SCID/SCID mice. Each mouse was inoculated with a suspension of $1 \times 10^6$ tumor cells per 100 μL on day zero. The following five treatment groups of ten mice each were used: (a) a negative control group treated with intravenous (i.v.) injection of vehicle, (b) a group treated with i.v. injection of a Compound 50, (c) a group treated with i.v. injection of a Compound 50a, (d) a group treated with i.v. injection of Compound 50b, (e) a group treated with i.v. injection of Compound 74a.

Treatment started on day twelve after SW480 cells transplantation and Compounds 50, 50a, 50b and 74a were administered i.v. once daily for five consecutive days at a dose of 10, 10, 10 and 50 mg/kg, respectively. Compound 50, 50a and 50b were prepared as a working solution of 1.5 mg/mL in a vehicle solution of 20% Cremaphor EL (Sigma, St. Louis, Miss., USA), and 10% Ethanol. Compound 74a was prepared as a working solution of 5 mg/mL in a vehicle solution of 5% Dextrose (Abbot Laboratories, QC, Canada). The negative control groups were treated with vehicle solution of 20% Cremaphor EL and 10% Ethanol alone.

Figure 9:
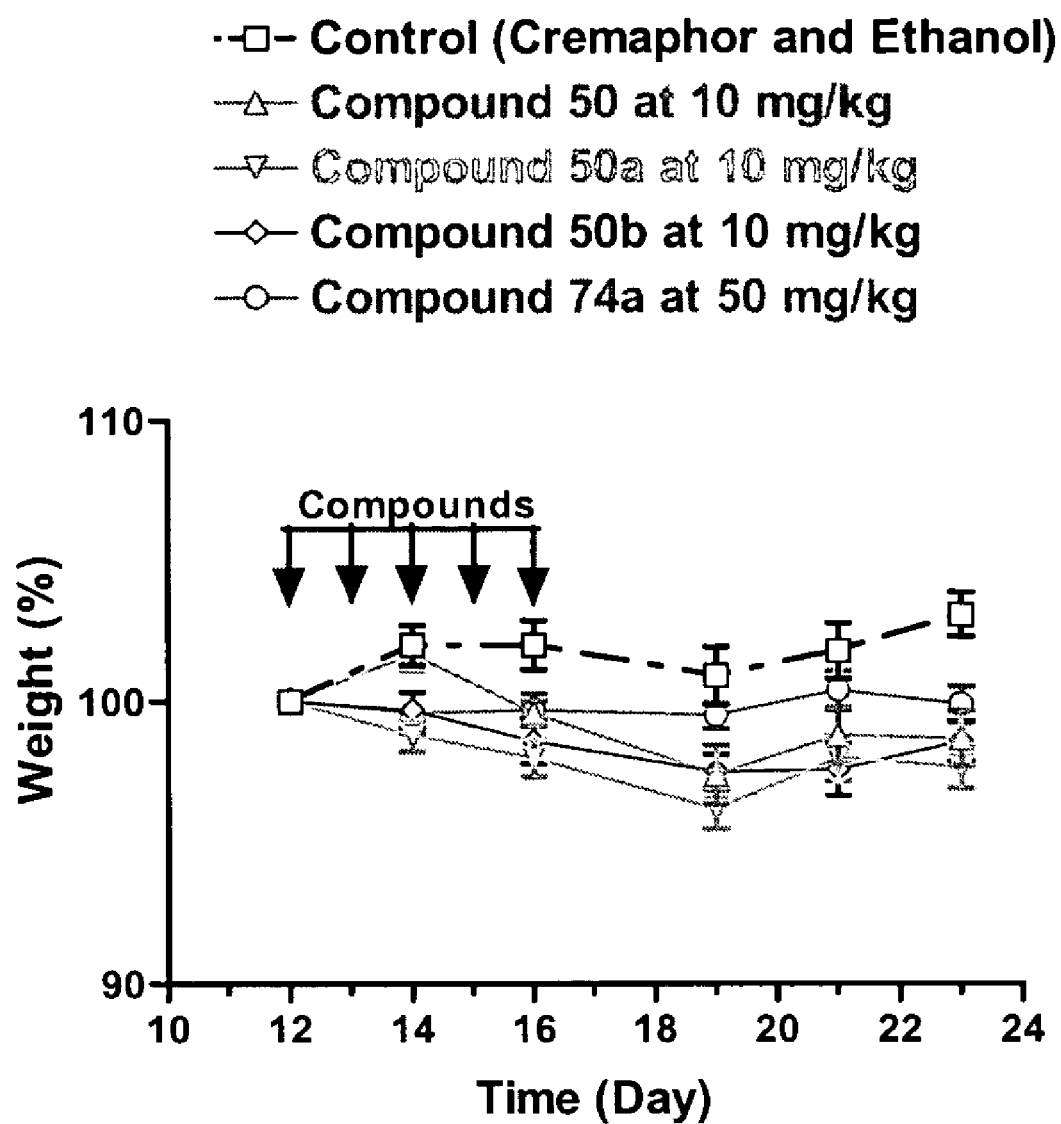
FIG. 9 shows a graph depicting the weight of mice following treatment with Compound 50, 50a, 50b or 74a. The time-points of administration of Compound 50, 50a, 50b or 74a are indicated by arrows on top of the graph.
Figure 10:
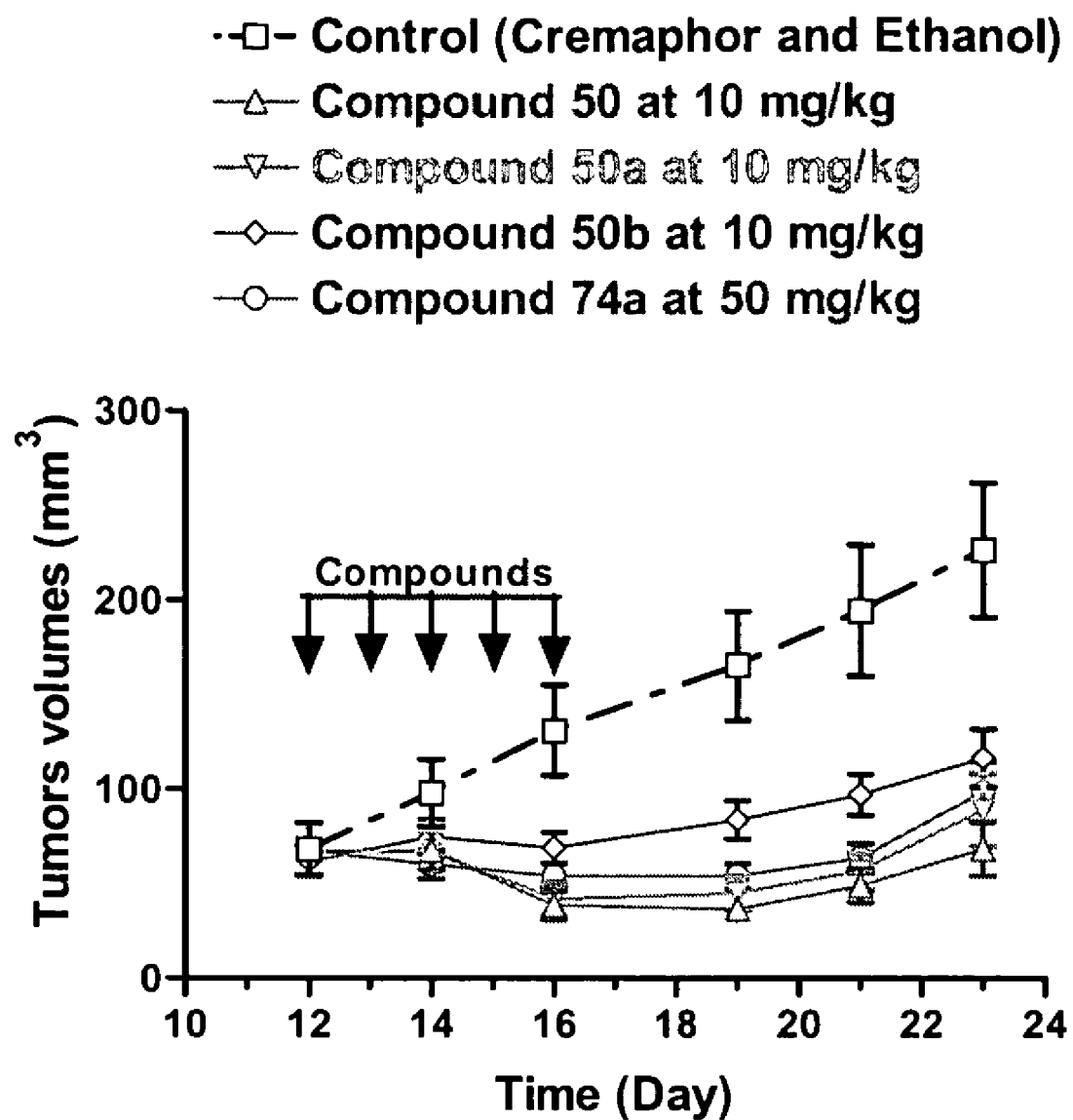
FIG. 10 shows a graph depicting the tumor size in mice following treatment with Compound 50, 50a, 50b or 74a. The time-points of administration of Compound 50, 50a, 50b or 74a are indicated by arrows on top of the graph.

The mice were weighed and the tumors measured on day 12 and every 2 to 3 days after treatment commenced. Observations continued for 23 days after initial tumor implantation. The changes in body weight and in the calculated tumor volume were plotted (FIGS. 9 and 10). Statistical analysis was performed using GraphPad Prism (GraphPad Software Inc., San Diego, Calif.). Two-way ANOVA was used to determine how the treatment affected tumor growth over time. Following the two-way ANOVA, post-tests were performed using the Benferroni method to determine the statistical difference between the mean tumor-size of the two groups being compared on every day that the tumors were measured.

As shown in FIG. 9, mice treated with Compound 50, 50a, 50b or 74a experienced a non-significant change in body weight.

As shown in FIG. 10, each of Compound 50, 50a and 50b administered i.v. at a dose of 10 mg/kg, once a day for five days resulted in a significant reduction (p<0.001) in tumor growth compared to mice treated i.v. with vehicle only. Similarly, animals treated with Compound 74a also had a significantly reduction (p<0.001) in tumor growth compared to mice treated with vehicle only.

As indicated in FIG. 10, Compound 50, 50a, 50b and 74a each significantly reduces the human colon carcinoma tumors implanted in SCID mice, an art-accepted model for human colon carcinoma cancer. Accordingly, Compound 50, 50a, 50b and 74a are useful for inhibiting the growth of a cancer cell, particularly a colon carcinoma cancer cell, and for treating or preventing cancer, particularly colon carcinoma cancer, in a patient.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which have been incorporated herein in their entirety.

What is claimed is:

1. A compound having the Formula (Ia):

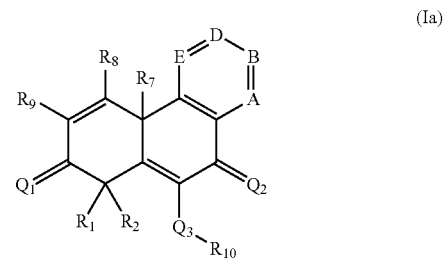

or a pharmaceutically acceptable salts thereof, wherein:

$Q_1$ and $Q_2$ are independently =O, =S, =NOR, =NR, =N—NHR, or =N—N(R)$_2$ where R is —H, —C$_1$–C$_{10}$ alkyl, or -aryl;

$Q_3$ is —O—, —S—, or —N(H)—;

$R_1$ and $R_2$ are independently —H, -halogen, -amino, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is CR$_3$; B is CR$_4$; D is CR$_5$; E is CR$_6$;

each $R_3$, $R_4$, $R_5$ and $R_6$ is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

$R_7$ is —H, —C$_1$–C$_{10}$ alkyl, or —C$_1$–C$_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)$NH_2$, —C(O)$NHR_{12}$, —C(O)N($R_{12}$)$_2$, P(O)(O$R_{13}$)$_2$, or -aryl, wherein $R_{10}$ is not P(O)(O$R_{13}$)$_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

each halogen is independently —F, —Cl, —Br or —I; and $R_{13}$ is H, $C_1$–$C_{10}$ alkyl, aryl, or benzyl;

with the proviso that the compound of Formula (Ia) is not:

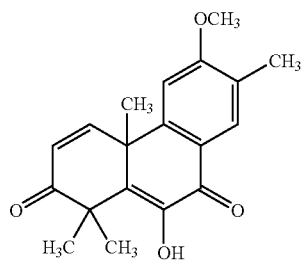

10-Hydroxy-6-methoxy-1,1,4a,7-tetramethyl-1H,4aH-phenanthrene-2,9-dione; or

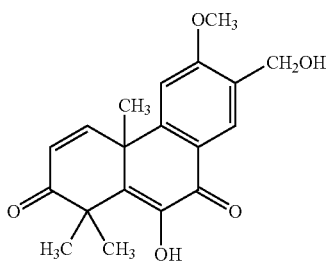

10-Hydroxy-7-hydroxymethyl-6-methoxy-1,1,4a-trimethyl-1H,4aH-phenanthrene-2,9-dione, or a pharmaceutically acceptable salt thereof; and with the further proviso that if (i) D is C—OH; (ii) $Q_1$ is =O; (iii) $Q_2$ is =O; (iv) A is CH; and (v) E is $CR_7$ then $R_4$ is not —$CH_3$.

2. A compound having the Formula (Ib):

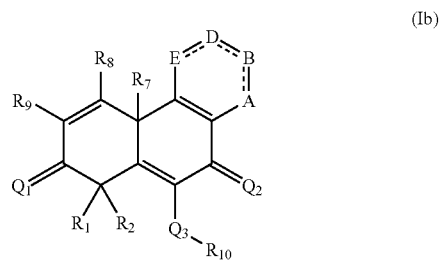

(Ib)

and pharmaceutically acceptable salts thereof, wherein:

a dashed line indicates that the bond between the atoms that are connected by the dashed line can be a single bond or a double bond;

the ring with positions A, B, D, and E is not aromatic;

$Q_1$ and $Q_2$ are independently =O, =S, =NOR, =NR, =N—NHR, or =N—N(R)$_2$ where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, =O, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)O$R_{11}$, —OC(O)$NR_{11}$, —C(O)O$R_{11}$, —C(O)$NR_{11}$, —OP(O)(O$R_{11}$)$_2$, —$SR_{11}$, —S(O)$_2NHR_{11}$, —$SOR_{11}$, —S(O)$_2R_{11}$, —NHC(O)$R_{11}$, —$NHSOR_{11}$, NHS(O)$_2R_{11}$, —OPO(O$R_{15}$)$_2$, —O-arylPO(O$R_{15}$)$_2$, or —O-alkylarylPO(O$R_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —OC(O)$R_{11}$, —C(O)$R_{11}$, —OC(O)O$R_{11}$, —OC(O)$NR_{11}$, —C(O)O$R_{11}$, —C(O)$NR_{11}$, —OP(O)(O$R_{11}$)$_2$, —$SR_{11}$, —$SOR_{11}$, —S(O)$_2R_{11}$, —S(O)$_2NHR_{11}$, —$NHSR_{11}$, —$NHSOR_{11}$, or —NHS(O)$_2R_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —C$_1$–C$_{10}$ alkyl, —C$_3$–C$_7$ cycloalkyl, —C(O)C$_1$–C$_{10}$ alkyl, —C$_1$–C$_{10}$ (oxy)alkyl, —C(O)NH$_2$, —C(O)NHR$_{12}$, —C(O)N(R$_{12}$)$_2$, P(O)(OR$_{13}$)$_2$, or -aryl, wherein $R_{10}$ is not P(O)(OR$_{13}$)$_2$ if $Q_3$ is —N(H)— or —S—;

$R_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

$R_{12}$ is C$_1$–C$_{10}$ alkyl; and each halogen is independently —F, —Cl, —Br or —I.

$R_{13}$ is H, C$_1$–C$_{10}$ alkyl, aryl, or benzyl.

3. A compound having the Formula (Ic):

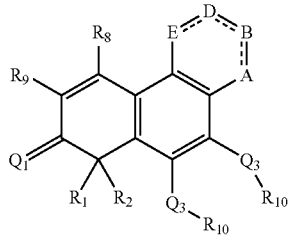

(Ic)

and pharmaceutically acceptable salts thereof, wherein:

a dashed line indicates that the bond between the atoms that are connected by the dashed line can be a single bond or a double bond;

$Q_1$ is =O, =S, =NOR, =NR, =N—NHR, or =N—N(R)$_2$ where R is —H, —C$_1$–C$_{10}$ alkyl, or -aryl;

$Q_3$ is at each occurance independently —O—, —S—, or —N(H)—;

$R_1$ and $R_2$ are independently —H, -halogen, -amino, —C$_1$–C$_{10}$ alkyl, —C$_1$–C$_{10}$ alkoxy, —C$_1$–C$_{10}$ (hydroxy)alkyl, C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is CR$_3$; B is CR$_4$; D is CR$_5$; E is CR$_6$;

each $R_3$, $R_4$, $R_5$ and $R_6$ is independently —H, =O, —OH, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein $R_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

$R_7$ is —H, —C$_1$–C$_{10}$ alkyl, or —C$_1$–C$_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is at each occurance independently —H, —C$_1$–C$_{10}$ alkyl, —C$_3$–C$_7$ cycloalkyl, —C(O)C$_1$–C$_{10}$ alkyl, —C$_1$–C$_{10}$ (oxy)alkyl, —C(O)NH$_2$, —C(O)NHR$_{12}$, —C(O)N(R$_{12}$)$_2$, P(O)(OR$_{13}$)$_2$, or -aryl, wherein $R_{10}$ is not P(O)(OR$_{13}$)$_2$ if $Q_3$ is —N(H)— or —S—;

$R_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

$R_{12}$ is C$_1$–C$_{10}$ alkyl; and each halogen is independently —F, —Cl, —Br or —I.

$R_{13}$ is H, C$_1$–C$_{10}$ alkyl, aryl, or benzyl.

4. A compound having the Formula (IIa):

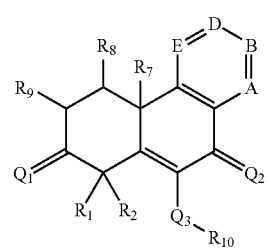

(IIa)

or a pharmaceutically acceptable salt thereof, wherein:

$Q_1$ and $Q_2$ are independently =O, =S, =NOR, =NR, =N—NHR, or =N—N(R)$_2$, where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —OC(O)$R_{11}$, —OC(O)O$R_{11}$, —OC(O)N$R_{11}$, —C(O)O$R_{11}$, —C(O)N$R_{11}$, —OP(O)(O$R_{11}$)$_2$, —S$R_{11}$, —S(O)$_2NHR_{11}$, —SO$R_{11}$, —S(O)$_2R_{11}$, —NHC(O)$R_{11}$, —NHSO$R_{11}$, NHS(O)$_2R_{11}$ —OPO(O$R_{15}$)$_2$, —O-arylPO(O$R_{15}$)$_2$, or —O-alkylarylPO(O$R_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —OC$R_{11}$, —OC(O)$R_{11}$, —C(O)$R_{11}$, —OC(O)O$R_{11}$, —OC(O)N$R_{11}$, —C(O)O$R_{11}$, —C(O)N$R_{11}$, —OP(O)(O$R_{11}$)$_2$, —S$R_{11}$, —SO$R_{11}$, —S(O)$_2R_{11}$, —S(O)$_2NHR_{11}$, —NHSO$R_{11}$, —NHSO$R_{11}$, or —NHS(O)$_2R_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)$NH_2$, —C(O)NH$R_{12}$, —C(O)N($R_{12}$)$_2$, P(O)(O$R_{13}$)$_2$, or -aryl, wherein $R_{10}$ is not P(O)(O$R_{13}$)$_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

each halogen is independently —F, —Cl, —Br or —I; and $R_{13}$ is H, $C_1$–$C_{10}$ alkyl, aryl, or benzyl;

with the proviso that (a) if (i) D is C—OH, (ii) $Q_1$ is =O, (iii) $Q_2$ is =O, (iv) A is CH, and (v) E is $CR_7$ then $R_4$ is not —CH$_3$; and (b) if (i) E is C—OH, (ii) $Q_1$ is =O, (iii) $Q_2$ is =O, (iv) $R_{10}$ is H, (v) B is $CR_4$, (vi) D is $CR_5$, (vii) $R_7$ is $CH_3$, and (viii) $Q_3$ is —O— then A is not C—OH.

5. A compound having the Formula (IIb):

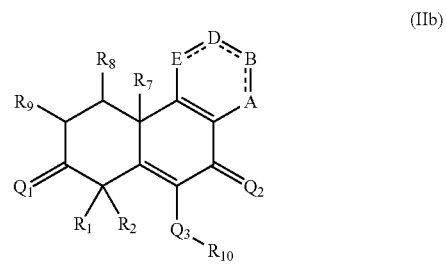

(IIb)

or a pharmaceutically acceptable salt thereof, wherein:

a dashed line indicates that the bond between the atoms that are connected by the dashed line can be a single bond or a double bond;

the ring with positions A, B, D, and E is not aromatic;

$Q_1$ and $Q_2$ are independently =O, =S, =NOR, =NR, =N—NHR, or =N—N(R)$_2$, where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, =O, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)O$R_{11}$, —OC(O)N$R_{11}$, —C(O)O$R_{11}$, —C(O)N$R_{11}$, —OP(O)(O$R_{11}$)$_2$, —S$R_{11}$, —S(O)$_2NHR_{11}$, —SO$R_{11}$, —S(O)$_2R_{11}$, —NHC(O)$R_{11}$, —NHSO$R_{11}$, NHS(O)$_2R_{11}$, —OPO(O$R_{15}$)$_2$, —O-arylPO(O$R_{15}$)$_2$, or —O-alkylarylPO(O$R_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)

NH₂, —S(O)₂NH₂, —C₁–C₁₀ (oxy)alkyl, —C₁–C₁₀ alkyl, —C₁–C₁₀ alkoxy, —C₁–C₁₀ (hydroxy)alkyl, —C₁–C₁₀ (amino)alkyl, —C₁–C₁₀ (halo)alkyl, —C₂–C₁₀ alkenyl, —C₂–C₁₀ alkynyl, —(C₃–C₇) cycloalkyl, -aryl, —C₁–C₁₀ (aryl)alkyl, three- to seven-membered non-aromatic heterocycle, five- to seven-membered aromatic heterocycle, —CH₂OR₁₁, —OCR₁₁, —OC(O)R₁₁, —C(O)R₁₁, —OC(O)OR₁₁, —OC(O)NR₁₁, —C(O)OR₁₁, —C(O)NR₁₁, —OP(O)(OR₁₁)₂, —SR₁₁, —SOR₁₁, —S(O)₂R₁₁, —S(O)₂NHR₁₁, —NHSR₁₁, —NHSOR₁₁, or —NHS(O)₂R₁₁;

R₈ is also —S(CH₂)ₙamino acid, —S(CH₂)ₙpeptide, wherein n=0 to 4, wherein the amino acid is connected to the compound through its alpha carbon atom, and wherein the peptide is connected to the compound through the alpha carbon atom of one of its amino acids;

R₁₀ is —H, —C₁–C₁₀ alkyl, —C₃–C₇ cycloalkyl, —C(O)C₁–C₁₀ alkyl, —C₁–C₁₀ (oxy)alkyl, —C(O)NH₂, —C(O)NHR₁₂, —C(O)N(R₁₂)₂, P(O)(OR₁₃)₂, or -aryl, wherein R₁₀ is not P(O)(OR₁₃)₂ if Q₃ is —N(H)— or —S—;

R₁₁ is —H, —C₁–C₁₀ alkyl, —(C₃–C₇) cycloalkyl, —C₁–C₁₀ (halo)alkyl, -aryl, —C₂–C₁₀ alkenyl, —C₂–C₁₀ alkynyl, —C₁–C₁₀ (aryl)alkyl, —C₂–C₁₀ (aryl)alkenyl, —C₂–C₁₀ (aryl)alkynyl, —C₁–C₁₀ (hydroxy)alkyl, —C₁–C₁₀ alkoxy, —C₁–C₁₀ (amino)alkyl, a —(C₃–C₇) cycloalkyl unsubstituted or substituted with one or more —C₁–C₁₀ alkyl,
a three- to seven-membered non-aromatic heterocycle unsubstituted or substituted with one or more —C₁–C₁₀ alkyl, or
a three- to seven-membered aromatic heterocycle unsubstituted or substituted with one or more —C₁–C₁₀ alkyl, —C₂–C₁₀ alkenyl, or —C₂–C₁₀ alkynyl;

R₁₂ is C₁–C₁₀ alkyl;
each halogen is independently —F, —Cl, —Br or —I; and
R₁₃ is H, C₁–C₁₀ alkyl, aryl, or benzyl.

6. A compound having the Formula (IIc):

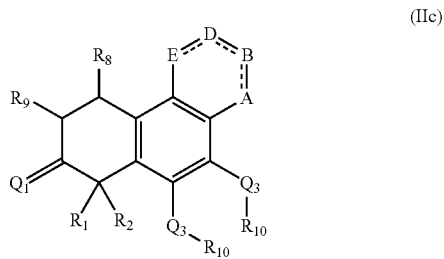

(IIc)

or a pharmaceutically acceptable salt thereof, wherein:
a dashed line indicates that the bond between the atoms that are connected by the dashed line can be a single bond or a double bond;
Q₁ is =O, =S, =NOR, =NR, =N—NHR, or =N—N(R)₂, where R is —H, —C₁–C₁₀ alkyl, or -aryl;
Q₃ is at each occurance independently —O—, —S—, or —N(H)—;
R₁ and R₂ are independently —H, -halogen, -amino, —C₁–C₁₀ alkyl, —C₁–C₁₀ alkoxy, —C₁–C₁₀ (hydroxy)alkyl, —C₁–C₁₀ (amino)alkyl, —C₁–C₁₀ (halo)alkyl, —C₂–C₁₀ alkenyl, —C₂–C₁₀ alkynyl, (C₃–C₇) cycloalkyl, -aryl, C₁–C₁₀ (aryl)alkyl, or three- to seven-membered non-aromatic heterocycle, or R₁, R₂ and the carbon atom to which they are both attached are taken together to form a (C₃–C₇) cycloalkyl group or a three- to seven-membered non-aromatic heterocycle;

A is CR₃; B is CR₄; D is CR₅; E is CR₆;
each R₃, R₄, R₅ and R₆ is independently —H, =O, —OH, -halogen, —CN, —NH₂, —NO₂, —COOH, —C(O)NH₂, —SH, —S(O)NH₂, —S(O)₂NH₂, —C₁–C₁₀ (oxy)alkyl, —C₁–C₁₀ alkyl, —C₁–C₁₀ alkoxy, —C₁–C₁₀ (hydroxy)alkyl, —C₁–C₁₀ (amino)alkyl, —C₁–C₁₀ (halo)alkyl, —C₂–C₁₀ alkenyl, —C₂–C₁₀ alkynyl, —(C₃–C₇) cycloalkyl, -aryl, —C₁–C₁₀ (aryl)alkyl, three- to seven-membered non-aromatic heterocycle, five- to seven-membered aromatic heterocycle, —CH₂OR₁₁, —OCH₂OR₁₁, —OC(O)R₁₁, —C(O)R₁₁, —OC(O)OR₁₁, —OC(O)NR₁₁, —C(O)OR₁₁, —C(O)NR₁₁, —OP(O)(OR₁₁)₂, —SR₁₁, —S(O)₂NHR₁₁, —SOR₁₁, —S(O)₂R₁₁, —NHC(O)R₁₁, —NHSOR₁₁, NHS(O)₂R₁₁, —OPO(OR₁₅)₂, —O-arylPO(OR₁₅)₂, or —O-alkylarylPO(OR₁₅)₂ wherein R₁₅ is H, —C₁–C₁₀ alkyl, C₇–C₁₂arylalkyl, C₁–C₁₀ aminoalkyl, C₁–C₁₀ haloalkyl, C₁–C₁₀ hydroxyalkyl, C₁–C₁₀ alkoxy;

R₇ is —H, —C₁–C₁₀ alkyl, or —C₁–C₁₀ alkoxy;
R₈ and R₉ are each independently —H, -halogen, —CN, —NH₂, —NO₂, —COOH, —C(O)NH₂, —SH, —S(O)NH₂, —S(O)₂NH₂, —C₁–C₁₀ (oxy)alkyl, —C₁–C₁₀ alkyl, —C₁–C₁₀ alkoxy, —C₁–C₁₀ (hydroxy)alkyl, —C₁–C₁₀ (amino)alkyl, —C₁–C₁₀ (halo)alkyl, —C₂–C₁₀ alkenyl, —C₂–C₁₀ alkynyl, —(C₃–C₇) cycloalkyl, -aryl, —C₁–C₁₀ (aryl)alkyl, three- to seven-membered non-aromatic heterocycle, five- to seven-membered aromatic heterocycle, —CH₂OR₁₁, —OCR₁₁, —OC(O)R₁₁, —C(O)R₁₁, —OC(O)OR₁₁, —OC(O)NR₁₁, —C(O)OR₁₁, —C(O)NR₁₁, —OP(O)(OR₁₁)₂, —SR₁₁, —SOR₁₁, —S(O)₂R₁₁, —S(O)₂NHR₁₁, —NHSR₁₁, —NHSOR₁₁, or —NHS(O)₂R₁₁;

R₈ is also —S(CH₂)ₙamino acid, —S(CH₂)ₙpeptide, wherein n=0 to 4, wherein the amino acid is connected to the compound through its alpha carbon atom, and wherein the peptide is connected to the compound through the alpha carbon atom of one of its amino acids;

R₁₀ is at each occurance independently —H, —C₁–C₁₀ alkyl, —C₃–C₇ cycloalkyl, —C(O)C₁–C₁₀ alkyl, —C₁–C₁₀ (oxy)alkyl, —C(O)NH₂, —C(O)NHR₁₂, —C(O)N(R₁₂)₂, P(O)(OR₁₃)₂, or -aryl, wherein R₁₀ is not P(O)(OR₁₃)₂ if Q₃ is —N(H)— or —S—;

R₁₁ is —H, —C₁–C₁₀ alkyl, —(C₃–C₇) cycloalkyl, —C₁–C₁₀ (halo)alkyl, -aryl, —C₂–C₁₀ alkenyl, —C₂–C₁₀ alkynyl, —C₁–C₁₀ (aryl)alkyl, —C₂–C₁₀ (aryl)alkenyl, —C₂–C₁₀ (aryl)alkynyl, —C₁–C₁₀ (hydroxy)alkyl, —C₁–C₁₀ alkoxy, —C₁–C₁₀ (amino)alkyl, a —(C₃–C₇) cycloalkyl unsubstituted or substituted with one or more —C₁–C₁₀ alkyl,
a three- to seven-membered non-aromatic heterocycle unsubstituted or substituted with one or more —C₁–C₁₀ alkyl, or
a three- to seven-membered aromatic heterocycle unsubstituted or substituted with one or more —C₁–C₁₀ alkyl, —C₂–C₁₀ alkenyl, or —C₂–C₁₀ alkynyl;

R₁₂ is C₁–C₁₀ alkyl;
each halogen is independently —F, —Cl, —Br or —I; and
R₁₃ is H, C₁–C₁₀ alkyl, aryl, or benzyl.

7. A compound having the Formula (IIIa):

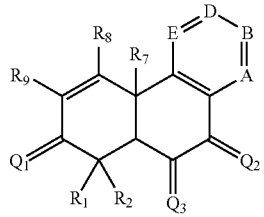

(IIIa)

or a pharmaceutically acceptable salt thereof, wherein:

$Q_1$, $Q_2$ and $Q_3$ are independently =O, =S, =NOR, =NR, =N—NHR, or =N—N(R)$_2$, where R is —H, —C$_1$–C$_{10}$ alkyl, or -aryl;

$R_1$ and $R_2$ are independently —H, -halogen, -amino, —C$_1$–C$_{10}$ alkyl, —C$_1$–C$_{10}$ alkoxy, —C$_1$–C$_{10}$ (hydroxy) alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is CR$_3$; B is CR$_4$; D is CR$_5$; E is CR$_6$;

each $R_3$, $R_4$, $R_5$ and $R_6$ is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino) alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein $R_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

$R_7$ is —H, —C$_1$–C$_{10}$ alkyl, or —C$_1$–C$_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

$R_{12}$ is C$_1$–C$_{10}$ alkyl; and each halogen is independently —F, —Cl, —Br or —I.

8. A compound having the Formula (IIIb):

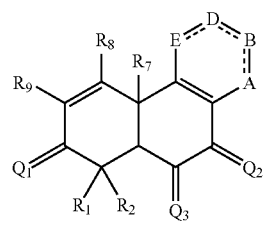

(IIIb)

or a pharmaceutically acceptable salt thereof, wherein:

a dashed line indicates that the bond between the atoms that are connected by the dashed line can be a single bond or a double bond;

the ring with positions A, B, D, and E is not aromatic;

$Q_1$, $Q_2$ and $Q_3$ are independently =O, =S, =NOR, =NR, =N—NHR, or =N—N(R)$_2$, where R is —H, —C$_1$–C$_{10}$ alkyl, or -aryl;

$R_1$ and $R_2$ are independently —H, -halogen, -amino, —C$_1$–C$_{10}$ alkyl, —C$_1$–C$_{10}$ alkoxy, —C$_1$–C$_{10}$ (hydroxy) alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is CR$_3$; B is CR$_4$; D is CR$_5$; E is CR$_6$;

each $R_3$, $R_4$, $R_5$ and $R_6$ is independently —H, —OH, =O, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino) alkyl, C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl) alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein $R_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

$R_7$ is —H, —C$_1$–C$_{10}$ alkyl, or —C$_1$–C$_{10}$ alkoxy;

$R_8$ and $R_9$ are each independently —H, -halogen, —CN, —NH$_2$, —NO$_2$, —COOH, —C(O)NH$_2$, —SH, —S(O)

—$NH_2$, —$S(O)_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —$(C_3$–$C_7)$ cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —$OC(O)R_{11}$, —$C(O)R_{11}$, —$OC(O)OR_{11}$, —$OC(O)NR_{11}$, —$C(O)OR_{11}$, —$C(O)NR_{11}$, —$OP(O)(OR_{11})_2$, —$SR_{11}$, —$SOR_{11}$, —$S(O)_2R_{11}$, —$S(O)_2NHR_{11}$, —$NHSR_{11}$, —$NHSOR_{11}$, or —$NHS(O)_2R_{11}$;

$R_8$ is also —$S(CH_2)_n$amino acid, —$S(CH_2)_n$peptide, wherein n=0 to 4, wherein the amino acid is connected to the compound through its alpha carbon atom, and wherein the peptide is connected to the compound through the alpha carbon atom of one of its amino acids;

$R_{11}$ is —H, —$C_1$–$C_{10}$ alkyl, —$(C_3$–$C_7)$ cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$(hydroxy)alkyl, —$C_1$–$C_{10}$ alkoxy, —$C_1$–$C_{10}$ (amino)alkyl, a —$(C_3$–$C_7)$ cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl; and each halogen is independently —F, —Cl, —Br or —I.

9. A compound having the Formula (IVa):

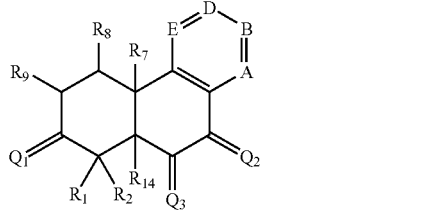

(IVa)

or a pharmaceutically acceptable salt thereof, wherein:

$Q_1$, $Q_2$ and $Q_3$ are independently =O, =S, =NOR, =NR, =N—NHR, or =N—N(R)$_2$, where R is —H, —$C_1$–$C_{10}$ alkyl, or -aryl;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, $(C_3$–$C_7)$ cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a $(C_3$–$C_7)$ cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, —OH, -halogen, —CN, —$NH_2$, —$NO_2$, —COOH, —$C(O)NH_2$, —SH, —$S(O)NH_2$, —$S(O)_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —$(C_3$–$C_7)$ cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —$OC(O)R_{11}$, —$C(O)R_{11}$, —$OC(O)OR_{11}$, —$OC(O)NR_{11}$, —$C(O)OR_{11}$, —$C(O)NR_{11}$, —$OP(O)(OR_{11})_2$, —$SR_{11}$, —$S(O)_2NHR_{11}$, —$SOR_{11}$, —$S(O)_2R_{11}$, —$NHC(O)R_{11}$, —$NHSOR_{11}$, $NHS(O)_2R_{11}$, —$OPO(OR_{15})_2$, —O-arylPO(OR$_{15})_2$, or —O-alkylarylPO(OR$_{15})_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —$C(O)NH_2$, —SH, —$S(O)NH_2$, —$S(O)_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —$(C_3$–$C_7)$ cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —$OC(O)R_{11}$, —$C(O)R_{11}$, —$OC(O)OR_{11}$, —$OC(O)NR_{11}$, —$C(O)OR_{11}$, —$C(O)NR_{11}$, —$OP(O)(OR_{11})_2$, —$SR_{11}$, —$SOR_{11}$, —$S(O)_2R_{11}$, —$S(O)_2NHR_{11}$, —$NHSR_{11}$, —$NHSOR_{11}$, or —$NHS(O)_2R_{11}$;

$R_8$ is also —$S(CH_2)_n$amino acid, —$S(CH_2)_n$peptide, wherein n=0 to 4, wherein the amino acid is connected to the compound through its alpha carbon atom, and wherein the peptide is connected to the compound through the alpha carbon atom of one of its amino acids;

$R_{11}$ is —H, —$C_1$–$C_{10}$ alkyl, —$(C_3$–$C_7)$ cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —$(C_3$–$C_7)$ cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

$R_{14}$ is —H, —OH, or halogen; and each halogen is independently —F, —Cl, —Br or —I.

10. A compound having the Formula (IVb):

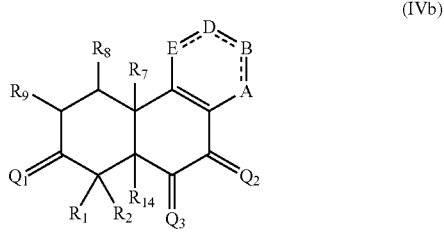

(IVb)

or a pharmaceutically acceptable salt thereof, wherein:

a dashed line indicates that the bond between the atoms that are connected by the dashed line can be a single bond or a double bond;

the ring with positions A, B, D, and E is not aromatic;

$Q_1$, $Q_2$ and $Q_3$ are independently =O, =S, =NOR, =NR, =N—NHR, or =N—N(R)$_2$, where R is —H, —C$_1$–C$_{10}$ alkyl, or -aryl;

$R_1$ and $R_2$ are independently —H, -halogen, -amino, —C$_1$–C$_{10}$ alkyl, —C$_1$–C$_{10}$ alkoxy, —C$_1$–C$_{10}$ (hydroxy) alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is CR$_3$; B is CR$_4$; D is CR$_5$; E is CR$_6$;

each $R_3$, $R_4$, $R_5$ and $R_6$ is independently —H, —OH, =O, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, C$_1$–C$_{10}$ (amino) alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein $R_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

$R_7$ is —H, —C$_1$–C$_{10}$ alkyl, or —C$_1$–C$_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{11}$, is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

$R_{12}$ is C$_1$–C$_{10}$ alkyl;

$R_{14}$ is —H, —OH, or halogen; and each halogen is independently —F, —Cl, —Br or —I.

11. A compound having the Formula (Va):

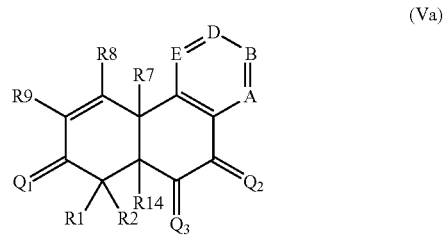

(Va)

or a pharmaceutically acceptable salt thereof, wherein:

$Q_1$, $Q_2$ and $Q_3$ are independently =O, =S, =NR, =NOR, =N—NHR, or =N—N(R)$_2$ where R is —H, —C$_1$–C$_{10}$ alkyl, or -aryl;

$R_1$ and $R_2$ are independently —H, -halogen, -amino, —C$_1$–C$_{10}$ alkyl, —C$_1$–C$_{10}$ alkoxy, —C$_1$–C$_{10}$ (hydroxy) alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is CR$_3$; B is CR$_4$; D is CR$_5$; E is CR$_6$;

each $R_3$, $R_4$, $R_5$ and $R_6$ is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino) alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein $R_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

$R_7$ is —H, —C$_1$–C$_{10}$ alkyl, or —C$_1$–C$_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R₁₁ is —H, —C₁–C₁₀ alkyl, —(C₃–C₇) cycloalkyl, —C₁–C₁₀ (halo)alkyl, -aryl, —C₂–C₁₀ alkenyl, —C₂–C₁₀ alkynyl, —C₁–C₁₀ (aryl)alkyl, —C₂–C₁₀ (aryl)alkenyl, —C₂–C₁₀ (aryl)alkynyl, —C₁–C₁₀ (hydroxy)alkyl, —C₁–C₁₀ alkoxy, —C₁–C₁₀ (amino)alkyl, a —(C₃–C₇) cycloalkyl unsubstituted or substituted with one or more —C₁–C₁₀ alkyl, a three- to seven-membered non-aromatic heterocycle unsubstituted or substituted with one or more —C₁–C₁₀ alkyl, or a three- to seven-membered aromatic heterocycle unsubstituted or substituted with one or more —C₁–C₁₀ alkyl, —C₂–C₁₀ alkenyl, or —C₂–C₁₀ alkynyl;

R₁₂ is C₁–C₁₀ alkyl;

R₁₄ is —H, —OH, or halogen; and each halogen is independently —F, —Cl, —Br or —I.

12. A compound having the Formula (Vb):

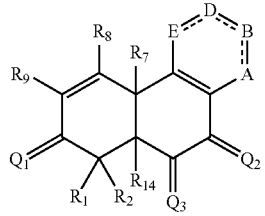

(Vb)

or a pharmaceutically acceptable salt thereof, wherein:

a dashed line indicates that the bond between the atoms that are connected by the dashed line can be a single bond or a double bond;

the ring with positions A, B, D, and E is not aromatic;

Q₁, Q₂ and Q₃ are independently =O, =S, =NR, =NOR, =N—NHR, or =N—N(R)₂ where R is —H, —C₁–C₁₀ alkyl, or -aryl;

R₁ and R₂ are independently —H, -halogen, -amino, —C₁–C₁₀ alkyl, —C₁–C₁₀ alkoxy, —C₁–C₁₀ (hydroxy)alkyl, —C₁–C₁₀ (amino)alkyl, —C₁–C₁₀ (halo)alkyl, —C₂–C₁₀ alkenyl, —C₂–C₁₀ alkynyl, (C₃–C₇) cycloalkyl, -aryl, C₁–C₁₀ (aryl)alkyl, or three- to seven-membered non-aromatic heterocycle, or R₁, R₂ and the carbon atom to which they are both attached are taken together to form a (C₃–C₇) cycloalkyl group or a three- to seven-membered non-aromatic heterocycle;

A is CR₃; B is CR₄; D is CR₅; E is CR₆;

each R₃, R₄, R₅ and R₆ is independently —H, —OH, =O, -halogen, —CN, —NH₂, —NO₂, —COOH, —C(O)NH₂, —SH, —S(O)NH₂, —S(O)₂NH₂, —C₁–C₁₀ (oxy)alkyl, —C₁–C₁₀ alkyl, —C₁–C₁₀ alkoxy, —C₁–C₁₀ (hydroxy)alkyl, —C₁–C₁₀ (amino)alkyl, —C₁–C₁₀ (halo)alkyl, —C₂–C₁₀ alkenyl, —C₂–C₁₀ alkynyl, —(C₃–C₇) cycloalkyl, -aryl, —C₁–C₁₀ (aryl)alkyl, three- to seven-membered non-aromatic heterocycle, five- to seven-membered aromatic heterocycle, —CH₂OR₁₁, —OCH₂OR₁₁, —OC(O)R₁₁, —C(O)R₁₁, —OC(O)OR₁₁, —OC(O)NR₁₁, —C(O)OR₁₁, —C(O)NR₁₁, —OP(O)(OR₁₁)₂, —SR₁₁, —S(O)₂R₁₁, —SOR₁₁, —S(O)₂R₁₁, —NHC(O)R₁₁, —NHSOR₁₁, NHS(O)₂R₁₁, —OPO(OR₁₅)₂, —O-arylPO(OR₁₅)₂, or —O-alkylarylPO(OR₁₅)₂ wherein R₁₅ is H, —C₁–C₁₀ alkyl, C₇–C₁₂ arylalkyl, C₁–C₁₀ aminoalkyl, C₁–C₁₀ haloalkyl, C₁–C₁₀ hydroxyalkyl, C₁–C₁₀ alkoxy;

R₇ is —H, —C₁–C₁₀ alkyl, or —C₁–C₁₀ alkoxy;

R₈ and R₉ are each independently —H, -halogen, —CN, —NH₂, —NO₂, —COOH, —C(O)NH₂, —SH, —S(O)NH₂, —S(O)₂NH₂, —C₁–C₁₀(oxy)alkyl, —C₁–C₁₀ alkyl, —C₁–C₁₀ alkoxy, —C₁–C₁₀ (hydroxy)alkyl, —C₁–C₁₀ (amino)alkyl, —C₁–C₁₀ (halo)alkyl, —C₂–C₁₀ alkenyl, —C₂–C₁₀ alkynyl, —(C₃–C₇) cycloalkyl, -aryl, —C₁–C₁₀ (aryl)alkyl, three- to seven-membered non-aromatic heterocycle, five- to seven-membered aromatic heterocycle, —CH₂OR₁₁, —OCR₁₁, —OC(O)R₁₁, —C(O)R₁₁, —OC(O)OR₁₁, —OC(O)NR₁₁, —C(O)OR₁₁, —C(O)NR₁₁, —OP(O)(OR₁₁)₂, —SR₁₁, —SOR₁₁, —S(O)₂R₁₁, —S(O)₂NHR₁₁, —NHSR₁₁, —NHSOR₁₁, or —NHS(O)₂R₁₁;

R₈ is also —S(CH₂)ₙamino acid, —S(CH₂)ₙpeptide, wherein n=0 to 4, wherein the amino acid is connected to the compound through its alpha carbon atom, and wherein the peptide is connected to the compound through the alpha carbon atom of one of its amino acids;

R₁₁ is —H, —C₁–C₁₀ alkyl, —(C₃–C₇) cycloalkyl, —C₁–C₁₀ (halo)alkyl, -aryl, —C₂–C₁₀ alkenyl, —C₂–C₁₀ alkynyl, —C₁–C₁₀ (aryl)alkyl, —C₂–C₁₀ (aryl)alkenyl, —C₂–C₁₀ (aryl)alkynyl, —C₁–C₁₀ (hydroxy)alkyl, —C₁–C₁₀ alkoxy, —C₁–C₁₀ (amino)alkyl, a —(C₃–C₇) cycloalkyl unsubstituted or substituted with one or more —C₁–C₁₀ alkyl, a three- to seven-membered non-aromatic heterocycle unsubstituted or substituted with one or more —C₁–C₁₀ alkyl, or a three- to seven-membered aromatic heterocycle unsubstituted or substituted with one or more —C₁–C₁₀ alkyl, —C₂–C₁₀ alkenyl, or —C₂–C₁₀ alkynyl;

R₁₂ is C₁–C₁₀ alkyl;

R₁₄ is —H, —OH, or halogen; and each halogen is independently —F, —Cl, —Br or —I.

13. A compound having the Formula (VIa):

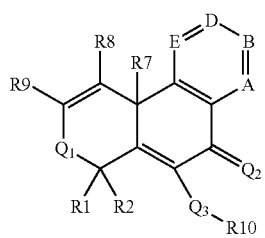

(VIa)

or a pharmaceutically acceptable salt thereof, wherein:

Q₁ is CHOH, CH2, CHOR, where R is C₁–C₁₀ alkyl, aryl, —CH₂OR₁₁, —C(O)R₁₁, —C(O)OR₁₁, —C(O)OR₁₁, —C(O)NR₁₁, —P(O)(OR₁₁)2

Q₂ is =O, =S, =NR, =NOR, =N—NHR, or =N—N(R)₂ where R is —H, —C₁–C₁₀ alkyl, or -aryl;

Q₃ is —O—, —S—, or —N(H)—;

R₁ and R₂ are independently —H, -halogen, -amino, —C₁–C₁₀ alkyl, —C₁–C₁₀ alkoxy, —C₁–C₁₀ (hydroxy)alkyl, —C₁–C₁₀ (amino)alkyl, —C₁–C₁₀ (halo)alkyl, —C₂–C₁₀ alkenyl, —C₂–C₁₀ alkynyl, (C₃–C₇) cycloalkyl, -aryl, C₁–C₁₀ (aryl)alkyl, or three- to seven-membered non-aromatic heterocycle, or R₁, R₂ and the carbon atom to which they are both attached are taken together to form a (C₃–C₇) cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)$(OR_{11})_2$, —$SR_{11}$, —S(O)$_2NHR_{11}$, —$SOR_{11}$, —S(O)$_2R_{11}$, —NHC(O)$R_{11}$, —$NHSOR_{11}$, $NHS(O)_2R_{11}$, —$OPO(OR_{15})_2$, —O-arylPO$(OR_{15})_2$, or —O-alkylarylPO$(OR_{15})_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)$(OR_{11})_2$, —$SR_{11}$, —$SOR_{11}$, —S(O)$_2R_{11}$, —S(O)$_2NHR_{11}$, —$NHSR_{11}$, —$NHSOR_{11}$, or —$NHS(O)_2R_{11}$;

$R_8$ is also —$S(CH_2)_n$amino acid, —$S(CH_2)_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)$NH_2$, —C(O)$NHR_{12}$, —C(O)$N(R_{12})_2$, P(O)$(OR_{13})_2$, or -aryl, wherein $R_{10}$ is not P(O)$(OR_{13})_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$(hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

$R_{13}$ is H, $C_1$–$C_{10}$ alkyl, aryl, or benzyl; and each halogen is independently —F, —Cl, —Br or —I.

14. A compound having the Formula (VIb):

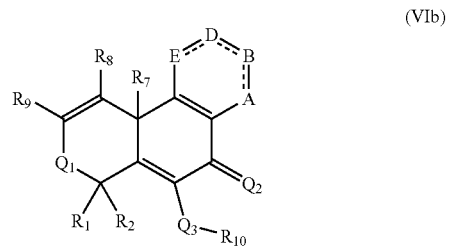

(VIb)

or a pharmaceutically acceptable salt thereof, wherein:
a dashed line indicates that the bond between the atoms that are connected by the dashed line can be a single bond or a double bond;

the ring with positions A, B, D, and E is not aromatic;

$Q_1$ is CHOH, CH2, CHOR, where R is $C_1$–$C_{10}$ alkyl, aryl, —$CH_2OR_{11}$, —C(O)$R_{11}$, —C(O)$OR_{11}$, —C(O)$OR_{11}$, —C(O)$NR_{11}$, —P(O)$(OR_{11})_2$ $Q_2$ is =O, =S, =NR, =NOR, =N—NHR, or =N—N$(R)_2$ where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, —OH, =O, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)$(OR_{11})_2$, —$SR_{11}$, —S(O)$_2NHR_{11}$, —$SOR_{11}$, —S(O)$_2R_{11}$, —NHC(O)$R_{11}$, —$NHSOR_{11}$, $NHS(O)_2R_{11}$, —$OPO(OR_{15})_2$, —O-arylPO$(OR_{15})_2$, or —O-alkylarylPO$(OR_{15})_2$ wherein $R_{15}$ is H, —$C_1$–$C_{10}$ alkyl, $C_7$–$C_{12}$arylalkyl, $C_1$–$C_{10}$ aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCR_{11}$, —OC(O)$R_{11}$, —C(O)$R_{11}$, —OC(O)$OR_{11}$, —OC(O)$NR_{11}$, —C(O)$OR_{11}$, —C(O)$NR_{11}$, —OP(O)$(OR_{11})_2$, —$SR_{11}$, —$SOR_{11}$, —S(O)$_2R_{11}$, —S(O)$_2NHR_{11}$, —$NHSR_{11}$, —$NHSOR_{11}$, or —$NHS(O)_2R_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —C$_1$–C$_{10}$ alkyl, —C$_3$–C$_7$ cycloalkyl, —C(O)C$_1$–C$_{10}$ alkyl, —C$_1$–C$_{10}$ (oxy)alkyl, —C(O)NH$_2$, —C(O)NHR$_{12}$, —C(O)N(R$_{12}$)$_2$, P(O)(OR$_{13}$)$_2$, or -aryl, wherein $R_{10}$ is not P(O)(OR$_{13}$)$_2$ if Q$_3$ is —N(H)— or —S—;

$R_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

$R_{12}$ is C$_1$–C$_{10}$ alkyl;

$R_{13}$ is H, C$_1$–C$_{10}$ alkyl, aryl, or benzyl; and each halogen is independently —F, —Cl, —Br or —I.

15. A compound having the Formula (VIIa):

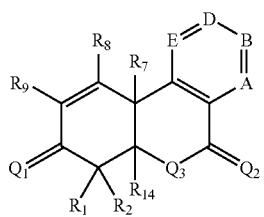

(VIIa)

or a pharmaceutically acceptable salt thereof; wherein

Q$_1$ and Q$_2$ are independently =O, =S, =NR, =NOR, =N—NHR, or =N—N(R)$_2$ where R is —H, —C$_1$–C$_{10}$ alkyl, or -aryl;

Q$_3$ is CHOH, CH2, CHOR where R is C$_1$–C$_{10}$ alkyl, aryl, —CH$_2$OR$_{11}$, —C(O)R$_{11}$, —C(O)OR$_{11}$, —C(O)OR$_{11}$, —C(O)NR$_{11}$, or —P(O)(OR$_{11}$)$_2$ $R_1$ and $R_2$ are independently —H, -halogen, -amino, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is CR$_3$; B is CR$_4$; D is CR$_5$; E is CR$_6$;

each $R_3$, $R_4$, $R_5$ and Rr is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein $R_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

$R_7$ is —H, —C$_1$–C$_{10}$ alkyl, or —C$_1$–C$_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

$R_{12}$ is C$_1$–C$_{10}$ alkyl;

$R_{14}$ is —H, —OH, or halogen; and each halogen is independently —F, —Cl, —Br or —I;

with the proviso that (a) if (i) D is C—OH, (ii) Q$_1$ is =O, (iii) Q$_2$ is =O, (iv) A is CH, and (v) E is CR$_7$ then R$_4$ is not —CH$_3$; and (b) if (i) B is C—CH$_3$, (ii) Q$_1$ is =O, (iii) Q$_2$ is =O, (iv) R$_1$ is CH$_3$, (v) R$_2$ is CH$_3$, (vi) R$_7$ is methyl, (vii) D is CH, and (viii) E is CH then R$_3$ is not ethyl.

16. A compound having the Formula (VIIb):

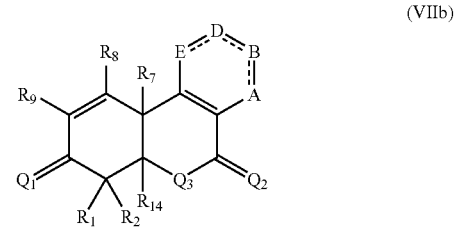

(VIIb)

or pharmaceutically acceptable salts thereof, wherein, a dashed line indicates that the bond between the atoms that are connected by the dashed line can be a single bond or a double bond;

the ring with positions A, B, D, and E is not aromatic;

$Q_1$ and $Q_2$ are independently =O, =S, =NR, =NOR, =N—NHR, or =N—N(R)$_2$ where R is —H, —C$_1$–C$_{10}$ alkyl, or -aryl;

$Q_3$ is CHOH, CH2, CHOR where R is C$_1$–C$_{10}$ alkyl, aryl, —CH$_2$OR$_{11}$, —C(O)R$_{11}$, —C(O)OR$_{11}$, —C(O)OR$_{11}$, —C(O)NR$_{11}$, or —P(O)(OR$_{11}$)$_2$ $R_1$ and $R_2$ are independently —H, -halogen, -amino, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, (C$_3$–C$_7$) cycloalkyl, -aryl, C$_1$–C$_{10}$ (aryl)alkyl, or three- to seven-membered non-aromatic heterocycle, or $R_1$, $R_2$ and the carbon atom to which they are both attached are taken together to form a (C$_3$–C$_7$) cycloalkyl group or a three- to seven-membered non-aromatic heterocycle;

A is CR$_3$; B is CR$_4$; D is CR$_5$; E is CR$_6$;

each $R_3$, $R_4$, $R_5$ and $R_6$ is independently —H, —OH, =O, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

$R_7$ is —H, —C$_1$–C$_{10}$ alkyl, or —C$_1$–C$_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

$R_{12}$ is C$_1$–C$_{10}$ alkyl;

$R_{14}$ is —H, —OH, or halogen; and each halogen is independently —F, —Cl, —Br or —I.

17. The compound of claim 1, wherein the compound has the structure:

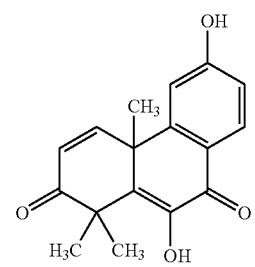

or a pharmaceutically acceptable salt thereof.

18. The compound of claim 4, wherein the compound has the structure:

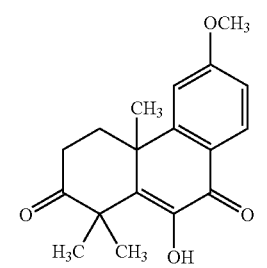

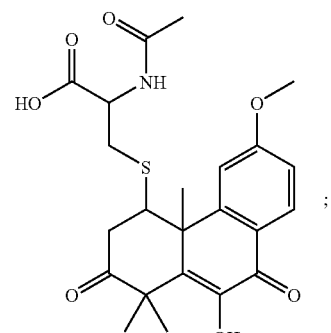

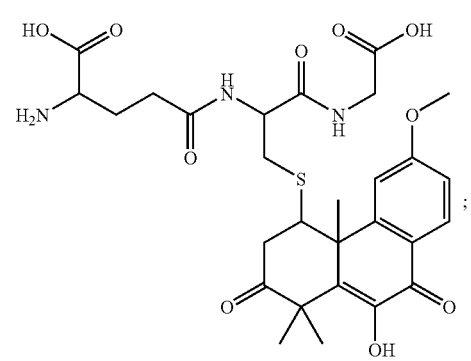

or a pharmaceutically acceptable salt thereof.

19. The compound of claim 11, wherein the compound has the structure:
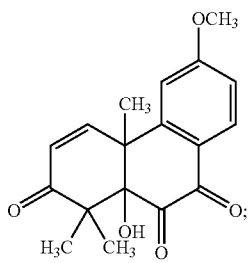
77
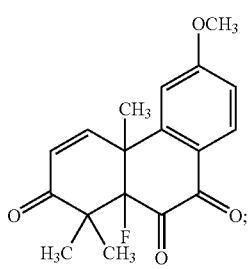
79
or a pharmaceutically acceptable salt thereof.
20. The compound of claim 13, wherein the compound has the structure:
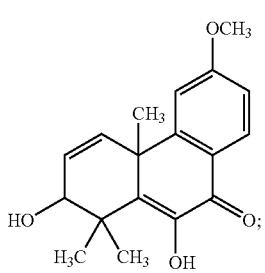
75
or a pharmaceutically acceptable salt thereof.
21. A compound having the structure:
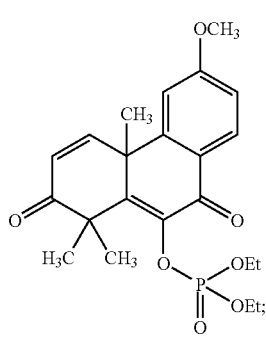
72
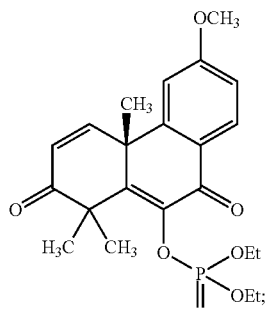
72a
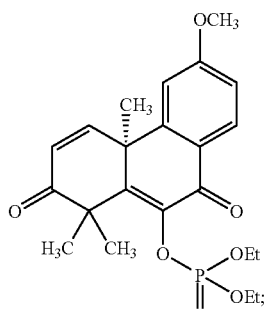
72b
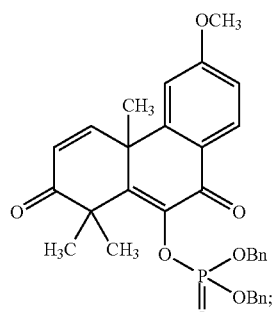
73
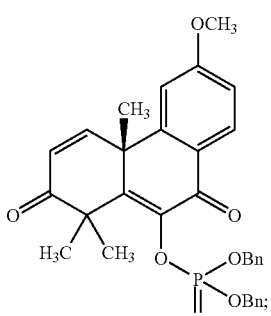
73a
73b -continued

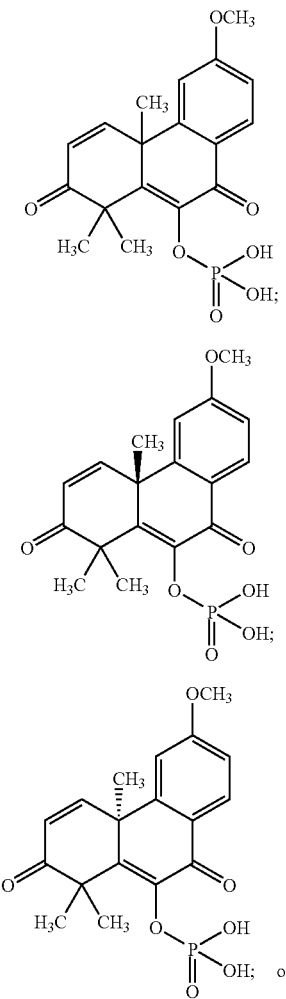

or a pharmaceutically acceptable salt thereof.

22. A pharmaceutical composition comprising (i) an effective amount of the compound or of the pharmaceutically acceptable salt of claim 1, 2, 3, 4, 5, 6, 7, 8, 9, 10, 11, 12, 13, 14, 15, 16, 17, 18, 19, 20, or 21; and (ii) a pharmaceutically acceptable carrier.

23. A pharmaceutical composition comprising (i) an effective amount of a compound; and (ii) a pharmaceutically acceptable carrier, wherein the compound is a compound of the Formula (Ia):

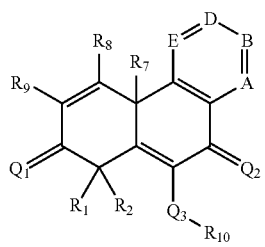

(Ia)

or pharmaceutically acceptable salts thereof, wherein:

$Q_1$ and $Q_2$ are independently =O, =S, =NOR, =NR, =N—NHR, or =N—N(R)$_2$ where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, —OH, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —$OCH_2OR_{11}$, —OC(O)$R_{11}$, —C(O)$R_{11}$, —OC(O)O$R_{11}$, —OC(O)N$R_{11}$, —C(O)O$R_{11}$, —C(O)N$R_{11}$, —OP(O)(O$R_{11}$)$_2$, —S$R_{11}$, —S(O)$_2$NH$R_{11}$, —SO$R_{11}$, —S(O)$_2R_{11}$, —NHC(O)$R_{11}$, —NHSO$R_{11}$, NHS(O)$_2R_{11}$, —OPO(O$R_{15}$)$_2$, —O-arylPO(O$R_{15}$)$_2$, or —O-alkylarylPO(O$R_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —$NH_2$, —$NO_2$, —COOH, —C(O)$NH_2$, —SH, —S(O)$NH_2$, —S(O)$_2NH_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —$CH_2OR_{11}$, —OC$R_{11}$, —OC(O)$R_{11}$, —C(O)$R_{11}$, —OC(O)O$R_{11}$, —OC(O)N$R_{11}$, —C(O)O$R_{11}$, —C(O)N$R_{11}$, —OP(O)(O$R_{11}$)$_2$, —S$R_{11}$, —SO$R_{11}$, —S(O)$_2R_{11}$, —S(O)$_2$NH$R_{11}$, —NHS$R_{11}$, —NHSO$R_{11}$, or —NHS(O)$_2R_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)$NH_2$, —C(O)NH$R_{12}$, —C(O)N(R$_{12}$)$_2$, P(O)(O$R_{13}$)$_2$, or -aryl, wherein $R_{10}$ is not P(O)(O$R_{13}$)$_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

each halogen is independently —F, —Cl, —Br or —I; and $R_{13}$ is H, $C_1$–$C_{10}$ alkyl, aryl, or benzyl.

24. A pharmaceutical composition comprising (i) an effective amount of a compound; and (ii) a pharmaceutically acceptable carrier, wherein the compound is a compound of the Formula (IIa):

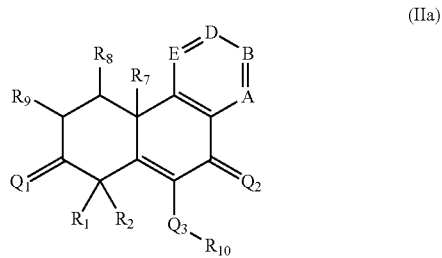

(IIa)

or a pharmaceutically acceptable salt thereof, wherein:

$Q_1$ and $Q_2$ are independently =O, =S, =NOR, =NR, =N—NHR, or =N—N(R)$_2$, where R is —H, —$C_1$–$C_{10}$ alkyl, or -aryl;

$Q_3$ is —O—, —S—, or —N(H)—;

$R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, —OH, -halogen, —CN, —NH$_2$, —NO$_2$, —COOH, —C(O)NH$_2$, —SH, —S(O)NH$_2$, —S(O)$_2$NH$_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein $R_{15}$ is H, —$C_1$–$C_{10}$ alkyl, $C_7$–$C_{12}$arylalkyl, $C_1$–$C_{10}$aminoalkyl, $C_1$–$C_{10}$ haloalkyl, $C_1$–$C_{10}$ hydroxyalkyl, $C_1$–$C_{10}$ alkoxy;

$R_7$ is —H, —$C_1$–$C_{10}$ alkyl, or —$C_1$–$C_{10}$ alkoxy;

$R_8$ and $R_9$ are each independently —H, -halogen, —CN, —NH$_2$, —NO$_2$, —COOH, —C(O)NH$_2$, —SH, —S(O)NH$_2$, —S(O)$_2$NH$_2$, —$C_1$–$C_{10}$ (oxy)alkyl, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, —($C_3$–$C_7$) cycloalkyl, -aryl, —$C_1$–$C_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

$R_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

$R_{10}$ is —H, —$C_1$–$C_{10}$ alkyl, —$C_3$–$C_7$ cycloalkyl, —C(O)$C_1$–$C_{10}$ alkyl, —$C_1$–$C_{10}$ (oxy)alkyl, —C(O)NH$_2$, —C(O)NHR$_{12}$, —C(O)N(R$_{12}$)$_2$, P(O)(OR$_{13}$)$_2$, or -aryl, wherein $R_{10}$ is not P(O)(OR$_{13}$)$_2$ if $Q_3$ is —N(H)— or —S—;

$R_{11}$ is —H, —$C_1$–$C_{10}$ alkyl, —($C_3$–$C_7$) cycloalkyl, —$C_1$–$C_{10}$ (halo)alkyl, -aryl, —$C_2$–$C_{10}$ alkenyl, —$C_2$–$C_{10}$ alkynyl, —$C_1$–$C_{10}$ (aryl)alkyl, —$C_2$–$C_{10}$ (aryl)alkenyl, —$C_2$–$C_{10}$ (aryl)alkynyl, —$C_1$–$C_{10}$ (hydroxy)alkyl, —$C_1$–$C_{10}$ alkoxy, —$C_1$–$C_{10}$ (amino)alkyl, a —($C_3$–$C_7$) cycloalkyl unsubstituted or substituted with one or more —$C_1$–$C_{10}$ alkyl, a three- to seven-membered non-aromatic heterocycle unsubstituted or substituted with one or more —$C_1$–$C_{10}$ alkyl, or a three- to seven-membered aromatic heterocycle unsubstituted or substituted with one or more —$C_1$–$C_{10}$ alkyl, —$C_2$–$C_{10}$ alkenyl, or —$C_2$–$C_{10}$ alkynyl;

$R_{12}$ is $C_1$–$C_{10}$ alkyl;

each halogen is independently —F, —Cl, —Br or —I; and $R_{13}$ is H, $C_1$–$C_{10}$ alkyl, aryl, or benzyl.

25. A pharmaceutical composition comprising (i) an effective amount of a compound; and (ii) a pharmaceutically acceptable carrier, wherein the compound is a compound of the Formula (VIIa):

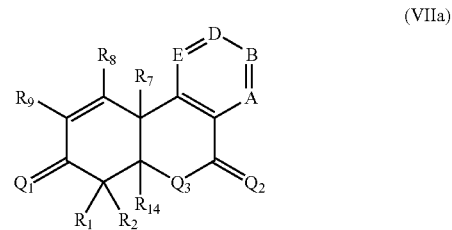

(VIIa)

or a pharmaceutically acceptable salt thereof; wherein $Q_1$ and $Q_2$ are independently =O, =S, =NR, =NOR, =N—NHR, or =N—N(R)$_2$ where R is —H, —$C_1$–$C_{10}$ alkyl, or -aryl;

$Q_3$ is CHOH, CH2, CHOR where R is $C_1$–$C_{10}$ alkyl, aryl, —CH$_2$OR$_{11}$, —C(O)R$_{11}$, —C(O)OR$_{11}$, —C(O)OR$_{11}$, —C(O)NR$_{11}$, or —P(O)(OR$_{11}$)$_2$ $R_1$ and $R_2$ are independently —H, -halogen, -amino, —$C_1$–$C_{10}$ alkyl, —$C_1$–$C_{10}$ alkoxy, —$C_1$–$C_{10}$ (hydroxy)alkyl, —$C_1$–$C_{10}$ (amino)alkyl, —$C_1$–$C_{10}$ (halo)alkyl, —$C_2$–$C_{10}$ alkenyl, —$C_2$–$C_{10}$ alkynyl, ($C_3$–$C_7$) cycloalkyl, -aryl, $C_1$–$C_{10}$ (aryl)alkyl, or three- to seven-membered non-aromatic heterocycle, or $R_1$, $R_2$ and the carbon atom to which they are both attached are taken together to form a ($C_3$–$C_7$) cycloalkyl group or a three- to seven-membered non-aromatic heterocycle;

A is $CR_3$; B is $CR_4$; D is $CR_5$; E is $CR_6$;

each $R_3$, $R_4$, $R_5$ and $R_6$ is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCH$_2$OR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —S(O)$_2$NHR$_{11}$, —SOR$_{11}$, —S(O)$_2$R$_{11}$, —NHC(O)R$_{11}$, —NHSOR$_{11}$, NHS(O)$_2$R$_{11}$, —OPO(OR$_{15}$)$_2$, —O-arylPO(OR$_{15}$)$_2$, or —O-alkylarylPO(OR$_{15}$)$_2$ wherein R$_{15}$ is H, —C$_1$–C$_{10}$ alkyl, C$_7$–C$_{12}$arylalkyl, C$_1$–C$_{10}$aminoalkyl, C$_1$–C$_{10}$ haloalkyl, C$_1$–C$_{10}$ hydroxyalkyl, C$_1$–C$_{10}$ alkoxy;

R$_7$ is —H, —C$_1$–C$_{10}$ alkyl, or —C$_1$–C$_{10}$ alkoxy;

R$_8$ and R$_9$ are each independently —H, -halogen, —CN, —NH$_2$, —NO$_2$, —COOH, —C(O)NH$_2$, —SH, —S(O)NH$_2$, —S(O)$_2$NH$_2$, —C$_1$–C$_{10}$ (oxy)alkyl, —C$_1$–C$_{10}$ alkyl, —C$_1$–C$_{10}$ alkoxy, —C$_1$–C$_{10}$ (hydroxy)alkyl, —C$_1$–C$_{10}$ (amino)alkyl, —C$_1$–C$_{10}$ (halo)alkyl, —C$_2$–C$_{10}$ alkenyl, —C$_2$–C$_{10}$ alkynyl, —(C$_3$–C$_7$) cycloalkyl, -aryl, —C$_1$–C$_{10}$ (aryl)alkyl, three- to seven-membered non-aromatic heterocycle, five- to seven-membered aromatic heterocycle, —CH$_2$OR$_{11}$, —OCR$_{11}$, —OC(O)R$_{11}$, —C(O)R$_{11}$, —OC(O)OR$_{11}$, —OC(O)NR$_{11}$, —C(O)OR$_{11}$, —C(O)NR$_{11}$, —OP(O)(OR$_{11}$)$_2$, —SR$_{11}$, —SOR$_{11}$, —S(O)$_2$R$_{11}$, —S(O)$_2$NHR$_{11}$, —NHSR$_{11}$, —NHSOR$_{11}$, or —NHS(O)$_2$R$_{11}$;

R$_8$ is also —S(CH$_2$)$_n$amino acid, —S(CH$_2$)$_n$peptide, wherein n=0 to 4, wherein the amino acid is connected to the compound through its alpha carbon atom, and wherein the peptide is connected to the compound through the alpha carbon atom of one of its amino acids;

R$_{11}$ is —H, —C$_1$–C$_{10}$ alkyl, —(C$_3$–C$_7$) cycloalkyl, —C$_1$–C$_{10}$ (halo)alkyl, -aryl, —C$_2$–C$_{10}$ alkenyl, —C$_2$–C$_{10}$ alkynyl, —C$_1$–C$_{10}$ (aryl)alkyl, —C$_2$–C$_{10}$ (aryl)alkenyl, —C$_2$–C$_{10}$ (aryl)alkynyl, —C$_1$–C$_{10}$ (hydroxy)alkyl, —C$_1$–C$_{10}$ alkoxy, —C$_1$–C$_{10}$ (amino)alkyl, a —(C$_3$–C$_7$) cycloalkyl unsubstituted or substituted with one or more —C$_1$–C$_{10}$ alkyl, a three- to seven-membered non-aromatic heterocycle unsubstituted or substituted with one or more —C$_1$–C$_{10}$ alkyl, or a three- to seven-membered aromatic heterocycle unsubstituted or substituted with one or more —C$_1$–C$_{10}$ alkyl, —C$_2$–C$_{10}$ alkenyl, or —C$_2$–C$_{10}$ alkynyl;

R$_{12}$ is C$_1$–C$_{10}$ alkyl;

R$_{14}$ is —H, —OH, or halogen; and each halogen is independently —F, —Cl, —Br or —I.

* * * * *